(12) United States Patent
Remenar et al.

(10) Patent No.: US 7,446,107 B2
(45) Date of Patent: *Nov. 4, 2008

(54) CRYSTALLINE FORMS OF CONAZOLES AND METHODS OF MAKING AND USING THE SAME

(75) Inventors: Julius Remenar, Framingham, MA (US); Michael MacPhee, Pawtucket, RI (US); Matthew Peterson, Hopkinton, MA (US); Sherry Morissette, Arlington, MA (US); Orn Almarsson, Shrewsbury, MA (US)

(73) Assignee: Transform Pharmaceuticals, Inc., Lexington, MA (US)

( * ) Notice: Subject to any disclaimer, the term of this patent is extended or adjusted under 35 U.S.C. 154(b) by 672 days.

This patent is subject to a terminal disclaimer.

(21) Appl. No.: 10/926,842

(22) Filed: Aug. 26, 2004

(65) Prior Publication Data

US 2005/0070551 A1 Mar. 31, 2005

Related U.S. Application Data

(60) Continuation-in-part of application No. 10/449,307, filed on May 30, 2003, now Pat. No. 7,078,526, and a continuation-in-part of application No. PCT/US03/17184, filed on May 30, 2003, and a continuation-in-part of application No. PCT/US03/27772, filed on Sep. 4, 2003, which is a continuation-in-part of application No. 10/378,956, filed on Mar. 3, 2003, application No. 10/926,842, which is a continuation-in-part of application No. 10/660,202, filed on Sep. 11, 2003, which is a continuation of application No. PCT/US03/27772, said application No. 10/660,202 is a continuation-in-part of application No. 10/637,829, filed on Aug. 8, 2003, now abandoned, which is a division of application No. 10/295,995, filed on Nov. 18, 2002, now Pat. No. 6,699,840, which is a continuation of application No. 10/232,589, filed on Sep. 3, 2002, now Pat. No. 6,559,293, said application No. 10/660,202 , said application No. PCT/US03/06662 is a continuation-in-part of application No. 10/449,307, filed on May 30, 2003, now Pat. No. 7,078,526, and a continuation-in-part of application No. 10/601,092, filed on Jun. 20, 2003, now abandoned, application No. 10/926,842, which is a continuation-in-part of application No. PCT/US2004/006288, filed on Feb. 26, 2004, said application No. PCT/US03/19574 , said application No. PCT/US03/41273.

(60) Provisional application No. 60/590,590, filed on Jul. 23, 2004, provisional application No. 60/542,752, filed on Feb. 6, 2004, provisional application No. 60/508,208, filed on Oct. 2, 2003, provisional application No. 60/487,064, filed on Jul. 11, 2003, provisional application No. 60/463,962, filed on Apr. 18, 2003, provisional application No. 60/456,027, filed on Mar. 18, 2003, provisional application No. 60/451,213, filed on Feb. 28, 2003, provisional application No. 60/444,315, filed on Jan. 31, 2003, provisional application No. 60/439,282, filed on Jan. 10, 2003, provisional application No. 60/406,974, filed on Aug. 30, 2002, provisional application No. 60/384,152, filed on May 31, 2002, provisional application No. 60/380,288, filed on May 15, 2002, provisional application No. 60/360,768, filed on Mar. 1, 2002, provisional application No. 60/356,764, filed on Feb. 15, 2002.

(51) Int. Cl.
*A61K 31/497* (2006.01)
*C07D 241/06* (2006.01)

(52) U.S. Cl. .................... 514/254.07; 544/336
(58) Field of Classification Search ................ 544/336; 514/254.07

See application file for complete search history.

(56) References Cited

U.S. PATENT DOCUMENTS

| | | | |
|---|---|---|---|
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,267,179 | A | 5/1981 | Heeres et al. |
| 4,764,604 | A | 8/1988 | Muller |
| 4,916,134 | A | 4/1990 | Heeres et al. |
| 5,006,513 | A | 4/1991 | Hector et al. |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,414,997 | A | 5/1995 | Tailer |

(Continued)

FOREIGN PATENT DOCUMENTS

EP  0310122  4/1989

(Continued)

OTHER PUBLICATIONS

McCrone, Walter C., "Polymorphism", in "The Physics and Chemistry of the Organic Solid State, vol. II", Fox, David et al eds, Interscience, New York, pp. 725-767 (1965).

(Continued)

*Primary Examiner*—James O. Wilson
*Assistant Examiner*—Ebenezer Sackey

(57) ABSTRACT

The invention provides novel soluble conazole crystalline forms (e.g. itraconazole, posaconazole and saperconazole) that include salts, co-crystals and related solvates useful as pharmaceuticals. The invention also provides pharmaceutical compositions comprising, and processes for making, these conazole crystalline forms. Methods of using such compositions for the treatment or prevention of systemic and local fungal, yeast, and dermatophyte infections are also provided.

3 Claims, 36 Drawing Sheets

U.S. PATENT DOCUMENTS

| | | | |
|---|---|---|---|
| 5,474,997 | A | 12/1995 | Gray et al. |
| 5,591,767 | A | 1/1997 | Mohr et al. |
| 5,633,015 | A | 5/1997 | Gilis et al. |
| 5,639,476 | A | 6/1997 | Oshlack et al. |
| 5,661,151 | A | 8/1997 | Saksena et al. |
| 5,674,533 | A | 10/1997 | Santus et al. |
| 5,707,975 | A | 1/1998 | Francois et al. |
| 5,733,566 | A | 3/1998 | Lewis |
| 5,998,413 | A | 12/1999 | Heeres et al. |
| 2003/0096014 | A1 | 5/2003 | Sherman |
| 2003/0224006 | A1 | 12/2003 | Zaworotko et al. |
| 2004/0019211 | A1 | 1/2004 | Remenar et al. |
| 2004/0176335 | A1 | 9/2004 | Childs |

FOREIGN PATENT DOCUMENTS

| | | |
|---|---|---|
| EP | 0283992 | 9/1992 |
| WO | WO 94/16733 | 8/1994 |
| WO | WO 95/17407 | 6/1995 |
| WO | WO 98/57967 | 12/1998 |
| WO | WO 01/41536 | 6/2001 |
| WO | WO 01/51919 | 7/2001 |
| WO | WO 01/97853 | 12/2001 |
| WO | WO 02/056878 | 7/2002 |
| WO | WO 02/062318 | 8/2002 |
| WO | WO 03/074474 | 9/2003 |
| WO | WO 03/101392 | 12/2003 |

OTHER PUBLICATIONS

Vippagunta et al., "Crystalline solids", Advanced Drug Delivery Reviews, 48, pp. 3-26 (2001).

Cacciapuoti et al., Antimicrob. Ag. Chemother., 44: p. 2017 (2000).

Callaghan et al., Conazole Dev. Ind. Pharm., vol. 8, pp. 335-369 (1982).

Dannaoui et al., J. Antimicrob. Chemother., 47: pp. 333-340 (2001).

Denning et al., Eur. J. Clin. Microbiol. Infect. Dis., 9: p. 693 (1990).

Dressman et al., Pharm. Res., 15(1): pp. 11-22 (1998).

Ebert, Pharm. Tech., 1(5): pp. 44-50 (1977).

Gascon et al., Eur. J. Clin. Pharmacol., 41: pp. 573-578 (1991).

Heeres et al., J. Med. Chem, 27: pp. 894-900 (1984).

Honig et al., J. Clin. Pharmacol., 33: pp. 1201-1206 (1993).

Imai et al., Intern. Med., 38(10): pp. 829-832 (1999).

Kim et al., J. Chromatog., 738: p. 93 (2000).

Kovacs et al., "New Type of Bridged Monoamino-β-Cyclodextrins", J. of Inclusion Phenomena and Molecular Recognition in Chemistry, 25: pp. 53-56 (1996).

Lavrijsen et al., Lancet, 340: pp. 251-252 (1992).

Neuvonen et al., Clin. Pharmacol. Therap., 60: pp. 54-61 (1996).

Nomeir et al., Antimicrob. Ag. Chemother., 44: p. 727 (2000).

Odds, F.C., J. Antimicrob. Chemother., 24: p. 533 (1989).

Remenar et al., "Crystal Engineering of Novel Cocrystals of a Triazole Drug with 1,4-Dicarboxylic Acids", J. Am. Chem. Soc., 125: pp. 8456-8457 (2003).

Saksena et al., Anti-Infectives: Recent Advances in Chemistry and Structure Activity Relationships (Royal Soc. Chem., Cambridge), pp. 180-199 (1997).

Tetrahedron Letters, 37: p. 5657 (1996).

Tetrahedron Letters, 43(18): pp. 3359-3363 (2002).

Van Cutsem et al., Antimicrob. Ag. Chemother., 33: p. 2063 (1989).

Villa et al., Rev. Inst. Med. Trop., Sao Paulo, pp. 231-234 (Jul.-Aug. 2000).

West, A., Solid State Chemistry and its Applications, Wiley, NY, pp. 358-365 (1988).

Aronhime, J., "Crystalline forms of pharmaceuticals and characterization thereof", Oral Presentation, USPTO, Alexandria, VA, Mar. 8, 2005.

Desiraju, G., "Chemistry beyond the molecule", Nature, 412: pp. 397-400 (2001).

Gavezzotti, A., "Are Crystal Structures Predictable?", Acc. Chem. Res., 27: pp. 309-314 (1994).

Physician's Desk Reference, 56th ed., pp. 1800-1804 (2002).

CRYSTALLINE FORMS OF CONAZOLES AND METHODS OF MAKING AND USING THE SAME

RELATED APPLICATIONS

This application is a continuation-in-part of U.S. application Ser. No. 10/449,307, filed May 30, 2003, which claims the benefit of U.S. Provisional Application No. 60/384,152, filed May 31, 2002, U.S. Provisional Application No. 60/439,282, filed Jan. 10, 2003, U.S. Provisional Application No. 60/444,315, filed Jan. 31, 2003, and U.S. Provisional Application No. 60/463,962, filed Apr. 18, 2003.

This application is also a continuation-in-part of PCT/US03/17184, filed May 30, 2003, which claims the benefit of U.S. application Ser. No. 10/449,307, filed May 30, 2003, U.S. Provisional Application No. 60/384,152, filed May 31, 2002, U.S. Provisional Application No. 60/439,282, filed Jan. 10, 2003, U.S. Provisional Application No. 60/444,315, filed Jan. 31, 2003, and U.S. Provisional Application No. 60/463,962, filed Apr. 18, 2003.

This application is also a continuation-in-part of PCT/US03/27772, filed Sep. 4, 2003, which claims the benefit of U.S. application Ser. No. 10/378,956, filed Mar. 3, 2003, U.S. Provisional Application No. 60/463,962, filed Apr. 18, 2003, U.S. Provisional Application No. 60/451,213, filed Feb. 28, 2003, and U.S. Provisional Application No. 60/487,064, filed Jul. 11, 2003. Said U.S. application Ser. No. 10/378,956, filed Mar. 3, 2003 claims the benefit of U.S. Provisional Application No. 60/360,768, filed Mar. 1, 2002.

This application is also a continuation-in-part of U.S. application Ser. No. 10/660,202, filed Sep. 11, 2003, which claims the benefit of PCT/US03/27772, filed Sep. 4, 2003. Said U.S. application Ser. No. 10/660,202, filed Sep. 11, 2003 also claims the benefit of U.S. application Ser. No. 10/637,829, filed Aug. 8, 2003, which is a divisional of U.S. application Ser. No. 10/295,995, filed Nov. 18, 2002, which is a continuation of U.S. application Ser. No. 10/232,589, filed Sep. 3, 2002, which claims the benefit of U.S. Provisional Application No. 60/406,974, filed Aug. 30, 2002, U.S. Provisional Application No. 60/380,288, filed May 15, 2002, and U.S. Provisional Application No. 60/356,764, filed Feb. 15, 2002. Said U.S. application Ser. No. 10/660,202, filed Sep. 11, 2003, is also a continuation-in-part of U.S. application Ser. No. 10/449,307, filed May 30, 2003, which claims the benefit of U.S. Provisional Application No. 60/463,962, filed Apr. 18, 2003, U.S. Provisional Application No. 60/444,315, filed Jan. 31, 2003, U.S. Provisional Application No. 60/439,282, filed Jan. 10, 2003, and U.S. Provisional Application No. 60/384,152, filed May 31, 2002. Said U.S. application Ser. No. 10/660,202, filed Sep. 11, 2003, is also a continuation-in-part of U.S. application Ser. No. 10/601,092, filed Jun. 20, 2003. Said U.S. application Ser. No. 10/660,202, filed Sep. 11, 2003, also claims the benefit of U.S. Provisional Application No. 60/451,213, filed Feb. 28, 2003, U.S. Provisional Application No. 60/463,962, filed Apr. 18, 2003, and U.S. Provisional Application No. 60/487,064, filed Jul. 11, 2003.

This application is also a continuation-in-part of PCT/US04/006288, filed Feb. 26, 2004, which claims the benefit of U.S. Provisional Application No. 60/451,213, filed Feb. 28, 2003, U.S. Provisional Application No. 60/487,064, filed Jul. 11, 2003, Application No. PCT/US03/27772, filed Sep. 4, 2003, U.S. application Ser. No. 10/660,202, filed Sep. 11, 2003, Application No. PCT/US03/06662, filed Mar. 3, 2003, U.S. Provisional Application No. 60/508,208, filed Oct. 2, 2003, U.S. Provisional Application No. 60/542,752, filed Feb. 6, 2004, U.S. Provisional Application No. 60/463,962, filed Apr. 18, 2003, U.S. application Ser. No. 10/449,307, filed May 30, 2003, U.S. Provisional Application No. 60/456,027, filed Mar. 18, 2003, U.S. application Ser. No. 10/601,092, filed Jun. 20, 2003, Application No. PCT/US03/19574, filed Jun. 20, 2003, and Application No. PCT/US03/41273, filed Dec. 24, 2003.

This application also claims the benefit of U.S. Provisional Application No. 60/590,590, filed Jul. 23, 2004, U.S. Provisional Application No. 60/384,152 filed May 31, 2002, U.S. Provisional Application No. 60/439,282 filed Jan. 10, 2003, U.S. Provisional Application No. 60/444,315 filed Jan. 31, 2003, U.S. Provisional Application No. 60/463,962 filed Apr. 18, 2003, U.S. Provisional Application No. 60/451,213 filed on Feb. 28, 2003 and U.S. Provisional Application No. 60/487,064 Filed on Jul. 11, 2003.

All of the above applications are hereby incorporated by reference in their entireties.

FIELD OF INVENTION

The invention provides novel soluble saperconazole and cis-itraconazole crystalline forms that include salts, co-crystals and polymorphs useful as pharmaceuticals. The invention also provides pharmaceutical compositions comprising, and processes for making, these saperconazole and cis-intraconazole crystalline forms. Methods of using such compositions for the treatment or prevention of systemic and local fungal, yeast, and dermatophyte infections are also provided. In preferred embodiments, the invention provides novel soluble crystalline systems comprising (a) an organic salt comprising the reaction product of saperconazole and an organic or inorganic acid; or (b) a co-crystal comprising the reaction product of saperconazole and an organic or inorganic acid.

In preferred embodiments of the invention, the novel soluble crystalline forms of saperconazole and cis-itraconazole are characterized by a powder X-ray diffraction pattern expressed in terms of 2 theta angles.

BACKGROUND OF THE INVENTION

Systemic fungal diseases (systemic mycoses) are typically chronic conditions that develop very slowly. These diseases are often induced by opportunistic causative fungi that are not normally pathogenic and commonly live in the patient's body or are commonly found in the environment. While systemic fungal diseases used to be relatively rare in temperate countries, there has been an increasing incidence of numerous life-threatening systemic fungal infections that now represent a major threat to susceptible patients. Susceptible patients include immunocompromised patients, particularly those already hospitalized, and patients compromised by HIV infection, ionizing irradiation, corticosteroids, immunosuppressives, invasive surgical techniques, prolonged exposure to antimicrobial agents, and the like, or by diseases or conditions such as cancer, leukemia, emphysema, bronchiectasis, diabetes mellitus, burns, and the like. The symptoms manifested by these fungal diseases are generally not intense, and may include chills, fever, weight loss, anorexia, malaise, and depression.

The most common systemic fungal infections in humans are blastomycosis, candidosis, aspergillosis, histoplasmosis, coccidioidomycosis, paracoccidioidomycosis, and cryptococcosis.

Fungal diseases are often confined to typical anatomic sites, and many involve a primary focus in the lung, with more characteristic manifestations of specific fungal infections appearing once the infection spreads from a primary site. For example, blastomycosis primarily involves the lungs, and occasionally spreads to the skin. Similarly, the primary form of coccidioidomycosis occurs as an acute, benign, self-limiting respiratory disease, which can then progress to a chronic, often-fatal infection of the skin, lymph glands, liver, and spleen. Other infectious diseases such as paracoccidioidomycosis and candidiasis present in different manners, and depending on the etiology, may exhibit several forms involving internal organs, the lymph nodes, skin, and mucous membranes. Diagnosis of specific fungal diseases can be made by isolation of the causative fungus from various specimens, such as sputum, urine, blood, or the bone marrow, or with certain fungus types, through evidence of tissue invasion.

Many patients suffering from severe systemic fungal infections are hardly, or not at all, able to receive medication via oral administration, as such patients are often in a coma or suffering from severe gastroparesis. As a result, the use of insoluble or sparingly soluble antifungals such as itraconazole free base, that are difficult to administer intravenously, to treat such patients is significantly impeded.

Local or superficial fungal infections are caused by dermatophytes or fungi that involve the outer layers of the skin, nails, or hair. Such infections may present as a mild inflammation, and can cause alternating remissions and eruptions of a gradually extending, scaling, raised lesion. Yeast infections, such as candidiasis and oral candidiasis (thrush), are usually localized to the skin and mucous membranes, with the symptoms varying depending on the site of infection. In many instances, such infections appear as erythematous, often itchy, exudative patches in the groin, axillas, umbilicus, between toes, and on finger-webs. Oral thrush involves an inflamed tongue or buccal mucosa, typically accompanied by white patches of exudate. Chronic mucocutaneous candidiasis is manifested in the form of red, pustular, crusted, thickened lesions on the forehead or nose.

Itraconconazole Chemistry and Uses

Itraconazole is a broad-spectrum antifungal agent developed for oral, parenteral and topical use, and is disclosed in U.S. Pat. No. 4,267,179. Itraconazole is a synthetic triazole derivative that disrupts the synthesis of ergosterol, the primary sterol of fungal cell membranes. This disruption appears to result in increased permeability and leakage of intracellular content, and at high concentration, cellular internal organelles involute, peroxisomes increase, and necrosis occurs.

As set forth in the USP Dictionary of Drug Names and USAN, itraconazole is defined as (±)-1-sec-butyl-4-[p-[4-[p-[[(2R*,4S*)-2-(2,4-dichlorophenyl)-2-(1H-1,2,4-triazol-1-ylmethyl)-1,3-dioxolan-4-yl]methoxy]phenyl]-1-piperazinyl]phenyl]-$\Delta^2$-1,2,4-triazolin-5-one, or alternatively, as 4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one. There are three asymmetric carbons in itraconazole: one in the sec-butyl side chain on the triazolone and two in the dioxolane ring. As a result, eight possible stereoisomers of itraconazole exist: (R,R,R), (S,S,S), (R,R,S), (S,S,R), (R,S,S), (R,S,R), (S,R,S), and (S,R,R).

(±)Cis-Itraconazole comprises a mixture of only those isomers that describe a "cis" relationship in the dioxolane ring, i.e., the (1H-1,2,4-triazol-1-ylmethyl) moiety and the substituted phenoxy moiety are located on the same side of a plane defined by the 1,3-dioxolane ring. By convention, the first represented chiral center is at C-2 of the dioxolane ring, the second is at C-4 of the dioxolane ring, and the third is in the sec-butyl group. Hence, (±)cis-itraconazole is a mixture of (R,S,S), (R,S,R), (S,R,S) and (S,R,R) isomers.

The four possible stereoisomeric cis forms of itraconazole, and diastereomeric pairs thereof, are described in more detail in U.S. Pat. Nos. 5,474,997 and 5,998,413. In general, the individual stereoisomeric forms of cis-itraconazole have antifungal properties, and contribute to the overall activity of (±)cis-itraconazole.

(±)Cis-Itraconazole free base is only very sparingly soluble in water, and thus it is extremely difficult to prepare effective pharmaceutical compositions containing the same. A number of means have been used to increase the solubility of itraconazole free base, including complexing or co-formulation with cyclodextrins or derivatives thereof, as described in U.S. Pat. No. 4,764,604, U.S. Pat. No. 5,998,413, and U.S. Pat. No. 5,707,975, and coating beads with a film comprising a hydrophilic polymer and itraconazole, as described in U.S. Pat. No. 5,633,015.

Another approach to increase solubility of itraconazole focuses on preparation of the stereoisomers of cis-itraconazole, and in particular (2R, 4S) itraconazole, which may comprise a mixture of two diastereomers ((R,S,S) and (R,S,R)), as described in U.S. Pat. Nos. 5,414,997 and 5,998,413.

Commercially available itraconazole (SPORANOX® brand (±)cis-itraconazole Janssen Pharmaceutica Products, L.P., Titusville, N.J., U.S.A.) is a free base and a racemic mixture of the cis isomer in the dioxolane ring and is represented by structural formula (I):

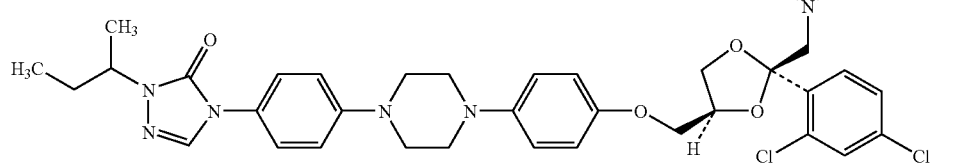

SPORANOX® has been approved for use as an antifungal agent for treating immunocompromised and non-immunocompromised patients having: blastomycosis (pulmonary and extrapulmonary); histoplasmosis, including chronic cavitary pulmonary disease and disseminated non-meningeal histoplasmosis; and aspergillosis. In addition, in non-immunocompromised patients, it has been approved for treatment of onychomycosis. See generally, Physician's Desk Reference, 56th ed. (2002). The compound has also been investigated for use in coccidioidomycosis, cryptococcosis, dermatophyte, and candidiasis infections.

Adverse effects associated with the administration of (±)cis-itraconazole free base include nausea, vomiting, anorexia, headache, dizziness, hepatotoxicity, and inhibition of drug metabolism in the liver, leading to numerous, clinically significant, adverse drug interactions. See, Physician's Desk Reference, 56th ed. (2002); Honig et al., J. Clin. Pharmacol. 33:1201-1206 (1993) (terfenadine interaction); Gascon and Dayer, *Eur. J. Clin. Pharmacol.*, 41:573-578 (1991) (midazolam interaction); and Neuvonen et al., *Clin. Pharmacol. Therap.*, 60:54-61 (1996) (lovastatin interaction). Reactions associated with hypersensitivity, such as urticaria and serum liver enzymes elevation, are also associated with the administration of the drug. A more serious, though less common, adverse effect is hepatoxicity. See, e.g., Lavrijsen et al., *Lancet*, 340:251-252 (1992).

In addition, as discussed herein, cis itraconazole free base is only very sparingly soluble in water. Thus, due its relative non-polarity and insolubility, itraconazole free base suffers from two other drawbacks: it cannot be readily formulated in parenteral solution, and it does not effectively penetrate the blood-brain barrier. The latter problem is exacerbated by drug interactions, such as one observed between itraconazole free base and valproate, as described in Villa et al., *Rev. Inst. Med. Trop., Sao Paulo, pp.* 231-234 (July-August 2000), which is incorporated by reference herein in its entirety. In another case of CNS fungal infection, extremely high doses of itraconazole free base were used to treat residual aspergillus infection, as reported by Imai et al., *Intern. Med.*, 38(10):829-832 (1999), which is incorporated by reference herein in its entirety. As a result, numerous therapeutic indications that require rapid achievement of effective blood levels or access to the CNS are difficult to treat or beyond treatment with itraconazole free base.

Furthermore, the emergence of antifungal resistance (e.g., in *Aspergillus fumigatus* isolates as described by Dannaoui et al., *J. Antimicrob. Chemother.*, 47:333-340 (2001), which is incorporated by reference herein in its entirety) presents an added challenge to the efficacy of itraconazole free base. For those strains of fungi that show resistance, high and relatively constant levels of itraconazole free base must be produced in the target organs of infected patients.

Over the years, a number of formulation routes have been used in order to enhance the adsorption and bioavailability of itraconazole. For example, the currently marketed SPORANOX® solid dosage capsule form of itraconazole free base utilizes sugar-based beads coated with a hydrophilic polymer and an amorphous film of itraconazole. See *Physicians Desk Reference*, 56th ed., pp. 1800-1804 (2002); and U.S. Pat. No. 5,633,015. This dosage form requires up to two capsules three times daily depending on the condition being treated.

Even with the various formulation routes, the dosage amounts and dose frequency for itraconazole can be burdensome to patients. In addition, administration of existing dosage forms of itraconazole have shown significant variability in bioavailability and adsorption, which variability likely results from food effects. See, *Physician's Desk Reference*, 56th ed., pp. 1800-1804 (2002). Thus, it would be desirable to increase bioavailability and adsorption and decrease the per-dose pill count and decrease dosing frequency (e.g., twice a day to once a day) associated with administration of itraconazole in order to provide an improvement over current therapy, particularly with regard to patient compliance, convenience, ease of ingestion, especially with regard to immunocompromized polypharmacy patients (e.g., AIDS or cancer patients).

Posaconazole and Saperconazole Chemistry and Uses

Other related conazoles have also been discovered and used as antifungals. Two of these conazoles that are closely structurally related to itraconazole are Posaconazole and Saperconazole. Posaconazole (CAS Registry Number: 171228-49-2; CAS Name: 2,5-Anhydro-1,3,4-trideoxy-2-C-(2,4-difluorophenyl)-4-[[4-[4-[4-[1-[(1S,2S)-1-ethyl-2-hydroxypropyl]-1,5-dihydro-5-oxo-4H-1,2,4-triazol-4-yl]phenyl]-1-piperazinyl]phenoxy]methyl]-1-(1H-1,2,4-triazol-1-yl)-D-threo-pentitol; Additional Names: (3R-cis)-4-[4-[4-[4-[5-(2,4-difluorophenyl)-5-(1,2,4-triazol-1-ylmethyl) tetrahydrofuran-3-ylmethoxy]phenyl]piperazin-1-yl]phenyl]-2-[1(S)-ethyl-2(S)-hydroxypropyl]-3,4-dihydro-2H-1,2,4-triazol-3-one) is represented by structural formula (II):

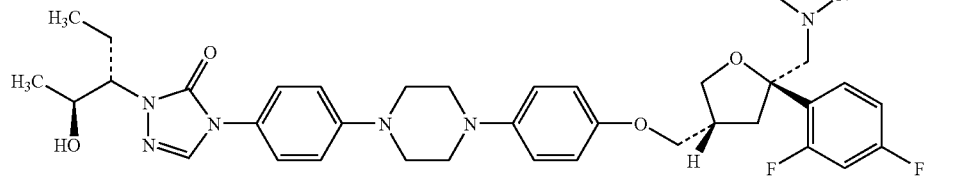

(II)

Saperconazole (CAS Registry Number: 110588-57-3; CAS Name: 4-[4-[4-[4-[[2-(2,4-Difluorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; Additional Names: (±)-1-sec-butyl-4-[p-[4-[p-[[(2R*,4S*)-2-(2,4-difluorophenyl)-2-(1H-1,2,4-triazol-1-ylmethyl)-1,3-dioxolan-4-yl]methoxy]phenyl]-1-piperazinyl]phenyl]-Δ²-1,2,4-triazolin-5-one) is represented by structural formula (III):

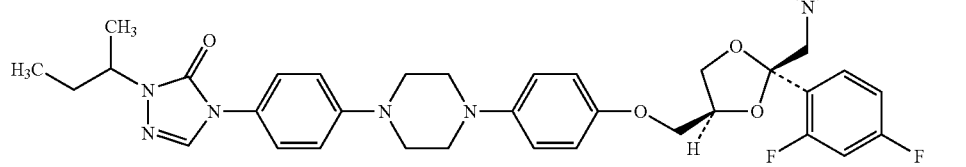

(III)

Consequently, there is a need for soluble forms of conazoles including cis itraconazole, posaconazole and saperconazole that can be readily formulated for use in various modes of administration, including parenteral and oral administration.

SUMMARY OF THE INVENTION

The invention provides novel soluble crystalline forms of conazoles including cis-itraconazole,posaconazole or saperconazole comprising the reaction product of the conazole and an organic acid or an inorganic acid including salts, co-crystals, solvates, hydrates and multicomponent crystal systems having three or more components (including itraconazole). In one embodiment, the soluble crystalline form of the conazole, comprises the reaction product of the conazole, e.g., cis-itraconazole, posaconazole or saperconazole, and a dicarboxylic acid or a carboxylic acid. The invention provides soluble crystalline forms of an organic solvate of a conazole including cis-itraconazole, posaconazole or saperconazole salts, and crystalline forms of the acid salts of a conazole, such as cis-itraconazole, posaconazole or saperconazole HCl salt tartaric acid co-crystal. The invention includes novel soluble conazole (e.g., cis-itraconazole, posaconazole or saperconazole) salts, co-crystals, solvates (including hydrates), and polymorphs.

In one embodiment, the invention provides a soluble, multicomponent crystalline system comprising:
(a) the reaction product of a conazole and an organic acid or an inorganic acid; and
(b) one or more organic or inorganic solvents wherein the organic solvent is present in the system in either a stoichiometric or non-stoichiometric ratio relative to the organic salt or a second reaction product of a conazole and an organic acid or an inorganic acid.

In a further embodiment, the multicomponent crystalline system is a co-crystal comprising a co-crystal former and a conazole.

In a further embodiment, the reaction product is a salt.

In a further embodiment, the reaction product is a co-crystal.

In a further embodiment, the first reaction product is a salt and the second reaction product is a co-crystal.

In a further embodiment, the system comprises a first reaction product, a second reaction product and a solvent.

In a further embodiment, the invention provides for a co-crystal comprising a co-crystal former and a conazole free base or a co-crystal former and a conazole salt. Either co-crystal form may further comprise a solvent as provided for herein.

Further, in preferred embodiments of the invention, the novel soluble crystalline form of cis-itraconazole is characterized by an endothermic transition temperature, a Raman spectrum, a crystal morphology or by selected peaks of a powder X-ray diffraction pattern expressed in terms of 2 theta angles, wherein the X-ray powder diffraction patterns comprise the 2 theta angle values listed herein.

The invention also provides pharmaceutical compositions comprising, and processes for making, conazole (e.g., cis itraconazole posaconazole or saperconazole) crystalline forms including salts, co-crystals, solvates, etc. Methods of using such compositions for the treatment or prevention of systemic and local fungal, yeast, and dermatophyte infections are also provided.

Compounds of the invention include, but are not limited to, soluble crystalline forms of conazoles including: cis-itraconazole, posaconazole or saperconazole D, L, and D, L-tartaric acid co-crystal, cis-itraconazole, posaconazole or saperconazole citrate, cis-itraconazole, posaconazole or saperconazole fumaric acid co-crystal, cis-itraconazole, posaconazole or saperconazole malonic acid co-crystal, cis-itraconazole, posaconazole or saperconazole maleic acid co-crystal, cis-itraconazole, posaconazole or saperconazole adipic acid co-crystal, cis-itraconazole, posaconazole or saperconazole di-mesylate, cis-itraconazole, posaconazole or saperconazole succinic acid co-crystal, cis-itraconazole, posaconazole or saperconazole sulfate, cis-itraconazole, posaconazole or saperconazole benzenesulfonate, cis-itraconazole, posaconazole or saperconazole besylate, cis-itraconazole, posaconazole or saperconazole di-HCl, cis-itraconazole, posaconazole or saperconazole malic acid co-crystal, cis-itraconazole, posaconazole or saperconazole HCl salt D, L, or D, L-tartaric acid co-crystal, cis-itraconazole, posaconazole or saperconazole di-mesylate dioxane solvate, cis-itraconazole, posaconazole or saperconazole di-mesylate ethanol solvate, or cis-itraconazole, posaconazole or saperconazole phosphate, as well as acid salts, multicomponent co-crystals of cis-itraconazole, posaconazole or saperconazole salts, co-crystals, solvates, and hydrates of these compounds. Preferred soluble crystalline forms of conazoles (e.g., cis-itraconazole, posaconazole or saperconazole) of the invention include dicarboxylic acid salts, dicarboxylic acid co-crystals, and hydrochloric acid salt co-crystals. Other preferred soluble crystalline forms of cis-itraconazole, posaconazole or saperconazole include hydrochloric acid, phosphoric acid, sulfuric acid or benzenesulfonic acid salts and co-crystals. Other preferred compounds of the invention include crystalline forms of an alcohol solvate (e.g., ethanol, methanol, propylene glycol, propanol, etc.) or dioxane solvate, or a conazole (e.g., a cis-itraconazole, posaconazole or saperconazole) co-crystal such as tartaric acid co-crystal, fumaric acid co-crystal, malic acid co-crystal, maleic acid co-crystal, adipic acid co-crystal, di-mesylate, and succinic acid co-crystal. In one embodiment the co-crystal comprises a co-crystal former and a conazole salt. In another embodiment, the co-crystal further comprises a solvent.

In another embodiment, the present invention provides a soluble crystalline form or a formulation of a soluble crystalline form of a conazole with a decreased food effect. In a specific embodiment, a soluble crystalline form or a formulation of a soluble crystalline form of itraconazole is provided which has a decreased food effect with respect to that of a reference form (e.g., itraconazole free base, a salt of itraconazole, or a polymorph, hydrate solvate, or co-crystal thereof) or a reference formulation (e.g., Sporanox®).

In another embodiment, the present invention provides a method for decreasing the food effect of a conazole. A method for decreasing the food effect of a conazole is provided, comprising administering to a mammal a soluble crystalline form or a formulation of a soluble crystalline form of the present invention. For example, a method for decreasing the food effect of itraconazole comprises administering to a mammal a soluble crystalline form or a formulation of a soluble crystalline form of the present invention such as, but not limited to, itraconazole HCl:DL-tartaric acid co-crystal. The decrease in food effect discussed in the above methods can be measured with respect to the food effect observed from a reference form (e.g., itraconazole free base, a salt of itraconazole, or a polymorph, hydrate solvate, or co-crystal thereof) or a reference formulation (e.g., Sporanox®).

The invention further provides methods of treating or preventing local and systemic fungal, yeast, and dermatophyte infections in a patient by administration of therapeutically or prophylactically effective amounts of soluble crystalline forms of a conazole such as cis-itraconazole, posaconazole or saperconazole, comprising the reaction product of a conazole such as cis-itraconazole, posaconazole or saperconazole, and an organic acid or an inorganic acid. Pharmaceutical dosage forms of the invention comprise therapeutically or prophylactically effective amounts of soluble crystalline forms of a conazole (e.g., cis-itraconazole, posaconazole or saperconazole) comprising the reaction product of cis-itraconazole, posaconazole or saperconazole and an organic acid or an inorganic acid.

DETAILED DESCRIPTION OF THE INVENTION

Figure 1A:
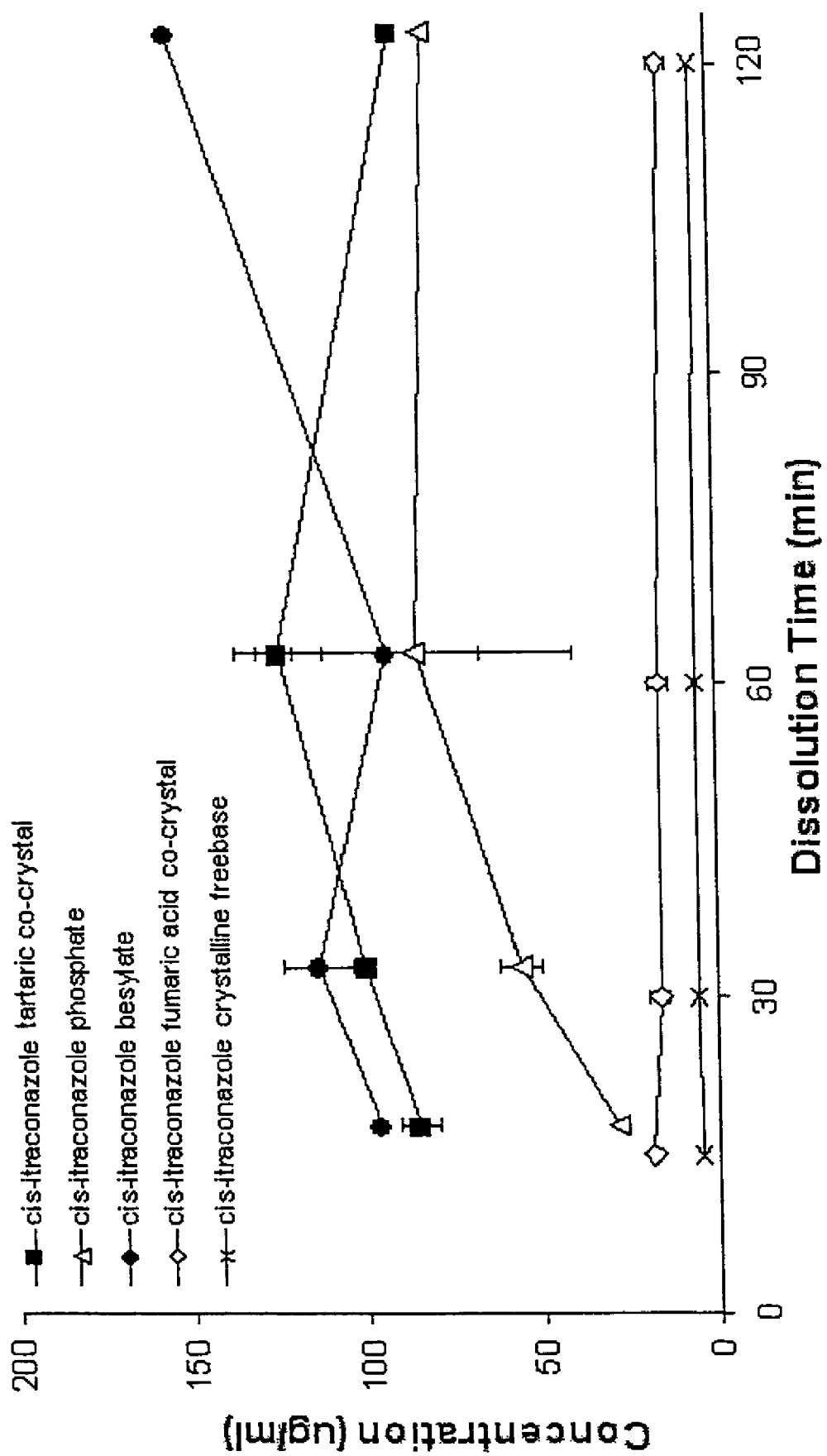
FIGS. 1A & 1B compares the dissolution ratio of cis-itraconazole free base and crystalline forms of cis-itraconazole.

As used herein, the following terms have the following respective meanings.

As used herein, the term "solvate" is a complex of variable stoichiometry formed by a solute (either cis-itraconazole, posaconazole or saperconazole or salts, co-crystals, hydrates, or polymorphs of cis-itraconazole, posaconazole or saperconazole) and an organic solvent as defined herein, including an alcohol, preferably methanol or ethanol, or dioxane.

"Carboxylic acids" include, but are not limited to, formic, acetic, propionic, butyric, isobutyric, valeric, isovaleric, pivalic, caproic, caprylic, capric, lauric, myristic, palmitic, stearic, acrylic, crotonic, benzoic, cinnamic, and salicylic acids. "Dicarboxylic acid" means a compound of formula (II):

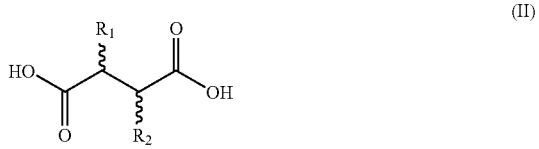

wherein $R_1$ and $R_2$ are each independently H, OH, Cl, Br, I, substituted or unsubstituted $C_{1-6}$ alkyl, substituted or unsubstituted aryl or $R_1$ and $R_2$ taken together represent a double bond as well as stereochemically pure D or L salts of a compound of formula (II). Examples of the dicarboxylic acid of formula (II) include but are not limited to succinic acid, maleic acid, tartaric acid, malic acid or fumaric acid. Most preferably, the dicarboxylic acid of formula (II) is succinic acid, tartaric acid or malic acid. Least preferably, the dicarboxylic acid of formula (II) is maleic acid or fumaric acid. It should be recognized that additional dicarboxylic acids such as malonic acid and adipic acid are distinct embodiments of the invention although they fall outside the scope of formula (II).

"Organic or inorganic acids" include, but are not limited to, carboxylic acids, dicarboxylic acids, hydrochloric acid, phosphoric acid, sulfuric acid, benzenesulfonic acid, methanesulfonic acid, and, in general terms, any acidic species that will form a thermodynamically stable crystalline (salt) form upon reaction with the free base cis-itraconazole, posaconazole or saperconazole.

The term "co-crystal" as used herein means a crystalline material comprised of two or more unique solids at room temperature, each containing distinctive physical characteristics, such as structure, melting point and heats of fusion, with the exception that, if specifically stated, the active pharmaceutical ingredient (API) may be a liquid at room temperature. The co-crystals of the present invention comprise a co-crystal former H-bonded to an API. The co-crystal former may be H-bonded directly to the API or may be H-bonded to an additional molecule which is bound to the API. The additional molecule may be H-bonded to the API or bound ionically or covalently to the API. The additional molecule could also be a different API. Solvates of API compounds that do not further comprise a co-crystal former are not co-crystals according to the present invention. The co-crystals may however, include one or more solvate molecules in the crystalline lattice. That is, solvates of co-crystals, or a co-crystal further comprising a solvent or compound that is a liquid at room temperature, is included in the present invention, but crystalline material comprised of only one solid and one or more liquids (at room temperature) are not included in the present invention, with the previously noted exception of specifically stated liquid APIs. The co-crystals may also be a co-crystal between a co-crystal former and a salt of an API, but the API and the co-crystal former of the present invention are constructed or bonded together through hydrogen bonds. Other modes of molecular recognition may also be present including, pi-stacking, guest-host complexation and van der Waals interactions. Of the interactions listed above, hydrogen-bonding is the dominant interaction in the formation of the co-crystal, (and a required interaction according to the present invention) whereby a non-covalent bond is formed between a hydrogen bond donor of one of the moieties and a hydrogen bond acceptor of the other. Hydrogen bonding can result in several different intermolecular configurations. For example, hydrogen bonds can result in the formation of dimers, linear chains, or cyclic structures. These configurations can further include extended (two-dimensional) hydrogen bond networks and isolated triads. An alternative embodiment provides for a co-crystal wherein the co-crystal former is a second API. In another embodiment, the co-crystal former is not an API. In another embodiment the co-crystal comprises two co-crystal formers. For purposes of the present invention, the chemical and physical properties of an API in the form of a co-crystal may be compared to a reference compound that is the same API in a different form. The reference compound may be specified as a free form, or more specifically, a free acid, free base, or zwitterion; a salt, or more specifically for example, an inorganic base addition salt such as sodium, potassium, lithium, calcium, magnesium, ammonium, aluminum salts or organic base addition salts, or an inorganic acid addition salts such as HBr, HCl, sulfuric, nitric, or phosphoric acid addition salts or an organic acid addition salt such as acetic, propionic, pyruvic, malanic, succinic, malic, maleic, fumaric, tartaric, citric, benzoic, methanesulfonic, ethanesulfuric, stearic or lactic acid addition salt; an anhydrate or hydrate of a free form or salt, or more specifically, for example, a hemihydrate, monohydrate, dihydrate, trihydrate, quadrahydrate, pentahydrate, sesquihydrate; or a solvate of a free form or salt. For example, the reference compound for an API in salt form co-crystallized with a co-crystal former can be the API salt form. Similarly, the reference compound for a free acid API co-crystallized with a co-crystal former can be the free acid API. The reference compound may also be specified as crystalline or amorphous.

"Soluble crystalline forms" or "soluble, multicomponent crystalline systems" encompass crystalline (or co-crystalline) species including salts, hydrates, solvates, multicomponent crystalline systems or crystalline polymorphs that are soluble in aqueous media at values greater than 5 mcg(microgram)/ml, more preferably greater than 10 mcg/ml, more preferably greater than 20 mcg/ml, more preferably greater than 30 mcg/ml, more preferably greater than 40 mcg/ml, more preferably greater than 50 mcg/ml, and most preferably greater than 100 mcg/ml in a solution with a pH of about 1. Soluble multicomponent crystalline systems can comprise: (a) an organic compound (salt, co-crystal or a co-crystal of a salt and a second molecule) comprising the reaction product of cis-itraconazole, posaconazole or saperconazole and an organic acid or an inorganic acid; and (b) one or more organic solvents, wherein the organic solvent is present in either a stoichiometric or non-stoichiometric ratio relative to the organic salt.

"Organic solvent" includes, but not is limited to, 1,4 dioxane ("dioxane"), 1,2-dichloroethane, dimethoxyethane, diethylene glycol dimethyl ether, tetrahydrofuran, diisopropyl ether, hydrocarbons such as hexane, heptane, cyclohexane, toluene or xylene, alcohols such as methanol, ethanol, 1-propanol, 2-propanol, 1-butanol, 2-butanol, tert-butanol or ethylene glycol, ketones such as methyl ethyl ketone or isobutyl methyl ketone, amides such as dimethylformamide, dimethylacetamide or N-methylpyrrolidone, dimethoxyethane, tetrahydrofuran, dioxane, cyclohexane, toluene, xylene, alcohols, e.g. methanol, ethanol, 1-propanol, 2-propanol, 1-butanol, tert-butanol and mixtures thereof. 1,2-dichloroethane and ethanol are preferred organic solvents.

The term "anomer" as used herein means one of a pair of isomers of a cyclic compound resulting from creation of a new point of symmetry when a rearrangement of atoms occurs at an aldehyde or ketone position.

"Alkyl" means a straight chain or branched, saturated or unsaturated alkyl, cyclic or non-cyclic hydrocarbon having from 1 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Unsaturated alkyls contain at least one double or triple bond between adjacent carbon atoms (also referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cycloalkyls are also referred to herein as "carbocyclic" rings systems, and include bi- and tri-cyclic ring systems having from 8 to 14 carbon atoms such as a cycloalkyl (such as cyclopentane or cyclohexane) fused to one or more aromatic (such as phenyl) or non-aromatic (such as cyclohexane) carbocyclic rings.

As used herein, the term "aryl" means a carbocyclic or heterocyclic aromatic group containing from 5 to 10 ring atoms. The ring atoms of a carbocyclic aromatic group are all carbon atoms, and include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. A carbocyclic aromatic group can be unsubstituted or substituted. Preferably, the carbocyclic aromatic group is a phenyl group. The ring atoms of a heterocyclic aromatic group contains at least one heteroatom, preferably 1 to 3 heteroatoms, independently selected from nitrogen, oxygen, and sulfur. Illustrative examples of heterocyclic aromatic groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, furyl, phienyl, isoxazolyl, indolyl, oxetanyl, azepinyl, piperazinyl, morpholinyl, dioxanyl, thietanyl and oxazolyl. A heterocyclic aromatic group can be unsubstituted or substituted. Preferably, a heterocyclic aromatic is a monocyclic ring, wherein the ring comprises 2 to 5 carbon atoms and 1 to 3 heteroatoms.

The term "substituted" as used herein means any of the above groups (i.e., aryl or alkyl) wherein at least one hydrogen atom is replaced with a substituent. In the case of a keto substituent ("C(=O)") two hydrogen atoms are replaced. Substituents include halogen, hydroxy, alkyl, aryl, arylalkyl, heterocycle or heterocyclealkyl.

As used herein, the terms "itraconazole" and "cis-itraconazole" refer to (±)cis-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one, its four stereoisomers (+)-[2R-[2α,4α,4(R)]-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one (also referred to as the (R,S,R) stereoisomer), (+)-[2R-[2α,4α,4(S)]-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one (also referred to as the (R,S,S) stereoisomer), (−)-[2S-[2α,4α,4(R)]-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one (also referred to as the (S,R,R) stereoisomer), and (−)-[2S-[2α,4α,4(S)]-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one (also referred to as the (S,R,S) stereoisomer) and diastereomeric pairs thereof, unless specified otherwise.

As used herein, the term "cis-itraconazole, posaconazole or saperconazole tartaric acid co-crystal" refers to novel soluble crystalline forms of cis-itraconazole, posaconazole or saperconazole-DL-tartaric acid co-crystal, cis-itraconazole, posaconazole or saperconazole-L-tartaric acid co-crystal, and cis-itraconazole, posaconazole or saperconazole-D-tartaric acid co-crystal. Similarly, where appropriate the other salts refer to racemic or "DL" salts unless otherwise indicated.

As used herein, the term "cis-itraconazole, posaconazole or saperconazole-HCl" means the hydrochloric acid salt of novel soluble crystalline forms of cis-itraconazole, posaconazole or saperconazole.

As used herein, the terms "stereoisomer" or "stereoisomeric form" means compounds having a stereoisomeric purity of at least 90%, and preferably at least 95% up to a stereoisomeric purity of 100% by weight, preferably compounds having a stereoisomeric purity of at least 97% up to a stereoisomeric purity of 100%, and more preferably having a stereoisomeric purity of at least 99% up to a stereoisomeric purity of 100% by weight, said weight percent based upon the total weight of the desired stereoisomers of the compound.

As used herein, the term "diastereomeric pair" refers to a mixture of two stereoisomers of cis-itraconazole, and in particular, either 1) a mixture of (+)-[2R-[2α,4α,4(R)]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one (the (R,S,R) stereoisomer) and (+)-[2R-[2α,4α,4(S)]-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one (the (R,S,S) stereoisomer), or 2) a mixture of (−)-[2S-[2α,4α,4(R)]-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one (the (S,R,R) stereoisomer), and (−)-[2S-[2α,4α,4(S)]-4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one (the (S,R,S) stereoisomer). In a preferred embodiment, the mixture is in the range of a 47:53 to a 53:47 mixture by weight, more preferably in the range of a 48:52 to a 52:48 mixture by weight, and most preferably the mixture is a 50:50 mixture by weight.

As used herein, the term "adjunctively administered" refers to the administration of one or more compounds or active ingredients in addition to a pharmaceutically acceptable salt and co-crystal of cis-itraconazole, posaconazole or saperconazole, or a hydrate, solvate or polymorph thereof, either simultaneously with the same or at intervals prior to, during, or following administration of the pharmaceutically acceptable salt of cis-itraconazole, posaconazole or saperconazole to achieve the desired therapeutic or prophylactic effect.

As used herein, the term "pharmaceutically acceptable salt" refers to a salt prepared from pharmacologically acceptable anions, such as hydrochloride, phosphate, formate, adipic acid co-crystal, succinic acid co-crystal, fumaric acid co-crystal, malic acid co-crystal, tartrate, malonic acid co-crystal, maleic acid co-crystal, mesylate and benzenesulfonate. Particularly preferred anions are tartrate, benzenesulfonate, malic acid co-crystal and succinic acid co-crystal, and other co-crystals, hydrobromide, bitartrate, para-toluenesulfonate, glycolate, glucuronate, mucate, gentisate, isonicotinate, saccharate, acid phosphate, hydroiodide, nitrate, sulfate, bisulfate, acetate, propionate, camphorsulfonate, gluconate, isothionate, lactate, furoate, glutamate, ascorbate, benzoate, anthranilate, salicylate, phentylacetate, mandelate, embonate (pamoate), methanesulfonate, ethanesulfonate, pantothenate, stearate, sulfanilate, alginate, p-toluenesulfonate, mesylate, and galacturonate.

As used herein, the term "method of treating or preventing local and systemic fungal, yeast and dermatophyte infections" means prevention of, or relief from local and systemic fungal, yeast and dermatophyte infections, or one or more symptoms thereof. Local and systemic fungal, yeast and dermatophyte infections include, but are not limited to blastomycosis, aspergillosis, histoplasmosis, onychomycosis, coccidioidomycosis, paracoccidioidomycosis, cryptococcosis, dermatophyte, and candidiasis infections.

The terms "itraconazole" and "cis-itraconazole" are used interchangeably throughout this disclosure.

The term "conazole" refers to compounds comprising a substituted or unsubstituted 1, 2, 4-triazol group or a substituted or unsubstituted 1-H-imidazole group. Conazoles can further be specified as having antifungal activity and useful as an active pharmaceutical ingredient. Conazoles can further be defined as comprising both a 1, 2, 4-triazol and a 1-H-imidazole group and, optionally, having antifingal activity. Further more specific compounds of the present invention include salts, co-crystals, multicomponent systems, solvates, hydrates and polymorphs of itraconazole, posaconazole, saperconazole and derivatives thereof:

Itraconazole

This invention is concerned in past with 1H-imidazoles and 1H-1,2,4-triazoles having the formula

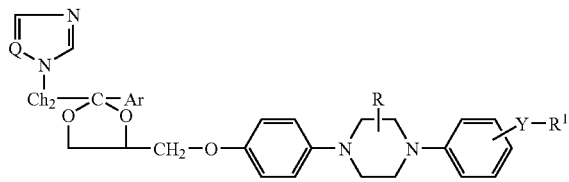

Formula (V)

and the stereochemically isomeric forms thereof, wherein

Q is N or CH;

Ar is aryl;

R is hydrogen or $C_{1-6}$ alkyl; and $Y$—$R^1$ is a radical having the formula

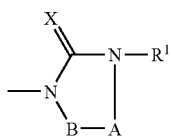

Formula (a)

or a radical having the formula

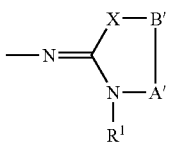

Formula (b)

wherein $R^1$ is tetrahydrofuranyl$C_{1-6}$ alkyl; or $C_{1-6}$ alkyl, $C_{3-6}$ cycloalkyl, aryl$C_{1-6}$ alkyl or $(C_{3-6}$ cycloalkyl$)C_{1-6}$ alkyl all substituted on the $C_{1-6}$ alkyl and/or $C_{3-6}$ cycloalkyl moiety with oxo, thioxo or with one or two radicals of formula —Z—$R^{1-a}$;

said Z being O or S;

said $R^{1-a}$ being hydrogen, $C_{1-6}$ alkyl, aryl, $C_{3-6}$ cycloalkyl or tetrahydro 2H-pyran-2-yl;

or where $R^1$ is substituted with two -Z-$R^{1-a}$ radicals, the two —$R^{1-a}$ radicals, taken together, may form a bivalent radical of formula —$CH_2$—, —$CH(CH_3)$—, —$C(CH_3)_2$—, —$CH_2$—$CH_2$—, —$CH(CH_3)$—$CH_2$— or —$CH_2$—$CH_2$—$CH_2$—;

X is O, S or $NR^2$;

said $R^2$ being hydrogen or $C_{1-6}$ alkyl;

A is >C=O, $NR^3$ or methylene, optionally substituted with up to two radicals selected from the group consisting of $C_{1-6}$ alkyl and aryl;

said $R^3$ being hydrogen or $C_{1-6}$ alkyl;

B is >C=O or methylene optionally substituted with up to two radicals selected from the group consisting of $C_{1-6}$ alkyl and $C_{1-6}$ alkyloxy;

or A and B, taken together, form a bivalent radical of formula

—N=CH—;      Formula (c)

A' and B' independently having the same meaning of A and B respectively, or A' and B', taken together, form a bivalent radical of formula —N=CH— or      Formula (c)

—CH=CH—;      Formula (d)

wherein the nitrogen atom in the bivalent radical (c) is connected to $NR^1$; wherein one hydrogen in said radical (c) and up to two hydrogens in radical (d) may be replaced by a $C_{1-6}$ alkyl radical; provided that (i) when $Y$—$R^1$ is a radical of formula (a) wherein -A-B- is other than a bivalent radical of formula (c), then $R^1$ is other than $C_{1-6}$ alkyl substituted with $C_{1-6}$ alkyloxy;

(ii) when $Y$—$R^1$ is a radical of formula (b) then $R^1$ is other than $C_{1-6}$ alkyl substituted with $C_{1-6}$ alkyloxy;

wherein aryl is phenyl or substituted phenyl, said substituted phenyl having from 1 to 3 substituents each independently selected from the group consisting of halo, $C_{1-6}$ alkyl, $C_{1-6}$ alkyloxy, nitro, amino and trifluoromethyl, provided that trinitrophenyl is excluded.

In the foregoing definitions the term "halo" is generic to fluoro, chloro, bromo and iodo; the term "$C_{1-6}$ alkyl" is meant to include straight and branched hydrocarbon radicals having from 1 to 6 carbon atoms such as for example, methyl, ethyl, 1-methylethyl, 1,1-dimethylethyl, propyl, 1-methylpropyl, 2-methylpropyl, butyl, pentyl, hexyl and the like; "$C_{3-6}$ cycloalkyl" embraces cyclopropyl, cyclobutyl, cyclopentyl and cyclohexyl.

The compounds of formula (V) may contain in their structure a tautomeric system and consequently these compounds can be present in each of their tautomeric forms.

Compounds within the invention are those wherein $Y$—$R^1$ is a radical of formula (a) or (b), wherein X, A, B, A', B' and $R^1$ are as described hereinabove, provided that A' and B', taken together, do not form a radical of formula (c) or (d).

More specifically, compounds within the invention are those compounds wherein $Y-R^1$ is a radical of formula (a).

Further specific compounds within the invention are those compounds wherein X is 0;

A and B are independently >C=O or methylene, optionally substituted with up to two $C_{1-6}$ alkyl radicals, or A and B, taken together, form a bivalent radical of formula (c) wherein the hydrogen atom may be replaced by a $C_{1-6}$ alkyl radical; and $R^1$ is tetrahydrofuranyl $C_{1-6}$ alkyl, or $C_{3-6}$ cycloalkyl substituted with oxo or hydroxy, or $C_{1-6}$ alkyl or aryl $C_{1-6}$ alkyl both substituted on the $C_{1-6}$ alkyl moiety with oxo or with one or two radicals of formula $-O-R^{1-a}$, or where $R^1$ is substituted with two $-O-R^{1-a}$ radicals, the two $-R^{1-a}$ radicals, taken together, may form a bivalent radical of formula $-C(CH_3)_2-$ or $-CH_2-$.

More specifically, compounds within the invention are those wherein $R^1$ is $C_{3-6}$ cycloalkyl substituted with oxo or hydroxy, or $C_{1-6}$ alkyl or aryl $C_{1-6}$ alkyl both substituted on the $C_{1-6}$ alkyl moiety with oxo or with one or two hydroxy or $C_{1-6}$ alkyloxy radicals.

More specifically, compounds within the invention are those compounds wherein Ar is phenyl substituted with two halo atoms: R is hydrogen: A is $C(CH_3)_2$ or $CH_2$, B is $CH_2$ or >C=O, or A and B, taken together, form a radical (c) wherein the hydrogen atom may be replaced by a methyl radical; and $R^1$ is C 6 alkyl substituted with oxo or hydroxy.

Saperconazole

This invention is further concerned in part with 1H-imidazoles and 1H-1,2,4-triazoles having the formula Formula (VI)

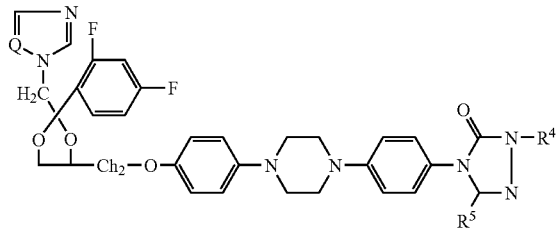

and the stereochemically isomeric forms thereof, wherein

Q is N or CH;

$R^4$ is hydrogen, $C_{1-6}$ alkyl or aryl$C_{1-6}$ alkyl; and $R^5$ is hydrogen, $C_{1-6}$ alkyl or aryl$C_{1-6}$ alkyl;

wherein aryl is phenyl optionally substituted with up to 3 substituents each independently selected from halo, $C_{1-6}$ alkyl, $C_{1-6}$ alkyloxy and trifluoromethyl.

In the foregoing definitions the term "halo" is generic to fluoro, chloro, bromo and iodo and the term "$C_{1-6}$ alkyl" is meant to include straight and branched hydrocarbon radicals having from 1 to 6 carbon atoms such as for example, methyl, ethyl, propyl, 1-methylethyl, 1,1-dimethylethyl, 1-methylpropyl, 2-methylpropyl, butyl, pentyl, hexyl and the like.

The compounds of formula (VI) wherein $R^4$ is hydrogen contain in their structure a tautomeric system and consequently these compounds can be present in each of their tautomeric forms, both of which are intended to be included within the scope of the present invention.

Compounds within the present invention are those compounds of formula (VI) wherein $R^4$ and $R^5$ independently are hydrogen or $C_{1-6}$ alkyl.

More specifically, compounds are the above compounds wherein $R^5$ is hydrogen and $R^4$ is $C_{1-6}$ alkyl.

More specifically, compounds are the above compounds wherein the substituents on the dioxolane moiety have a cis configuration.

A particular subgroup of the compounds of formula (VI) comprises the compounds above Q is nitrogen.

More specific compounds above are selected from the group consisting of cis-4-[4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-(1-methylpropyl)-3H-1,2,4-triazol-3-one and cis-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2-(1,2-dimethylpropyl)-2,4-dihydro-3H-1,2,4-triazol-3-one.

Posaconazole

The present invention provides compounds represented by formula VII

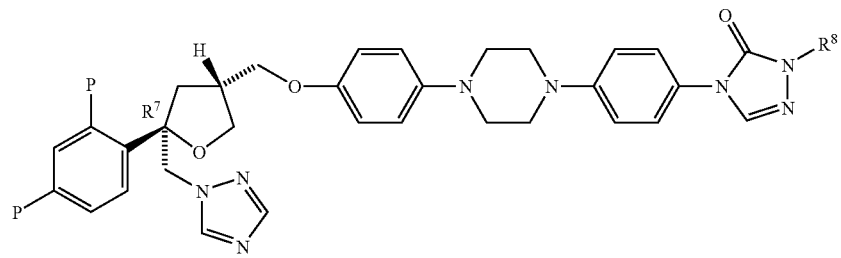

wherein P is independently both F or both Cl or one X is independently F and the other is independently Cl;

$R^8$ is a straight or branched chain ($C_3$ to $C_8$) alkyl group substituted by one or two hydroxy moieties or stereoisomers thereof or by one or two groups convertible in vivo into hydroxy moieties or an ester or ether thereof.

In an aspect of the present invention, there is provided compounds represented by formula VII

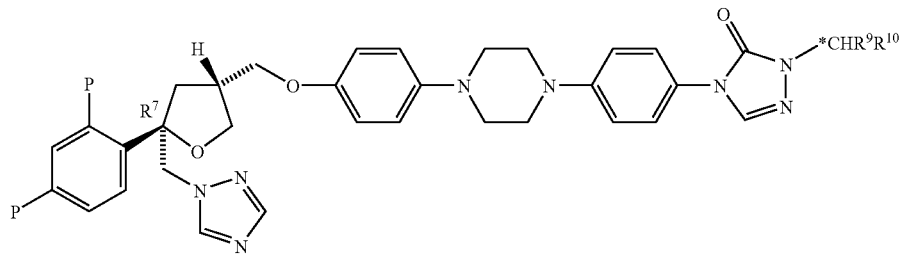

wherein P is independently both F or both Cl or one P is independently F and the other is independently Cl;

wherein $R^9$ is H or ($C_1$-$C_3$) alkyl and $R^{10}$ is ($C_1$-$C_3$) alkyl substituted by one hydroxy moiety or by a group convertible in vivo into a hydroxy moiety and the carbon with the asterisk (*) has the R or S absolute configuration; an ester or ether thereof.

In another aspect, the present invention provides a compound represented by formula V

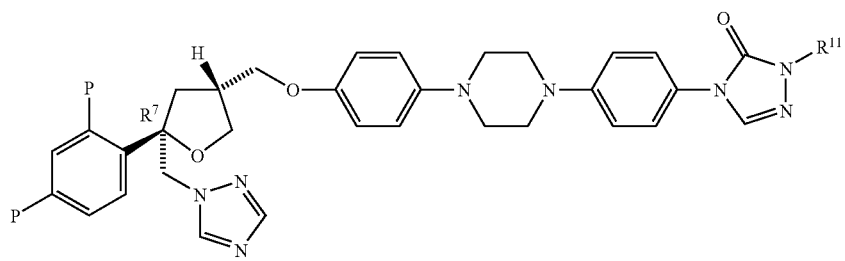

wherein $R^{11}$ is

-continued

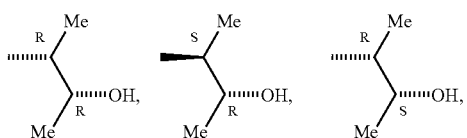

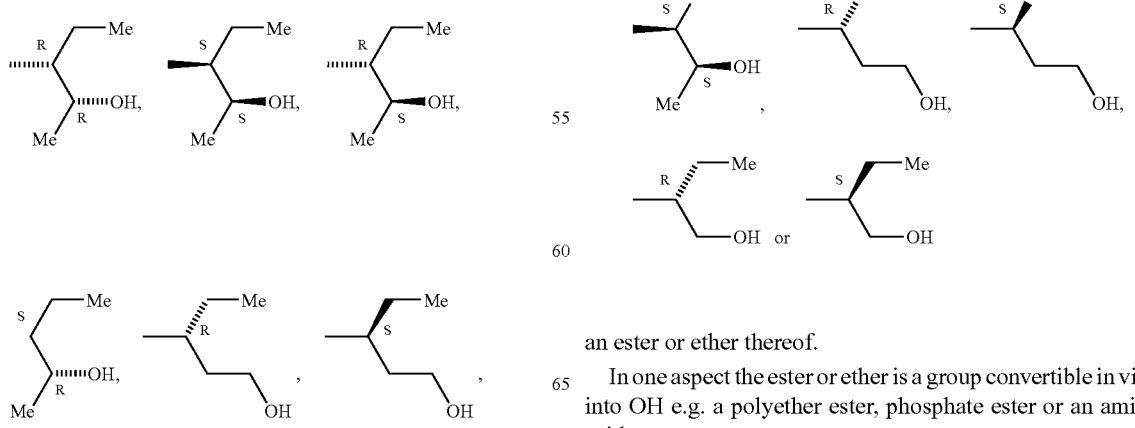

an ester or ether thereof.

In one aspect the ester or ether is a group convertible in vivo into OH e.g. a polyether ester, phosphate ester or an amino acid ester.

In another aspect of the present invention there is provided a compound represent by the formula VI

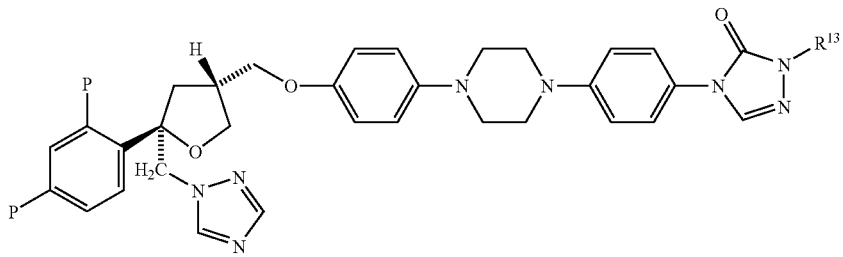

wherein $R^{13}$=—*CH($C_2H_5$)CH($R_{12}$)$CH_3$ or —*CH($CH_3$)CH($R_{12}$)$CH_3$ wherein $R^{12}$ is OH, or a group convertible in vivo into OH.

In certain embodiments, the novel soluble crystalline forms of cis-itraconazole, posaconazole or saperconazole have a solubility greater than 5 mcg/ml, more preferably greater than 10 mcg/ml, more preferably greater than 20 mcg/ml, more preferably greater than 30 mcg/ml, more preferably greater than 40 mcg/ml, more preferably greater than 50 mcg/ml, more preferably greater than 100 mcg/ml, more preferably greater than 1 mg/ml, and more preferably greater than 10 mg/ml in a solution with a pH of about 1.

Preferred novel soluble crystalline forms of cis-itraconazole, posaconazole or saperconazole of the invention include dicarboxylic acid co-crystals of cis-itraconazole, posaconazole or saperconazole such as cis-itraconazole, posaconazole or saperconazole di-mesylate, cis-itraconazole, posaconazole or saperconazole tartaric acid co-crystal, cis-itraconazole, posaconazole or saperconazole fumaric acid co-crystal, itraconazole, posaconazole or saperconazolemalonic acid co-crystal, itraconazole, posaconazole or saperconazolemaleic acid co-crystal, itraconazole, posaconazole or saperconazoleadipic acid co-crystal, cis-itraconazole, posaconazole or saperconazole 1-malic acid co-crystal and cis-itraconazole, posaconazole or saperconazole succinic acid co-crystalic acid co-crystal and salts, co-crystals, hydrates, solvates or polymorphs thereof. Dicarboxylic acid salts and co-crystals of cis-itraconazole, posaconazole or saperconazole include, but are not limited to, cis-itraconazole, posaconazole or saperconazole tartrate, cis-itraconazole, posaconazole or saperconazole succinic acid co-crystal, cis-itraconazole, posaconazole or saperconazole di-mesylate and cis-itraconazole, posaconazole or saperconazole malic acid co-crystal. Other dicarboxylic acid salts and co-crystals of cis-itraconazole, posaconazole or saperconazole are cis-itraconazole, posaconazole or saperconazole fumaric acid co-crystal, cis-itraconazole, posaconazole or saperconazole malonic acid co-crystal, cis-itraconazole, posaconazole or saperconazole adipic acid co-crystal and cis-itraconazole, posaconazole or saperconazole maleic acid co-crystal.

It has surprisingly been found that when an API and a selected co-crystal forming compound are allowed to form co-crystals, the resulting co-crystals give rise to improved properties of the API, as compared to the API in a free form (e.g. free bases, ions, hydrates, solvates, etc.), or an acid salt thereof particularly with respect to: solubility, dissolution, bioavailability, stability, Cmax, Tmax, processability, longer lasting therapeutic plasma concentration, hygroscopicity, crystallization of amorphous compounds, decrease in form diversity (including polymorphism and crystal habit), change in morphology or crystal habit, etc. For example, a co-crystal form of an API is particularly advantageous where the original API, such as the conazoles including cis-itraconazole, posaconazole or saperconazole is insoluble or sparingly soluble in water. Additionally, the co-crystal properties conferred upon the API are also useful because the bioavailability of the API can be improved and the plasma concentration and/or serum concentration of the API can be improved. This is particularly advantageous for orally-administrable formulations. Moreover, the dose response of the API can be improved, for example by increasing the maximum attainable response and/or increasing the potency of the API by increasing the biological activity per dosing equivalent.

Accordingly, in one aspect, the present invention provides a pharmaceutical composition comprising a co-crystal of a conazole including cis-itraconazole, posaconazole or saperconazole and a co-crystal forming compound, such that the conazole and co-crystal forming compound are capable of co-crystallizing from a solution phase under crystallization conditions or from the solid-state through grinding or heating. In another aspect, the conazole has at least one functional group selected from ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, sp2 amine, thiocyanate, cyanamide, oxime, nitrile diazo, organohalide, nitro, s-heterocyclic ring, thiophene, n-heterocyclic ring, pyrrole, o-heterocyclic ring, furan, epoxide, peroxide, hydroxamic acid, imidazole, pyridine and the co-crystal forming compound has at least one functional group selected from amine, amide, pyridine, imidazole, indole, pyrrolidine, carbonyl, carboxyl, hydroxyl, phenol, sulfone, sulfonyl, mercapto and methyl thio, such that the conazole and co-crystal forming compound are capable of co-crystallizing from a solution phase under crystallization conditions.

The co-crystals of the present invention are formed where the conazole and co-crystal forming compound are bonded together through a hydrogen bonds. Other non-covalent interactions, including Π-stacking and van-der-waals interactions, may also be present.

In each process according to the invention, there is a need to contact the conazole with the co-crystal forming compound. This may involve grinding the two solids together or melting one or both components and allowing them to recrystallize. This may also involve either solubilising the conazole and adding the co-crystal forming compound, or solubilising the co-crystal forming compound and adding the conazole. In a preferred arrangement, the conazole may be solubilised in the co-crystal forming compound. Crystallisation conditions are applied to the conazole and co-crystal forming compound. This may entail altering a property of the solution, such as pH or temperature and may require concentration of solute, usually by removal of the solvent, typically by drying the solution. Solvent removal results in the concentration of conazole increasing over time so as to facilitate crystallisation. Once the solid phase comprising any crystals is formed, this may be tested as described herein.

The co-crystals obtained as a result of such process steps may be readily incorporated into a pharmaceutical composition by conventional means. Pharmaceutical compositions in general are discussed in further detail below and may further comprise a pharmaceutically-acceptable diluent, excipient or carrier.

In a further aspect, the present invention provides a process for the production of a pharmaceutical composition, which process comprises:
(1) providing a conazole;
(2) providing a co-crystal forming compound which has at least one functional group selected from amine, amide, pyridine, imidazole, indole, pyrrolidine, carboxyl, carboxyl, hydroxyl, phenol, sulfone, sulfonyl, mercapto and methyl thio;
(3) grinding, heating or contacting in solution the conazole with the co-crystal forming compound under crystallization conditions, and
(4) isolating co-crystals formed thereby; and
(5) incorporating the co-crystals into a pharmaceutical composition.

In a still further aspect the present invention provides a process for the production of a pharmaceutical composition, which comprises:
(1) grinding, heating or contacting in solution a conazole with a co-crystal forming compound, under crystallization conditions, so as to form a solid phase;
(2) isolating co-crystals comprising the conazole and the co-crystal forming compound.

Assaying the solid phase for the presence of co-crystals of the conazole and the co-crystal forming compound may be carried out by conventional methods known in the art. For example, it is convenient and routine to use powder X-ray diffraction techniques to assess the presence of the co-crystals. This may be affected by comparing the diffractograms of the conazole, the crystal forming compound and putative co-crystals in order to establish whether or not true co-crystals had been formed. Other techniques, used in an analogous fashion, include differential scanning calorimetry (DSC), thermogravimetric analysis (TGA) and Raman spectroscopy. Single crystal X-ray diffraction is especially useful in identifying co-crystal structures.

In a further aspect, the present invention therefore provides a process of screening for co-crystal compounds, which comprises:
(1) providing (i) a conazole compound, and (ii) a co-crystal forming compound;
(2) screening for co-crystals of conazoles with co-crystal forming compounds by subjecting each combination of conazole and co-crystal forming compound to a step comprising:
(a) grinding, heating or contacting in solution the conazole with the co-crystal forming compound under crystallization conditions so as to form a solid phase;
(b) isolating co-crystals comprising the conazole and the co-crystal forming compound.

An alternative embodiment is drawn to a process of screening for co-crystal compounds, which comprises:
(1) providing (i) a conazole or a plurality of different conazoles, and (ii) a co-crystal forming compound or a plurality of different co-crystal forming compounds, wherein at least one of the conazole and the co-crystal forming compound is provided as a plurality thereof;
(2) screening for co-crystals of conazoles with co-crystal forming compounds by subjecting each combination of conazole and co-crystal forming compound to a step comprising
(a) grinding, heating or contacting in solution the conazole with the co-crystal forming compound under crystallization conditions so as to form a solid phase;
(b) isolating co-crystals comprising the conazole and the co-crystal forming compound.

Solubility Modulation:

In a further aspect, the present invention provides a process for modulating the solubility of a conazole, which process comprises:
(1) grinding, heating or contacting in solution the conazole with a co-crystal forming compound under crystallization conditions, so as to form a co-crystal of the conazole and the co-crystal forming compound;
(2) isolating co-crystals comprising the conazole and the co-crystal forming compound.

In one embodiment, the solubility of the conazole is modulated such that the aqueous solubility is increased. Solubility of conazoles may be measured by any conventional means such as spectroscopic determination of the amount of conazole in a saturated solution of the conazole, such as UV-spectroscopy, IR-spectroscopy, Raman spectroscopy, quantitative mass spectroscopy or gass chromatography.

In another aspect of the invention, the conazole may have low aqueous solubility. Typically, low aqueous solubility in the present application refers to a compound having a solubility in water which is less than or equal to 10 mg/ml, when measured at 37° C., and preferably less than or equal to 5 mg/ml or 1 mg/ml. "Low aqueous solubility" can further be specifically defined as less than or equal to 900, 800, 700, 600, 500, 400, 300, 200 150 100, 90, 80, 70, 60, 50, 40, 30, 20 micrograms/ml, or further 10, 5 or 1 micrograms/ml. As embodiments of the present invention, solubility can be increased 2, 3, 4, 5, 7, 10, 15, 20, 25, 50, 75, 100, 200, 300, 500, 750, 1000, 5000, or 10,000 times when compared to crystalline free base, by making a co-crystal of the free form or salt. Further aqueous solubility can be measured in simulated gastric fluid (SGF) or simulated intestinal fluid (SIF) rather than water (Dressman J B, et al., Pharm Res. (1998) January; 15(1): 11-22 incorporated by reference in its entirety). SGF (non-diluted) of the present invention is made by combining 1 g/L Triton X-100 and 2 g/L NaCl in water and adjusting the pH with 20 mM HCl to obtain a solution with a final pH=1.7 SIF is 0.68% monobasic potassium phosphate, 1% pancreatin, and sodium hydroxide where the pH of the final solution is 7.5. The pH may also be specified as 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 6, 6.5, 7, 7.5, 8, 8.5, 9, 9.5, 10, 10.5, 11, 11.5, or 12.

Examples of embodiments includes: co-crystal compositions with an aqueous solubility, at 37 degrees C. and a pH of 7.0, that is increased at least 5 fold over the crystalline free form and co-crystal compositions with a solubility in SGF that is increased at least 5 fold over the crystalline free form.

Dissolution Modulation:

In another aspect of the present invention, the dissolution profile of the conazole is modulated whereby the aqueous dissolution rate or the dissolution rate in simulated gastric fluid or in simulated intestinal fluid, or in a solvent or plurality of solvents is increased or decreased. Dissolution rate is the rate at which conazole solids dissolve in a dissolution media.

Conazoles that are not dissolved before they are removed from intestinal absorption site are considered useless. Therefore, the rate of dissolution has a major impact on the performance of conazoles that are poorly soluble. Because of this factor, the dissolution rate of conazoles in solid dosage forms is an important, routine, quality control parameter used in the conazole manufacturing process.

Dissolution rate=$KS(C_s-C)$ where K is dissolution rate constant, S is the surface area, $C_s$ is the apparent solubility, and C is the concentration of conazole in the dissolution media.

The dissolution rate of conazoles may be measured by conventional means known in the art.

The increase in the dissolution rate of a co-crystal, as compared to the crystalline free form, may be specified, such as by 10, 20, 30, 40, 50, 60, 70, 80, 90, or 100%, or by 2, 3, 4, 5, 6, 7, 8, 9, 10, 15, 20, 25, 30, 40, 50, 75, 100, 125, 150, 175, 200 fold greater than the free form or salt form in the same solution. Conditions under which the dissolution rate is measured is the same as discussed above The increase in dissolution may be further specified by the time the composition remains supersaturated.

Examples of above embodiments includes: co-crystal compositions with an dissolution rate, at 37 degrees C. and a pH of 7.0, that is increased at least 5 fold over the crystalline free form and co-crystal compositions with a dissolution rate in SGF that is increased at least 5 fold over the crystalline free form.

Bioavailability Modulation:

The methods of the present invention are used to make a pharmaceutical conazole formulation with greater solubility, dissolution, and bioavailability, AUC, reduced time to $T_{max}$, the time to reach peak blood serum levels, and higher $C_{max}$, the maximum blood serum concentration, when compared to the neutral form or salt alone.

AUC is the area under the plot of plasma concentration of conazole (not logarithm of the concentration) against time after conazole administration. The area is conveniently determined by the "trapezoidal rule": the data points are connected by straight line segments, perpendiculars are erected from the abscissa to each data point, and the sum of the areas of the triangles and trapezoids so constructed is computed. When the last measured concentration ($C_n$, at time $t_n$) is not zero, the AUC from $t_n$ to infinite time is estimated by $C_n/k_{el}$.

The AUC is of particular use in estimating bioavailability of conazoles, and in estimating total clearance of conazoles ($Cl_T$). Following single intravenous doses, AUC=$D/Cl_T$, for single compartment systems obeying first-order elimination kinetics; alternatively, AUC=$C_0/k_{el}$. With routes other than the intravenous, for such systems, AUC=$F·D/Cl_T$, where F is the availability of the conazole.

Thus, in a further aspect, the present invention provides a process for modulating the bioavailability of a conazole when administered in its normal and effective dose range, whereby the AUC is increased, the time to $T_{max}$ is reduced, or $C_{max}$ is increased, which process comprises:
  (1) grinding, heating or contacting in solution the conazole with a co-crystal forming compound under crystallization conditions, so as to form a co-crystal of the conazole and the co-crystal forming compound;
  (2) isolating co-crystals comprising the conazole and the co-crystal forming compound.

Examples of the above embodiments includes: co-crystal compositions with a time to $T_{max}$ that is reduced by at least 10% as compared to the free crystalline form, co-crystal compositions with a time to $T_{max}$ that is reduced by at least 20% over the free crystalline form, co-crystal compositions with a time to $T_{max}$ that is reduced by at least 40% over the free crystalline form, co-crystal compositions with a time to $T_{max}$ that is reduced by at least 50% over the free crystalline form, co-crystal compositions with a $T_{max}$ that is reduced by at least 60% over the free crystalline form, co-crystal compositions with a $T_{max}$ that is reduced by at least 70% over the free crystalline form, co-crystal compositions with a $T_{max}$ that is reduced by at least 80% over the free crystalline form, co-crystal compositions with a $C_{max}$ that is increased by at least 20% over the free crystalline form, co-crystal compositions with a $C_{max}$ that is increased by at least 30% over the free crystalline form, co-crystal compositions with a $C_{max}$ that is increased by at least 40% over the free crystalline form, co-crystal compositions with a $C_{max}$ that is increased by at least 50% over the free crystalline form, co-crystal compositions with a $C_{max}$ that is increased by at least 60% over the free crystalline form, co-crystal compositions with a $C_{max}$ that is increased by at least 70% over the free crystalline form, co-crystal compositions with a $C_{max}$ that is increased by at least 80% over the free crystalline form, co-crystal compositions with an AUC that is increased by at least 10% over the free crystalline form, co-crystal compositions with an AUC that is increased by at least 20% over the free crystalline form, co-crystal compositions with an AUC that is increased by at least 30% over the free crystalline form, co-crystal compositions with an AUC that is increased by at least 40% over the free crystalline form, co-crystal compositions with an AUC that is increased by at least 50% over the free crystalline form, co-crystal compositions with an AUC that is increased by at least 60% over the free crystalline form, co-crystal compositions with an AUC that is increased by at least 70% over the free crystalline form, or co-crystal compositions with an AUC that is increased by at least 80% over the free crystalline form.

Dose Response Modulation:

In a further aspect the present invention provides a process for improving the dose response of a conazole, which process comprises:
  (1) contacting in solution a conazole with a co-crystal forming compound under crystallization conditions, so as to form a co-crystal of the conazole and the co-crystal forming compound;
  (2) isolating co-crystals comprising the conazole and the co-crystal forming compound.

Dose response is the quantitative relationship between the magnitude of response and the dose inducing the response and may be measured by conventional means known in the art. The curve relating effect (as the dependent variable) to dose (as the independent variable) for a conazole-cell system is the "dose-response curve". Typically, the dose-response curve is the measured response to a conazole plotted against the dose of the conazole (mg/kg) given. The dose response curve can also be a curve of AUC against the dose of the conazole given.

Increased Stability:

In a still further aspect the present invention provides a process for improving the stability of a conazole in its free form or a salt thereof, which process comprises:
  (1) Grinding, heating or contacting in solution the pharmaceutical salt with a co-crystal forming compound under crystallization conditions, so as to form a co-crystal of the conazole and the co-crystal forming compound;
  (2) isolating co-crystals comprising the conazole and the co-crystal forming compound.

In a preferred embodiment, the compositions of the present invention, including the conazole or active pharmaceutical ingredient (conazole) and formulations comprising the conazole, are suitably stable for pharmaceutical use. Preferably, the conazole or formulations thereof of the present invention are stable such that when stored at 30 deg. C. for 2 years, less than 0.2% of any one degradant is formed. The term degradant refers herein to product(s) of a single type of chemical reaction. For example, if a hydrolysis event occurs that cleaves a molecule into two products, for the purpose of the present invention, it would be considered a single degradant. More preferably, when stored at 40 deg. C. for 2 years, less than 0.2% of any one degradant is formed. Alternatively, when stored at 30 deg. C. for 3 months, less than 0.2% or 0.15%, or 0.1% of any one degradant is formed, or when stored at 40 deg. C. for 3 months, less than 0.2% or 0.15%, or 0.1% of any one degradant is formed. Further alternatively, when stored at 60 deg. C. for 4 weeks, less than 0.2% or 0.15%, or 0.1% of any one degradant is formed. The relative humidity (RH) may be specified as ambient (RH), 75% (RH), or as any single integer between 1 to 99%.

Difficult to Salt or Unsaltable Compounds:

In a still further aspect the present invention provides a process for making co-crystals of unsaltable conazoles which process comprises (1) Grinding, heating or contacting in solution a conazole with a co-crystal forming compound under crystallization conditions, so as to form a co-crystal of the conazole and the co-crystal forming compound;

(2) isolating co-crystals comprising the conazole and the co-crystal forming compound.

Difficult to salt compounds include bases with a pKa <3 or acids with a pKa >10. Zwitterions are also difficult to salt or unsaltable compounds.

Decreasing Hygroscopicity:

In a still further aspect the present invention provides a method for decreasing the hygroscopicity of a conazole, which method comprises (1) Grinding, heating or contacting in solution the conazole with a co-crystal forming compound under crystallization conditions;

(3) forming a co-crystal of the conazole and the co-crystal forming compound;

(2) isolating co-crystals comprising the conazole and the co-crystal forming compound.

An aspect of the present invention provides a pharmaceutical composition comprising a co-crystal of a conazole that is less hygroscopic than amorphous or crystalline, free form or salt (including metal salts such as sodium, potassium, lithium, calcium, magnesium). Hygroscopicity can be assessed by dynamic vapor sorption analysis, in which 5-50 mg of the compound is suspended from a Cahn microbalance. The compound being analyzed should be placed in a non-hygroscopic pan and its weight should be measured relative to an empty pan composed of identical material and having nearly identical size, shape, and weight. Ideally, platinum pans should be used. The pans should be suspended in a chamber through which a gas, such as air or nitrogen, having a controlled and known percent relative humidity (% RH) is flowed until eqilibrium criteria are met. Typical equilibrium criteria include weight changes of less than 0.01% change over 3 minutes at constant humidity and temperature. The relative humidity should be measured for samples dried under dry nitrogen to constant weight (<0.01% change in 3 minutes) at 40 degrees C. unless doing so would de-solvate or otherwise convert the material to an amorphous compound. In one aspect, the hygroscopicity of a dried compound can be assessed by increasing the RH from 5 to 95% in increments of 5% RH and then decreasing the RH from 95 to 5% in 5% increments to generate a moisture sorption isotherm. The sample weight should be allowed to equilibrate between each change in % RH. If the compound deliquesces or becomes amorphous between above 75% RH, but below 95% RH, the experiment should be repeated with a fresh sample and the relative humidity range for the cycling should be narrowed to 5-75% RH or 10-75% RH instead of 5-95% RH. If the sample cannot be dried prior to testing due to lack of form stability, than the sample should be studied using two complete humidity cycles of either 10-75% RH or 5-95% RH, and the results of the second cycle should be used if there is significant weight loss at the end of the first cycle.

Hygroscopicity can be defined using various parameters. For purposes of the present invention, a non-hygroscopic molecule should not gain or lose more than 1.0%, or more preferably, 0.5% weight at 25 degrees C. when cycled between 10 and 75% RH (relative humidity at 25 degrees C.). The non-hygroscopic molecule more preferably should not gain or lose more than 1.0%, or more preferably, 0.5% weight when cycled between 5 and 95% RH at 25 degrees C., or more than 0.25% of its weight between 10 and 75% RH. Most preferably, a non-hygroscopic molecule will not gain or lose more than 0.25% of its weight when cycled between 5 and 95% RH.

Alternatively, for purposes of the present invention, hygroscopicity can be defined using the parameters of Callaghan et al., Equilibrium moisture content of pharmaceutical excipients, in Conazole Dev. Ind. Pharm., Vol. 8, pp. 335-369 (1982). Callaghan et al. classified the degree of hygroscopicity into four classes.

| | |
|---|---|
| Class 1: Non-hygroscopic | Essentially no moisture increases occur at relative humidities below 90%. |
| Class 2: Slightly hygroscopic | Essentially no moisture increases occur at relative humidities below 80%. |
| Class 3: Moderately hygroscopic | Moisture content does not increase more than 5% after storage for 1 week at relative humidities below 60%. |
| Class 4: Very hygroscopic | Moisture content increase may occur at relative humidities as low as 40 to 50%. |

Alternatively, for purposes of the present invention, hygroscopicity can be defined using the parameters of the European Pharmacopoeia Technical Guide (1999, p. 86) which has defined hygrospocity, based on the static method, after storage at 25° C. for 24 h at 80 percent RH:

Slightly hygroscopic: Increase in mass is less than 2 percent m/m and equal to or greater than 0.2 percent m/m.

Hygroscopic: Increase in mass is less than 15 percent m/m and equal to or greater than 0.2 percent m/m.

Very Hygroscopic: Increase in mass is equal to or greater than 15 percent m/m.

Deliquescent: Sufficient water is absorbed to form a liquid.

Co-crystals of the present invention can be set forth as being in Class 1, Class 2, or Class 3, or as being Slightly hygroscopic, Hygroscopic, or Very Hygroscopic. Co-crystals of the present invention can also be set forth based on their ability to reduce hygroscopicity. Thus, preferred co-crystals of the present invention are less hygroscopic than the conazole. The reference compound can be specified as the conazole in free form (free acid, free base, hydrate, solvate, etc.) or salt (e.g., metal salt such as sodium, potassium, lithium, calcium, or magnesium). Further included in the present invention are co-crystals that do not gain or lose more than 1.0% weight at 25 degrees C. when cycled between 10 and 75% RH, wherein the reference compound gains or loses more than 1.0% weight under the same conditions. Further included in the present invention are co-crystals that do not gain or lose more than 0.5% weight at 25 degrees C. when cycled between 10 and 75% RH, wherein the reference compound gains or loses more than 0.5% or more than 1.0% weight under the same conditions. Further included in the present invention are co-crystals that do not gain or lose more than 1.0% weight at 25 degrees C. when cycled between 5 and 95% RH, wherein the reference compound gains or loses more than 1.0% weight under the same conditions. Further included in the present invention are co-crystals that do not gain or lose more than 0.5% weight at 25 degrees C. when cycled between 5 and 95% RH, wherein the reference compound gains or loses more than 0.5% or more than 1.0% weight under the same conditions. Further included in the present invention are co-crystals that do not gain or lose more than 0.25% weight at 25 degrees C. when cycled between 5 and 95% RH, wherein the reference compound gains or loses more than 0.5% or more than 1.0% weight under the same conditions.

Further included in the present invention are co-crystals that have a hygroscopicity (according to Callaghan et al.) that is at least one class lower than the reference compound or at least two classes lower than the reference compound. Included are a Class 1 co-crystals of a Class 2 reference compound, a Class 2 co-crystals of a Class 3 reference compound, a Class 3 co-crystals of a Class 4 reference compound, a Class 1 co-crystals of a Class 3 reference compound, a Class 1 co-crystals of a Class 4 reference compound, or a Class 2 co-crystals of a Class 4 reference compound.

Further included in the present invention are co-crystals that have a hygroscopicity (according to the European Pharmacopoeia Technical Guide) that is at least one class lower than the reference compound or at least two classes lower than the reference compound. Non-limiting examples include; a Slightly hygroscopic co-crystals of a Hygroscopic reference compound, a Hygroscopic co-crystals of a Very Hygroscopic reference compound, a Very Hygroscopic co-crystals of a Deliquescent reference compound, a Slightly hygroscopic co-crystals of a Very Hygroscopic reference compound, a Slightly hygroscopic co-crystals of a Deliquescent reference compound, a Hygroscopic co-crystals of a Deliquescent reference compound.

In one aspect, the present invention demonstrates that crystalline phases can be engineered by combining molecules selected to match hydrogen bond donors with acceptors and by considering structural complementarities. The present invention further shows that supramolecular synthesis can be applied to active pharmaceutical ingredients using organic acid and base combinations with $pK_a$ differences that are inconsistent with salt formation in water (given the $pK_a$ value of 3.7 for the piperazine of itraconazole, conventional wisdom would limit a salt screen to those strong acids having dissociation constants below 1.7).

Figure 6:
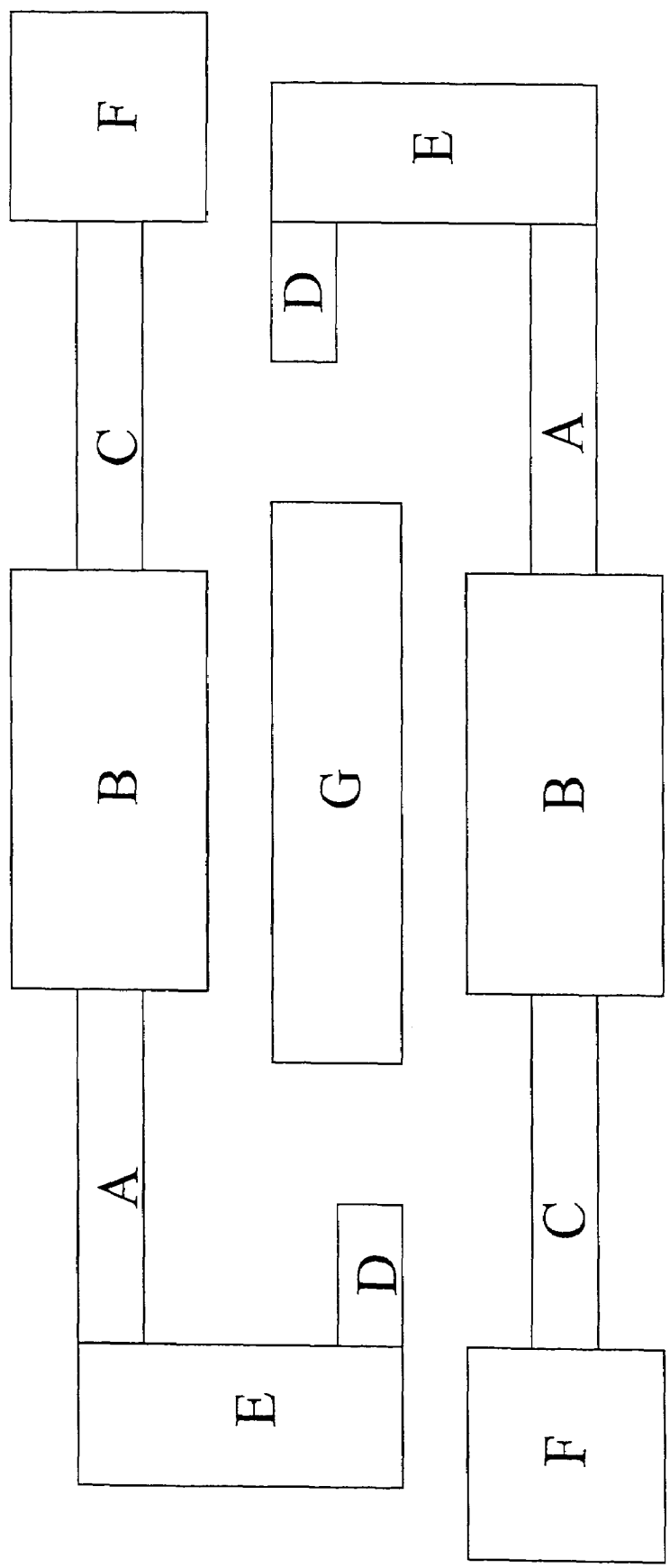
FIG. 6 shows a schematic of a conazole co-crystal comprising a trimer consisting of a co-crystal former sandwiched between two antiparallel conazole molecules.

An aspect of the present invention includes co-crystals comprising or consisting of hydrogen-bonded trimers consisting of two molecules of cis-itraconazole (or two molecules of posaconazole or two molecules of saperconazole) and one molecule of a dicarboxylic acid (e.g., succinic acid). Preferred dicarboxylic acid co-crystals of cis-itraconazole, posaconazole or saperconazole have a crystal structure as shown in FIG. 6. The drug molecule (see FIG. 6) is composed of a three ring backbone (A-C), a triazole ring (D), a spacer group (E) and a terminating group (F). The trimer has two drug molecules oriented anti-parallel to each other with a second molecule, a dicarboxylic acid, (G) templating or filling the void between the two drug molecules. The distance between the carboxylic acid oxygen (—O(H)), one of the possible function groups of molecule G, and the tirazole nitrogen (—N—), D, can be between 3.4 and 1.8 angstroms, more preferably between 3.2 and 2.3 angstroms, still more preferably between 3.0 and 2.5 angstroms and more preferable still between 2.8 and 2.6 angstroms. The distance between the two drug molecules that make up the trimer, as measured by the distance between a nitrogen atom in ring A of one molecule and ring A of the second molecule can be between about 7.5 and about 6.4 angstroms, more preferably between about 7.0 and about 6.6 angstroms and still more preferably about 6.8 angstroms. The distance between the two triazole rings (D) in the trimer, as measured by the shortest distance between two nitrogen atoms, with one each separate molecule, can be between about 12.5 and about 8.0 angstroms, more prefereably between about 11 and about 10.6 angstroms and still more preferably about 10.8 angstroms. The trimer can also, in some cases, be defined further by being oriented around a center of inversion located at the center of molecule G. The dicarboxylic acid that is used to fill the pocket of the trimer (succininc acid in the model shown) can be for example, fumaric acid, succinic acid, tartaric acid, DL-tartaric acid, D-tartaric acid, L-tartaric acid, meso-tartaric acid, d-malic acid, L-malic acid, DL-malic acid, malonic, glutaric acid, adipic acid or acetic acid. The crystal structure of one congener (FIG. 7 for itraconazole (actual), FIG. 8 for posaconazole (proposed) and FIG. 9 for saperconazole (proposed)) reveals an unanticipated and specific interaction between the triazole of the conazole and the diacid in the solid state (the solid grey atoms are carbon, the open atoms are hydrogens, the small dots (or light gray) are nitrogen atoms the large dots (black and white) are oxygen and the other atoms (hatched) are either chlorine or fluorine, depending on the compound.

Particularly preferred pharmaceutical compositions of the invention comprise a therapeutically effective amount of an acid salt, co-crystal, solvate, hydrate, or multicomponent crystalline system such as cis-itraconazole, posaconazole or saperconazole HCl salt tartaric acid co-crystal, or a soluble, multicomponent crystalline system comprising cis-itraconazole, posaconazole or saperconazole di-mesylate and ethanol, or a soluble, multicomponent crystalline system comprising cis-itraconazole, posaconazole or saperconazole di-mesylate and dioxane.

In another embodiment, the present invention provides a soluble crystalline form or a formulation of a soluble crystalline form of a conazole with a decreased food effect. In a specific embodiment, a soluble crystalline form or a formulation of a soluble crystalline form of itraconazole is provided which has a decreased food effect with respect to that of a reference form (e.g., itraconazole free base, a salt of itraconazole, or a polymorph, hydrate solvate, or co-crystal thereof) or a reference formulation (e.g., Sporanox®).

In another embodiment, the present invention provides a method for decreasing the food effect of a conazole. A method for decreasing the food effect of a conazole is provided, comprising administering to a mammal a soluble crystalline form or a formulation of a soluble crystalline form of the present invention. For example, a method for decreasing the food effect of itraconazole comprises administering to a mammal a soluble crystalline form or a formulation of a soluble crystalline form of the present invention such as, but not limited to, itraconazole HCl:DL-tartaric acid co-crystal. The decrease in food effect discussed in the above methods can be measured with respect to the food effect observed from a reference form (e.g., itraconazole free base, a salt of itraconazole, or a polymorph, hydrate solvate, or co-crystal thereof) or a reference formulation (e.g., Sporanox®).

A further embodiment of the invention encompasses a method of treating or preventing local or systemic fungal, yeast, and dermatophyte infections in a patient which comprises administering to a patient in need of such treatment or prevention a therapeutically or prophylactically effective amount of a pharmaceutically acceptable soluble crystalline form of a conazole (including cis-itraconazole, posaconazole or saperconazole), including salts, co-crystals, salt co-crystals and hydrates, solvates or polymorphs thereof. More specifically, the invention includes a method for treating or preventing local and systemic fungal, yeast, and dermatophyte infections in a patient comprising administering to a patient in need of such treatment or prevention, a therapeutically or prophylactically effective amount of a composition of the present invention including a salt or co-crystal of cis-itraconazole, posaconazole or saperconazole such as cis-itraconazole, posaconazole or saperconazole di-mesylate, cis-itraconazole, posaconazole or saperconazole tartaric acid co-crystal, cis-itraconazole, posaconazole or saperconazole fumaric acid co-crystal, cis-itraconazole, posaconazole or saperconazole malonic acid co-crystal, cis-itraconazole, posaconazole or saperconazole maleic acid co-crystal, cis-itraconazole, posaconazole or saperconazole adipic acid co-crystal, cis-itraconazole, posaconazole or saperconazole malic acid co-crystal or cis-itraconazole, posaconazole or saperconazole succinic acid co-crystal.

The invention further encompasses the use of a dicarboxylic acid salt or co-crystal of cis-itraconazole, posaconazole or saperconazole. Methods of treatment include administration of pharmaceutical compositions of the invention comprising a therapeutically effective amount of an acid salt cis-itraconazole, posaconazole or saperconazole HCl salt tartaric acid co-crystal, or a soluble, multicomponent crystalline system comprising cis-itraconazole, posaconazole or saperconazole di-mesylate and ethanol, or a soluble, multicomponent crystalline system comprising cis-itraconazole, posaconazole or saperconazole di-mesylate and dioxane.

Pharmaceutical Compositions and Dosage Forms

Pharmaceutical dosage forms of the invention comprise a therapeutically or prophylactically effective amount of a novel soluble crystalline form of cis-itraconazole, posaconazole or saperconazole, including hydrates, solvates or polymorphs thereof. These dosage forms also comprise a soluble, multicomponent crystalline system comprising cis-itraconazole, posaconazole or saperconazole organic salt and an organic solvent. These compositions can be administered orally, parenterally, by inhalation spray, topically, rectally, nasally, buccally, vaginally or via an implanted reservoir. Oral pharmaceutical compositions and dosage forms are a preferred dosage form. Preferably, the oral dosage form is a solid dosage form, such as a tablet, a caplet, a hard gelatin capsule, a starch capsule, a hydroxypropyl methylcellulose ("HPMC") capsule, or a soft elastic gelatin capsule. Other preferred dosage forms include an intradermal dosage form, an intramuscular dosage form, a subcutaneous dosage form, and an intravenous dosage form.

Pharmaceutical compositions and dosage forms of the invention comprise an active ingredient as disclosed herein, e.g., an acid salt cis-itraconazole, posaconazole or saperconazole HCl salt tartaric acid co-crystal or a soluble, multicomponent crystalline system comprising cis-itraconazole, posaconazole or saperconazole organic salt and an organic solvent. Pharmaceutical compositions and unit dosage forms of the invention typically also comprise one or more pharmaceutically acceptable excipients or diluents. In one embodiment, the pharmaceutical compositions and unit dosage forms of the invention typically also comprise one or more pharmaceutically acceptable excipients or diluents, wherein at least one of the pharmaceutically acceptable excipients or diluents is an antioxidant.

Pharmaceutical unit dosage forms of this invention are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: tablets; caplets; capsules, such as hard gelatin capsules, starch capsules, hydroxypropyl methylcellulose ("HPMC") capsules, and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease or disorder may contain larger amounts of the active ingredient than a dosage form used in the chronic treatment of the same disease or disorder. Similarly, a parenteral dosage form may contain smaller amounts of the active ingredient than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990) or *Remington: The Science and Practice of Pharmacy*, 19th ed., Mack Publishing, Easton Pa. (1995).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. In addition, pharmaceutical compositions or dosage forms may contain one or more compounds that reduce or alter the rate by which the active ingredient will decompose. Such compounds, which are referred to herein as "stabilizers", include, but are not limited to, antioxidants, pH buffers, or salt buffers.

One or more antioxidants can be used in pharmaceutical compositions and dosage forms to deter radical oxidation of the active ingredient, wherein such antioxidants include, but are not limited to, ascorbic acid, phenolic antioxidants including, but not limited to, butylated hydroxyanisole (BHA) and propyl gallate, and chelators including, but not limited to citrate, EDTA, and DTPA. Preferably, in cases where radical oxidation of the active ingredient is known to occur, a combination of phenolic antioxidants and chelators can be used.

Like the amounts and types of excipients, the amounts and specific type of active ingredient in a dosage form may differ depending on factors such as, but not limited to, the route by which it is to be administered to patients. However, typical dosage forms of the invention comprise a pharmaceutically acceptable salt and co-crystal of cis-itraconazole, posaconazole or saperconazole or its stereoisomers, selected from the group consisting of cis-itraconazole, posaconazole or saperconazole malic acid co-crystal and cis-itraconazole, posaconazole or saperconazole-HCl, and pharmaceutically acceptable hydrates, solvates, polymorphs, and co-crystals thereof, in an amount of from about 10 mg to about 1000 mg, preferably in an amount of from about 25 mg to about 500 mg, more preferably in an amount of from 40 mg to 400 mg, and most preferably in an amount of from about 50 mg to about 200 mg.

Oral Dosage Forms

Pharmaceutical compositions of the invention that are suitable for oral administration can be presented as discrete dosage forms, such as, but not limited to, tablets (including without limitation scored or coated tablets), pills, caplets, capsules (including without limitation hard gelatin capsules, starch capsules, HPMC capsules, and soft elastic gelatin capsules), chewable tablets, powder packets, sachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the active ingredient, and may be prepared by methods of pharmacy well known to those skilled in the art. See generally, *Remington's Pharmaceutical Sciences,* 18th ed., Mack Publishing, Easton Pa. (1990) or *Remington: The Science and Practice of Pharmacy,* 19th ed., Mack Publishing, Easton Pa. (1995).

Typical oral dosage forms of the invention are prepared by combining the active ingredient in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, stabilizers, and disintegrating agents.

Due to their ease of administration, tablets, caplets, and capsules (such as hard gelatin, HPMC, or starch capsules) represent the most advantageous solid oral dosage unit forms, in which case solid pharmaceutical excipients are used. If desired, tablets or caplets can be coated by standard aqueous or nonaqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary.

For example, a tablet can be prepared by compression or molding. Compressed tablets can be prepared by compressing in a suitable machine the active ingredient(s) in a free-flowing form, such as a powder or granules, optionally mixed with one or more excipients. Molded tablets can be made by molding in a suitable machine a mixture of the powdered compound moistened with an inert liquid diluent.

Examples of excipients that can be used in oral dosage forms of the invention include, but are not limited to, binders, stabilizers, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103, AVICEL RC-581, and AVICEL-PH-105 (available from FMC Corporation, American Viscose Division, Avicel Sales, Marcus Hook, Pa., U.S.A.), and mixtures thereof. An exemplary suitable binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants can be used in the pharmaceutical compositions and dosage forms to provide tablets or caplets that disintegrate when exposed to an aqueous environment. Tablets or caplets that contain too much disintegrant may disintegrate in storage, while those that contain too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form solid oral dosage forms of the invention. The amount of disintegrant used varies based upon the type of formulation and mode of administration, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Antioxidants can be used in the pharmaceutical compositions and dosage forms to deter degradation or radical oxidation of the active ingredient. Examples of suitable antioxidants include, but are not limited to, ascorbic acid, phenolic antioxidants including, but not limited to, butylated hydroxyanisole (BHA) and propyl gallate, and chelators including, but not limited to, citrate, EDTA, and DTPA, or combinations thereof.

Lubricants that can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Other oral dosage forms for pharmaceutical compositions of the invention are soft elastic gelatin capsules. Soft elastic gelatin capsule unit dosage forms can be made using conventional methods well known in the art. See, e.g., Ebert, *Pharm. Tech,* 1(5):44-50 (1977). In general, soft elastic gelatin capsules (also known as "soft gels") have an elastic or soft, globular or oval shaped gelatin shell that is typically a bit thicker than that of hard gelatin capsules, wherein a plasticizing agent, e.g., glycerin, sorbitol, or a similar polyol, is added to a gelatin. The type of gelatin, as well as the amounts of plasticizer and water, can be used to vary the hardness of the capsule shell. The soft gelatin shells may contain a preservative, such as methyl- and propylparabens and sorbic acid, to prevent the growth of fungi. The active ingredient may be dissolved or suspended in a liquid vehicle or carrier, such as vegetable or mineral oils, glycols, such as polyethylene glycol and propylene glycol, triglycerides, surfactants, such as polysorbates, or a combination thereof.

Delayed Release Dosage Forms

Active ingredients of the invention can be administered by controlled or delayed release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566; each of which is incorporated herein by reference in its entirety. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof, to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, pills, capsules, gelcaps, and caplets, that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the disease or condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or can also be stimulated by compounds.

Alternatively, controlled-release pharmaceutical products can be designed to also initially release one or more additional active ingredients (such as a metabolic inhibitor) that can effect characteristics of the other active ingredient (such as cis-itraconazole, posaconazole or saperconazole malic acid co-crystal and cis-itraconazole, posaconazole or saperconazole-HCl, or a hydrate, solvate, polymorph, or co-crystal thereof). For example, a metabolic inhibitor, such as a CYP3A4 inhibitor can be used to inhibit first-pass hepatic metabolism of the active ingredient.

Topical Dosage Forms

Topical dosage forms of the invention include, but are not limited to, creams, lotions, ointments, gels, shampoos, sprays, aerosols, solutions, emulsions, and other forms know to one of skill in the art. See, e.g., *Remington 's Pharmaceutical Sciences,* 18$^{th}$ ed., Mack Publishing, Easton, Pa. (1990); and *Introduction to Pharmaceutical Dosage Forms,* 4$^{th}$ ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., *Remington's Pharmaceutical Sciences,* 18$^{th}$ ed., Mack Publishing, Easton, Pa. (1990).

Parenteral Dosage Forms

Parenteral dosage forms can be administered to patients by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, without limitation: sterile water; Water for Injection USP; saline solution; glucose solution; aqueous vehicles such as but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and propylene glycol; and nonaqueous vehicles such as, but not limited to, corn oil, cottonseed oil, peanut oil, sesame oil, ethyl oleate, isopropyl myristate, and benzyl benzoate. The solutions are preferably isotonic and have a physiological pH.

Compounds that increase the solubility the active ingredient(s) disclosed herein can also be incorporated into the parenteral dosage forms of the invention.

Transdermal and Mucosal Dosage Forms

Transdermal and mucosal dosage forms of the invention include, but are not limited to, ophthalmic solutions, patches, sprays, aerosols, creams, lotions, suppositories, ointments, gels, solutions, emulsions, suspensions, or other forms know to one of skill in the art. See, e.g., *Remington's Pharmaceutical Sciences,* 18<sup>th</sup> ed., Mack Publishing, Easton, Pa. (1990); and *Introduction to Pharmaceutical Dosage Forms,* 4<sup>th</sup> ed., Lea & Febiger, Philadelphia, Pa. (1985). Dosage forms suitable for treating mucosal tissues within the oral cavity can be formulated as mouthwashes, as oral gels, or as buccal patches. Further, transdermal dosage forms include "reservoir type" or "matrix type" patches, which can be applied to the skin and worn for a specific period of time to permit the penetration of a desired amount of active ingredient.

Suitable excipients (e.g., carriers and diluents) and other materials that can be used to provide transdermal and mucosal dosage forms encompassed by this invention are well known to those skilled in the pharmaceutical arts, and depend on the particular tissue or organ to which a given pharmaceutical composition or dosage form will be applied. With that fact in mind, typical excipients include, but are not limited to water, acetone, ethanol, ethylene glycol, propylene glycol, butane-1,3-diol, isopropyl myristate, isopropyl palmitate, mineral oil, and mixtures thereof, to form dosage forms that are nontoxic and pharmaceutically acceptable.

Depending on the specific tissue to be treated, additional components may be used prior to, in conjunction with, or subsequent to treatment with active ingredients of the invention. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, solvates, polymorphs, or co-crystals of the active ingredient can be used to further adjust the properties of the resulting composition.

Methods Of Treatment and Prevention

Pharmaceutically acceptable salts and co-crystals of cis-itraconazole, posaconazole or saperconazole, and pharmaceutical compositions and dosage forms thereof, possess potent activity against and are useful for treating or preventing local and systemic fungal, yeast, and dermatophyte infections. For example, pharmaceutically acceptable soluble crystalline form of cis-itraconazole, posaconazole or saperconazole, and pharmaceutical compositions and dosage forms thereof, can be used to treat or prevent blastomycosis, aspergillosis, histoplasmosis, onychomycosis, coccidioidomycosis, paracoccidioidomycosis, cryptococcosis, dermatophyte, and candidiasis infections.

The magnitude of a prophylactic or therapeutic dose of each active ingredient in the acute or chronic management of a disease or disorder will vary with the disease or disorder itself, the specific active ingredients, and the route of administration. The dose, dose frequency, or both, may also vary according to age, body weight, response, the past medical history of the patient, and consideration of whether the patient is or will be concurrently or concomitantly taking other drugs or pharmaceuticals. Suitable dosing regimens can be readily selected by the skilled artisan with due consideration of such factors by following, for example, dosages and dose regimens reported in the literature and recommended in the *Physician's Desk References*® (56<sup>th</sup> ed., 2002) for itraconazole or saperconazole; which can be extended for determining dosing of posaconazole. Unless otherwise indicated, the magnitude of a prophylactic or therapeutic dose of the active ingredient used in an embodiment of the invention will be that which is safe and effective (e.g., has received regulatory approval).

In one embodiment of the invention, the active ingredient (e.g., soluble crystalline forms of cis-itraconazole, posaconazole or sap erconazole di-mesylate, cis-itraconazole, posaconazole or saperconazole tartrate, cis-itraconazole, posaconazole or saperconazole fumaric acid co-crystal, cis-itraconazole, posaconazole or saperconazole malonic acid co-crystal, cis-itraconazole, posaconazole or saperconazole maleic acid co-crystal, cis-itraconazole, posaconazole or saperconazole adipic acid co-crystal, cis-itraconazole, posaconazole or saperconazole malic acid co-crystal, cis-itraconazole, posaconazole or saperconazole succinic acid co-crystal, cis-itraconazole, posaconazole or saperconazole-HCl, cis-itraconazole, posaconazole or saperconazole phosphate, cis-itraconazole, posaconazole or saperconazole sulfate or cis-itraconazole, posaconazole or saperconazole benzenesulfonate, or multicomponent crystalline systems, hydrates, solvates, polymorphs, or co-crystals thereof) is administered orally as needed in an amount of from about 10 mg to about 1000 mg, preferably in an amount of from about 25 mg to about 500 mg, more preferably in an amount from about 40 mg to about 400 mg, and most preferably in an amount of from about 50 mg to about 200 mg. The dosage amounts can be administered in single or divided doses. The dosage amounts and frequencies provided above are encompassed by the terms "therapeutically effective", "prophylactically effective", and "therapeutically or prophylactically effective" as used herein.

The suitability of a particular route of administration employed for a particular active ingredient will depend on the active ingredient itself (e.g., whether it can be administered orally without decomposing prior to entering the blood stream) and the disease or disorder to be treated or prevented. For example, topical administration is typically preferred for treating or preventing local diseases or disorders of the skin, while oral or parenteral administration is typically preferred for systemic diseases or disorders, or diseases or disorders within the body of the patient. Similarly, oral or parenteral administration may be preferred for the treatment or prevention of acute diseases or disorders, whereas transdermal or subcutaneous routes of administration may be employed for treatment or prevention of a chronic disease or disorder.

Preparation of Soluble Crystalline Forms of Cis-Itraconazole, Posaconazole or Saperconazole Soluble crystalline form of cis-itraconazole, posaconazole or saperconazole can be made using various methods known to those skilled in the art. For example, methods for the chemical synthesis of (±)cis-itraconazole are described in U.S. Pat. No. 4,267,179 and Heeres, J. et al., *J. Med. Chem.*, 27:894-900 (1984), both of which are incorporated by reference herein in their entirety. The four individual stereoisomeric forms of the compounds of formula (I), or diastereomeric pairs or mixtures thereof, can be prepared and purified using various methods known to those skilled in the art, such as those described in U.S. Pat. No. 5,998,413 and U.S. Pat. No. 5,474,997, both of which are specifically incorporated herein by reference in their entirety.

Salts and co-crystals of cis-itraconazole, posaconazole or saperconazole, include without limitation, pharmaceutically acceptable salts prepared by treating cis-itraconazole, posaconazole or saperconazole free base with appropriate acids, such as organic or inorganic acids, including without limitation, malic acid, hydrochloric acid, sulfuric acid, fumaric acid, phosphoric acid, tartaric acid, maleic acid, malonic acid, adipic acid, benzenesulfonic acid, and the like. For example, the process for forming a salt or co-crystal can be carried out in a solvent system in which both reactants (i.e., a conazole such as cis-itraconazole, posaconazole or saperconazole free base and the respective acid) are sufficiently soluble. In one method, in order to achieve crystallization or precipitation, a solvent or solvent mixture in which the resulting salt and co-crystal is only slightly soluble or not soluble at all is used. Alternatively, a solvent in which the desired salt and co-crystal is very soluble can be used, and then an anti-solvent (or a solvent in which the resulting salt is poorly soluble) is added to the solution. Other variants for salt formation or crystallization includes concentrating the salt and co-crystal solution (e.g., by heating, under reduced pressure if necessary, or by slowly evaporating the solvent, for example, at room temperature), or seeding with the addition of seed crystals, or setting up water activity required for hydrate formation. In a preferred method, cis-itraconazole, posaconazole or saperconazole and a dicarboxylic acid (e.g., a dicarboxylic acid of formula (IV)) are dissolved in THF at greater than 60° C., cooled to room temperature and seeded with cis-itraconazole, posaconazole or saperconazole-L-tartrate. Specific examples of the preparation of cis-itraconazole salts and co-crystals can be found below.

The invention is further defined by reference to the following examples. It will be apparent to those skilled in the art that many modifications, both to materials and methods, can be practiced without departing from the scope of this invention.

EXAMPLES

Example 1

Synthesis and Analysis of Cis-Itraconazole Sulfate, Fumaric Acid Co-Crystal, Phosphate, Besylate, Fumaric Acid Co-Crystal, and DL-Tartaric Acid Co-Crystal Synthesis of Cis-Itraconazole Salts and Co-Crystals A stock solution of (±)cis-itraconazole free base was prepared by weighing out 3.750 grams of (±)cis-itraconazole free base (Lot # KEO 0026, Química Sinética S.A) into a 250 mL volumetric flask. The flask was filled with tetrahydrofuran ("THF") (Lot # 50K1485, Sigma Chemicals Co., St. Louis, Mo. USA), and the solid was dissolved with stirring.

In order to form the phosphate, sulfate, fumaric acid co-crystal besylate salts and the fumaric acid and DL-tartaric acid co-crystals of cis-itraconazole, the following salt former and co-crystal former stock solutions were prepared:

TABLE 1

| Salt or Co-Crystal Former (SF) | Total Volume of Solution | Amount Used | Concentration of SF |
|---|---|---|---|
| DL-Tartaric Acid | 50 ml (50:50 THF/$H_2O$) | 1.4 g | 28 mg/ml |
| Phosphoric Acid, 85% pure | 50 ml | 0.980392 ml | 28 mg/ml |
| Sulfuric Acid, 98% pure | 50 ml | 0.761 ml | 28 mg/ml |
| Fumaric Acid | 50 ml | 1.4 g | 28 mg/ml |
| Benzenesulfonic Acid | 50 ml | 1.4 g | 28 mg/ml |

Each of five 20 ml screw cap scintillation vials having Teflon tape around the threads at the top of the vial was filled with 10 mL of (±)cis-itraconazole/THF stock solution (15 mg/mL).

To prepare cis-itraconazole DL-tartaric acid co-crystal, in vial 1, 1198.3 μl of tartaric acid stock solution was added and the vial was capped. To prepare cis-itraconazole phosphate, in vial 2, 782.6 μl of phosphoric acid stock solution was added and the vial was capped. To prepare cis-itraconazole sulfate, in vial 3, 782.5 μl of sulfuric acid stock solution was added and the vial was capped. To prepare cis-itraconazole fumaric acid co-crystal, in vial 4, 926.6 μl of fumaric acid stock solution was added and the vial was capped. And to prepare cis-itraconazole benzenesulfonate (besylate), in vial 5, 1262.0 μl of benzenesulfonic acid stock solution was added and the vial was capped.

All five vials were then placed into a 70° C. oven (VWR Scientific, Model # 1400E), and after 5 minutes in the oven, the caps on all the vials were re-tightened to prevent evaporation. The vials were then left in the oven for one hour.

Thereafter, the vials were removed from the oven, the caps from all the bottles were removed, and the samples were allowed to evaporate in air under ambient conditions. Once significant amounts of solids were present in a sample, the remaining liquid in the sample was removed by pipetting out the liquid phase and using suction filtration with Whatman filter paper to rescue any solid that may have been dispersed in the liquid phase. The remaining solid in the liquid phase and the filtrate were dried in the vacuum oven (VWR Scientific, Model # 1400E) under vacuum for at least 12 hours. With regard to vial 3, the solid crashed out of solution as soon as the acid was added and never went into solution even at 70° C.; however, the solid in the sample was harvested in the same manner as the other samples. This result indicates that the sulfate salt of cis-itraconazole is insoluble or only slightly soluble in THF.

The di-HCl salt was isolated from attempts to make ternary systems containing both HCl and a dicarboxylic acid. The morphology of the crystals in all samples indicated the same salt/co-crystal form despite the presence of different dicarboxylic acids, which is consistent only with Di-HCl salt formation.

The samples were examined by powder x-ray diffraction (PXRD), thermogravimetric analysis (TGA), and differential scanning calorimetry (DSC), and the hygroscopicity of the samples were determined, as set forth below.

Analytical Equipment and Procedures

Thermogravimetric Analysis

Thermogravimetic analysis of each sample was performed using a Q500 Thermogravimetric Analyzer (TA Instruments, New Castle, Del., U.S.A.), which uses as its control software Advantage for QW-Series, version 1.0.0.78, Thermal Advantage Release 2.0 (©2001 TA Instruments-Water LLC), with the following components: QDdv.exe version 1.0.0.78 build 78.2; RHBASE.DLL version 1.0.0.78 build 78.2; RHCOMM.DLL version 1.0.0.78 build 78.0; RHDLL.DLL version 1.0.0.78 build 78.1; an TGA.DLL version 1.0.0.78 build 78.1. In addition, the analysis software used was Universal Analysis 2000 for Windows 95/95/2000/NT, version 3.1E; Build 3.1.0.40 (©1991-2001 TA Instruments-Water LLC).

For all of the experiments, the basic procedure for performing thermogravimetric analysis comprised transferring an aliquot of a sample into a platinum sample pan (Pan part # 952019.906; (TA Instruments, New Castle, Del. USA)). The pan was placed on the loading platform and was then automatically loaded into the Q500 Thermogravimetric Analyzer using the control software. Thermograms were obtained by individually heating the sample at 10° C./minute across a temperature range (generally from 25° C. to 300° C.) under flowing dry nitrogen (compressed nitrogen, grade 4.8 (BOC Gases, Murray Hill, N.J. USA)), with a sample purge flow rate of 60 mL/minute and a balance purge flow rate of 40 mL/minute. Thermal transitions (e.g., weight changes) were viewed and analyzed using the analysis software provided with the instrument.

Differential Scanning Calorimetry

DSC analysis of each sample was performed using a Q1000 Differential Scanning Calorimeter (TA Instruments, New Castle, Del., U.S.A.), which uses Advantage for QW-Series, version 1.0.0.78, Thermal Advantage Release 2.0 (©2001 TA Instruments-Water LLC), with the following components: QDdv.exe version 1.0.0.78 build 78.2; RHBASE.DLL version 1.0.0.78 build 78.2; RHCOMM.DLL version 1.0.0.78 build 78.0; RHDLL.DLL version 1.0.0.78 build 78.1; an TGA.DLL version 1.0.0.78 build 78.1. In addition, the analysis software used was Universal Analysis 2000 for Windows 95/95/2000/NT, version 3.1E; Build 3.1.0.40 (©2001 TA Instruments-Water LLC).

For all of the DSC analyses, an aliquot of a sample was weighed into an aluminum sample pan (Pan part # 900786.091; lid part # 900779.901 (TA Instruments, New Castle Del. USA)). The sample pan was closed (the pans are closed, but they aren't truly sealed to be air-tight for most samples) either by crimping for dry samples or press fitting for wet samples (such as hydrated or solvated samples). The sample pan was loaded into the Q1000 Differential Sanning Calorimeter, which is equipped with an autosampler, and a thermogram was obtained by individually heating the same using the control software at a rate of 10° C./minute from $T_{min}$ (typically 30° C.) to $T_{max}$ (typically 300° C.) using an empty aluminum pan as a reference. Dry nitrogen (compressed nitrogen, grade 4.8 (BOC Gases, Murray Hill, N.J. USA)) was used as a sample purge gas and was set at a flow rate of 50 mL/minute. Thermal transitions were viewed and analyzed using the analysis software provided with the instrument.

Powder X-Ray Diffraction

All X-ray powder diffraction patters were obtained using a D/Max Rapid X-ray Diffractometer (Rigaku/MSC, The Woodlands, Tex., U.S.A.) equipped with a copper source ($Cu/K_\alpha$ 1.5406 Å), manual x-y stage, and 0.3 mm collimator. A sample was loaded into a 0.3 mm quartz capillary tube (Charles Supper Company, Natick, Mass., U.S.A.) by sectioning off the closed end of the tube and tapping the small, open end of the capillary tube into a bed of the powdered sample or into the sediment of a slurried sample. The precipitate can be amorphous or crystalline. The loaded capillary tube was mounted in a holder that was placed and fitted into the x-y stage. A diffractogram was acquired using control software (RINT Rapid Control Software, Rigaku Rapid/XRD, version 1.0.0 (©1999 Rigaku Co.)) under ambient conditions at a power setting of 46 kV at 40 mA in transmission mode, while oscillating about the omega-axis from 0-5 degrees at 1 degree/second, and spinning about the phi-axis over 360 degrees at 2 degrees/second. The exposure time was 15 minutes unless otherwise specified.

The diffractogram obtained was integrated of 2-theta from 2-60 degrees and chi (1 segment) from 0-36 degrees at a step size of 0.02 degrees using the cyllnt utility in the RINT Rapid display software (RINT Rapid display software, version 1.18 (Rigaku/MSC)) provided by Rigaku with the instrument. The dark counts value was set to 8 as per the system calibration by Rigaku. No normalization or omega, chi or phi offsets were used for the integration.

The relative intensity of peaks in a diffractogram were determined by visual comparison of the peaks in the diffractogram. The relative intensity of the peaks is not necessarily a limitation of the PXRD pattern because peak intensity can vary from sample to sample due to crystalline impurities. Further, the angles of each peak can vary by about +/−0.1 degrees. The entire pattern or most of the pattern peaks may also shift by about +/−0.1 degree due to differences in calibration, settings, and other variations from instrument to instrument and operator to operator. The relative intensity is designated as strong (S), medium (M), and weak (W).

Hygroscopicity Determination

The hygroscopicity profiles for a sample from each of vials 1-5, as well as cis-itraconazole free base, were determined by exposing a sample from each of vials 1-5 to four different environments of varying relative humidity (namely, 0%, 30%, 57%, and 75%), and incubating the samples in that environment for about 8 hours at room temperature (20-25° C.). The humidity chambers consisted of desiccators with desiccants/salt baths in the bottom, above which the open vials containing samples were suspended. Solid phosphorous pentoxide was used to achieve ~0% relative humidity, saturated aqueous magnesium bromide solution was used to provide ~30% relative humidity, saturated aqueous sodium bromide solution was used to provide ~57% relative humidity, and saturated aqueous sodium chloride solution was used to provide ~75% relative humidity.

The relative hygroscopicity of each sample was determined using methods well known to one skilled in the pharmaceutical arts as reported in "Pharmaceutical Preformulation & Formulation: A Practical Guide From Candidate Drug Selection to Commercial Dosage Form," Ed. Mark Gibson, published by IHS Health Group Co, p. 49 (2001), which is incorporated herein by reference in its entirety. In particular, samples exhibiting greater than 0.2% and less than 2% weight loss after incubation in 75% relative humidity at 25° C. for 8 hours are categorized as slightly hygroscopic. Samples exhibiting greater than 2% and less than 15% weight loss after incubation in 75% relative humidity at 25° C. for 8 hours are categorized as hygroscopic. And samples exhibiting weight loss greater than or equal to 15% after incubation in 75% relative humidity at 25° C. for 8 hours are categorized as very hygroscopic.

Results

DL-Tartaric Acid Co-Crystal

TGA of a sample from vial 1 (cis-itraconazole-DL-tartaric acid) was performed by placing 10.931 mg of sample in the sample pan. The starting temperature was 25° C. with a heating rate of 10° C./minute, and the ending temperature was 400° C. DSC analysis of a sample from vial 1 was performed by placing 4.311 mg of sample in an aluminum pan with a press fitted pan closure, and $T_{min}$ was 30° C. and $T_{max}$ was 300° C.

The molecular formula of cis-itraconazole DL-tartrate is $C_{39}H_{44}Cl_2N_8O_{10}$. The compound synthesized in vial 1 of this Example 1 was a slightly hygroscopic, and demonstrated a minor broad endothermic transition at 84.1° C.±1.0° C. and a large broad endothermic transition at 174.1° C.±1.0° C. The smaller endotherm most likely results from a minor polymorph or solvate of cis-itraconazole tararic acid co-crystal. The sample lost 2.1% of its weight while being heated from room temperature to 125° C. in the TGA.

A sample from vial 1 was examined by PXRD using collection times of both 15 and 90 minutes. The PXRD pattern for the cis-itraconazole-dl-tartaric acid co-crystal sample prepared in vial 1 has a powder X-ray diffraction pattern with identifying features that include those listed below in Table 2:

TABLE 2

| Cis-Itraconazole-DL-Tartaric acid co-crystal | |
|---|---|
| 2-theta | Relative Intensity |
| 6.2 | M |
| 8.8 | M |
| 16.0 | M |
| 16.9 | S |
| 17.3 | S |
| 21.0 | S |
| 26.2 | M |

Phosphate Salt

TGA of a sample from vial 2 (cis-itraconazole phosphate) was performed by placing 1.211 mg of sample in the sample pan. DSC analysis of a sample from vial 2 was performed by placing 1.335 mg of sample in the sample pan with a press fitted pan closure, and $T_{min}$ was 30° C. and $T_{max}$ was 300° C.

The molecular formula of cis-itraconazole phosphate is $C_{35}H_{41}Cl_2N_8O_8P$. The compound synthesized in vial 2 of this Example 1 was a slightly hygroscopic, white powder that appeared as birefringent particles with irregular morphology when viewed by polarized light microscopy. The DSC trace of the material had a broad rolling base line preceding a broad endothermic transition at 142.2° C.±1.0° C. and a broad exothermic transition at 182.6° C.±1.0° C. The sample lost 3.2% of its weight while being heated from room temperature to 125° C. in the TGA.

A sample from vial 2 was examined by PXRD using collection times of both 15 and 90 minutes. The PXRD pattern for the cis-itraconazole phosphate sample prepared in vial 2 has a powder X-ray diffraction pattern with identifying features that include those listed below in Table 3:

TABLE 3

| Cis-Itraconazole Phosphate | |
|---|---|
| 2-theta | Relative Intensity |
| 3.2 | S |
| 5.5 | W |
| 9.6 | W |
| 17.4 | W |
| 20.5 | W |
| 23.5 | W |

Sulfate Salt

TGA of a sample from vial 3 (cis-itraconazole sulfate) was performed by placing 4.945 mg of sample in the sample pan. DSC analysis of a sample from vial 3 was performed by placing 2.0190 mg of sample in the sample pan with a press fitted pan closure, and $T_{min}$ was 30° C. and $T_{max}$ was 300° C.

The molecular formula of cis-itraconazole sulfate is $C_{35}H_{40}Cl_2N_8O_8S$. The compound synthesized in vial 3 of this Example 1 was a hygroscopic white powder that appeared as birefringent particles with irregular morphology when viewed by polarized light microscopy. It demonstrated a single broad and intense endothermic transition at 224.0° C.±1.0° C. that corresponds to a sudden 18% loss in weight as measured by TGA. The sample also contains volatile components as indicated by a weight loss of 2.4% during heating from room temperature to 125° C. in the TGA.

The PXRD pattern for the cis-itraconazole sulfate sample prepared in vial 3 has a powder X-ray diffraction pattern with identifying features that include those listed below in Table 4:

TABLE 4

| Cis-Itraconazole Sulfate | |
|---|---|
| 2-theta | Relative Intensity |
| 3.6 | S |
| 8.2 | W |
| 13.6 | W |

Fumaric Acid Co-Crystalic Acid Co-Crystal

TGA of a sample from vial 4 (cis-itraconazole fumaric acid co-crystal) was performed by placing 3.233 mg of sample in the sample pan. The starting temperature was 25° C. with a heating rate of 10° C./minute, and the ending temperature was 400° C. DSC analysis of a sample from vial 4 was performed by placing 2.348 mg of sample in the sample pan with a press fitted pan closure, and $T_{min}$ was 30° C. and $T_{max}$ was 300° C.

The molecular formula of cis-itraconazole fumaric acid co-crystal is $C_{39}H_{42}Cl_2N_8O_8$. The compound synthesized in vial 4 of this Example 1 was a slightly hygroscopic white powder consisting of birefringent rectangular plates by polarized light microscopy. The sample demonstrated endothermic transitions at 141.7° C.±1.0° C. and 178.1° C.±1.0° C. The material contains 1.4% of volatile components as measured by TGA.

A sample from vial 4 was examined by PXRD using collection times of both 15 and 90 minutes. The PXRD pattern for the cis-itraconazole fumaric acid co-crystal sample prepared in vial 4 has a powder X-ray diffraction pattern with identifying features that include those listed below in Table 5:

TABLE 5

Cis-Itraconazole Fumaric acid co-crystal

| 2-theta | Relative Intensity |
| --- | --- |
| 4.6 | M |
| 5.9 | M |
| 10.6 | W |
| 16.2 | M |
| 17.0 | M |
| 19.1 | S |
| 20.8 | S |

Besylate Salt

TGA of a sample from vial 5 (cis-itraconazole besylate) was performed by placing 4.470 mg of sample in the sample. DSC analysis of a sample from vial 5 (cis-itraconazole besylate) was performed by placing 2.270 mg of sample in the sample pan with a press fitted pan closure, and $T_{min}$ was 30° C. and $T_{max}$ was 300° C.

The molecular formula of cis-itraconazole benzensulfonate (or besylate) is $C_{41}H_{44}Cl_2N_8O_7S$. The compound synthesized in vial 5 of this Example 1 was a hygroscopic, yellow powder with particles that appeared birefringent and had an irregular morphology by polarized light microscopy, with a endothermic transitions at 165.7° C.±1.0° C. and 186.1° C.±1.0° C.

The PXRD pattern for the cis-itraconazole besylate sample prepared in vial 5 has a powder X-ray diffraction pattern with identifying features that include those listed below in Table 6:

TABLE 6

Cis-Itraconazole Besylate

| 2-theta | Relative Intensity |
| --- | --- |
| 3.4 | S |
| 10.2 | W |
| 16.1 | W |
| 18.5 | M |
| 20.1 | S |
| 25.0 | S |
| 28.0 | W |

Example 2

Synthesis and Analysis of Cis-Itraconazole Sulfate

Synthesis of Cis-Itraconazole Sulfate

Approximately 1 g of cis-itraconazole free base (Lot # KEO 0026, Química Sinética S.A.) was placed in a beaker containing a magnetic, TEFLON coated stirring bar, and 200 ml of methanol (Lot V37E24, JT Baker) was added to the beaker and stirred. With stirring, about 154 μl of 98% sulfuric acid (Fluka Lot 411530/1 42400) was then added to the beaker (resulting in a 2.05:1 ratio of salt former to free base). The solution was air dried until all the solvent was visibly removed, and the resulting product was placed in a vacuum oven under vacuum at about 45° C. and allowed to dry over a weekend.

Analysis and Results

The resulting product of the synthesis in this Example 2 was analyzed by TGA, DSC, and PXRD using the same equipment, software, procedures, and parameters described in Example 1 unless otherwise specified.

TGA was performed on a sample of the resulting product by placing 8.0610 mg of sample in the sample pan. The starting temperature was 20° C. with a heating rate of 10° C./minute, and the ending temperature was 300° C. DSC was performed by placing 1.4890 mg of sample in the sample pan with a press fitted pan closure. The $T_{min}$ was 30° C. with a heating rate of 10° C./minute, and the $T_{max}$ was 300° C.

The compound synthesized in this Example 2 was a white powder consisting of particles with irregular morphology that were birefringent by polarized light microscopy. The DSC trace of the material showed a broad endothermic transition at 222.9° C.±2.0° C., which corresponds to a sudden weight loss of 18.7% by TGA. The material contained 1.2% volatile components by weight.

A sample of this compound was examined by PXRD using a collection time of 90 minutes. The PXRD pattern for the cis-itraconazole sulfate sample prepared in this Example 2 has a powder X-ray diffraction pattern with identifying features that include those listed below in Table 7:

TABLE 7

Cis-Itraconazole Sulfate

| 2-theta | Relative Intensity |
| --- | --- |
| 3.6 | S |
| 8.2 | W |
| 13.5 | M |
| 19.4 | W |
| 22.9 | W |
| 24.3 | W |
| 27.0 | W |

Example 3

Synthesis and Analysis Cis-Itraconazole Fumaric Acid Co-Crystal

Synthesis of Cis-Itraconazole Fumaric Acid Co-Crystal

Approximately 500 mg of cis-itraconazole free base (Lot # KEO 0026, Química Sinética S.A.) was placed in a 50 ml screw top bottle along with 33.33 ml of tetrahydrofuran ("THF") (Lot # 50K1485, Sigma Chemicals Co.). 3088.7 μl of fumaric acid stock solution (prepared in Example 1) was then added to the beaker (resulting in a 1.05:1 ratio of salt former to free base). The cap was screwed on to seal the bottle and the bottle was placed in a 70° C. oven (Model # 1400E, VWR Scientific) and heated for approximately 1 hour. Thereafter, the bottle was removed from the oven, the cap from the bottle was removed, and the sample was allowed to evaporate under flowing air under ambient conditions. When all but about 5 ml of the solvent had evaporated, the remaining solvent was removed by decantation and the solid was isolated by filtering over a Whatman filter using suction. This solid was returned back into the 50 ml bottle with the remaining solid and the bottle was placed into the vacuum oven at approximately 25 mm Hg and the solid was allowed to dry for 4 days.

Analysis and Results

The resulting product from this Example 3 was then analyzed by TGA, DSC, and PXRD using the same equipment, software, procedures, and parameters described in Example 1 unless otherwise specified.

TGA was performed on a sample of the resulting product by placing 4.1810 mg of sample in the sample pan. The starting temperature was 20° C. with a heating rate of 10° C./minute, and the ending temperature was 300° C. DSC was performed by placing 1.9630 mg of sample in the sample pan with a press fitted pan closure, and $T_{min}$ was 30° C. and $T_{max}$ was 300° C.

The compound synthesized in this Example 3 was a white powder that appeared as birefringent rectangular plates and irregular particles by polarized light microscopy. The material had a weak endothermic transition at 141.7° C.±1° C. and a strong endothermic transition at 178.1° C.±1° C. The sample loses 0.5% of its weight on the TGA between room temperature and 100° C.

A sample of this compound was examined by PXRD using a collection time of 90 minutes. The PXRD pattern for the cis-itraconazole fumaric acid co-crystal sample prepared in this Example 3 has a powder X-ray diffraction pattern with identifying features that include those listed below in Table 8:

TABLE 8

Cis-Itraconazole fumaric acid co-crystal

| 2-theta | Relative Intensity |
| --- | --- |
| 4.6 | M |
| 5.9 | M |
| 9.2 | W |
| 10.6 | M |
| 19.1 | S |
| 20.8 | S |

In addition, the physical form of the cis-itraconazole fumaric acid co-crystal prepared in this Example 3 was assessed. Specifically, 1 mg of the cis-itraconazole fumaric acid co-crystal prepared in this Example 3 was deposited into a single well of a polystyrene 384 well plate. 70 μl of pH 1 buffer (1 N HCl adjusted to pH 1 using 1 N NaOH) was added to the same well. The sample was incubated at room temperature with vigorous mixing for 2 hours. At the end of the assay, the 384 well plate was centrifuged for 2 minutes at 500 xg and the supernatant was removed by aspiration.

The remaining solid state was analyzed by X-ray powder diffraction in a borosilicate tube, but otherwise using the same equipment, software, procedures, and parameters described in Example 1. Fresh cis-itraconazole freebase and cis-itraconazole fumaric acid co-crystal prepared in this Example 3 were also analyzed using x-ray powder diffraction to compare with the incubated experimental sample. A comparison of the resulting PXRD patterns indicated that the solid state of the cis-itraconazole fumaric acid co-crystal prepared in this Example 3 did not change form after 2 hours of incubation in pH 1 buffer.

Example 4

Synthesis and Analysis of Cis-Itraconazole-L-Tartaric Acid Co-Crystal

Synthesis of Cis-Itraconazole-L-Tartaric Acid Co-Crystal

Approximately 100.4 mg of cis-itraconazole free base (Lot # KEO 0026, Química Sinética S.A), 0.90 ml of THF, and a magnetic stir bar were charged into a screw cap vial, heated to reflux to dissolve, and then the vial was closed with the screw cap and placed in an oil bath maintained at 70° C. A solution of 138.5 mg of L(+) tartaric acid in 1.15 ml of THF was prepared. 0.21 ml of the L(+)tartaric acid solution was added to the cis-Itraconazole solution and the solution remained clear. 0.90 ml of iso-propylacetate was added and the solution was seeded with <1 mg of the salt from vial 1 of Example 1 above. The sample was allowed to crystallize over about 5 minutes in the 70° C. oil bath before it was removed and allowed to cool to room temperature. The cooled sample was suction filtered. It was rinsed with 0.2-0.3 ml of THF. The filter cake was broken-up and allowed to air-dry for 4 hours prior to analysis.

Analysis and Results

The resulting product from this Example 4 was then analyzed by TGA, DSC, and PXRD using the same equipment, software, procedures, and parameters described in Example 1 unless otherwise specified.

TGA of a sample from this Example 4 (cis-itraconazole L-tartaric acid co-crystal) was performed by placing 2.42 mg of sample in the sample pan. The starting temperature was 25° C. with a heating rate of 10° C./minute, and the ending temperature was 300° C. DSC analysis of a sample from this Example 4 was performed by placing 1.824 mg of sample in an aluminum pan with a press fitted pan closure, and $T_{min}$ was 30° C. and $T_{max}$ was 300° C.

The molecular formula of cis-itraconazole tartaric acid co-crystal is $C_{39}H_{44}Cl_2N_8O_{10}$. The compound synthesized in this Example 4 appeared as white, birefingent needles by polarized light microscopy. The sample contained less than 0.1% volatile components by weight by TGA. The sample has an endothermic transition at 182.5° C.±1.0° C.

A sample of the solid from this Example 4 was examined by PXRD using a collection time of 10 minutes. The PXRD pattern for the cis-itraconazole-L-tartaric acid co-crystal from this Example 4 has a powder X-ray diffraction pattern with identifying features that include those listed below in Table 9:

TABLE 9

Cis-Itraconazole L-Tartaric acid co-crystal

| 2-theta | Relative Intensity |
| --- | --- |
| 4.1 | S |
| 6.2 | S |
| 8.3 | S |
| 20.7 | S |
| 25.6 | W |
| 26.3 | W |

Example 5

Synthesis and Analysis of Cis-Itraconazole-D-Tartaric Acid Co-Crystal

Synthesis of Cis-Itraconazole-D(−)Tartaric Acid Co-Crystal

Approximately 100.4 mg of cis-itraconazole free base (Lot # KEO 0026, Química Sinética S.A), 0.90 ml of THF, and a magnetic stir bar were charged into a screw cap vial, heated to reflux to dissolve, then the vial was closed using the screw cap and placed in an oil bath maintained at 70° C. A solution of 124.2 mg of D(−) tartaric acid in 1.0 ml of THF plus 0.010 ml of water was prepared. 0.21 ml of the D(−)tartaric acid solution was added to the cis-Itraconazole solution and the solution remained clear. 0.90 ml of iso-propylacetate was added and the solution was seeded with <1 mg of the salt from vial 1 of Example 1 above. The sample was allowed to crystallize over about 5 minutes in the 70° C. oil bath before it was removed and allowed to cool to room temperature. The cooled sample was suction filtered. It was rinsed with 0.2-0.3 ml of THF. The filter cake was broken-up and allowed to air-dry for 4 hours prior to analysis.

Analysis and Results

The resulting product from this Example 5 was then analyzed by TGA, DSC, and PXRD using the same equipment, software, procedures, and parameters described in Example 1 unless otherwise specified.

TGA of a sample from this Example 5 (cis-itraconazole D-tartaric acid co-crystal) was performed by placing 4.019 mg of sample in the sample pan. The starting temperature was 25° C. with a heating rate of 10° C./minute, and the ending temperature was 300° C. DSC analysis of a sample of the solid from this Example 5 was performed by placing 1.824 mg of sample in an aluminum pan with a press fitted pan closure, and $T_{min}$ was 30° C. and $T_{max}$ was 300° C.

The molecular formula of cis-itraconazole tartaric acid co-crystal is $C_{39}H_{44}Cl_2N_8O_{10}$. The compound synthesized in this Example 5 appeared as white, birefingent needles by polarized light microscopy. The sample contained less than 0.1% volatile components by weight by TGA.

The sample has a strong endothermic transition at 181.6° C.±1.0° C. and a weak endothermic transition at 145.3° C.±1.0° C. The weak endothermic transition suggests that the material contains a small amount of a second polymorph or solvate of cis-itraconazole-D-tartaric acid co-crystal.

A sample of the solid from this Example 5 was examined by PXRD using a collection time of 10 minutes. The PXRD pattern for the cis-itraconazole-D-tartaric acid co-crystal sample prepared in this Example 5 has a powder X-ray diffraction pattern with identifying features that include those listed below in Table 10:

TABLE 10

Cis-Itraconazole-D-Tartaric acid co-crystal

| 2-theta | Relative Intensity |
| --- | --- |
| 4.1 | S |
| 6.2 | S |
| 7.2 | W |
| 8.3 | S |
| 11.8 | W |
| 20.8 | S |

The peaks at 7.2 and 11.8 2-theta are very weak but are distinct from peaks in cis-itraconazole-L-tartaric acid co-crystal. However, considering the similarities between the other peaks in the patterns, these peaks most likely result from a polymorph or solvate.

Example 6

Synthesis and Analysis of Cis-Itraconazole DL-Tartaric Acid Co-Crystal

Synthesis of Cis-Itraconazole DL-Tartaric Acid Co-Crystal

Approximately 100.4 mg of cis-itraconazole free base (Lot # KEQ 0026, Química Sinética S.A), 0.90 ml of THF, and a magnetic stir bar were charged into a screw cap vial, heated to reflux to dissolve, and then the vial was closed with the screw cap and placed in an oil bath maintained at 70° C. A solution of 123.1 mg of DL-tartaric acid in 1.02 ml of THF plus 0.10 ml of water was prepared. 0.21 ml of the DL-tartaric acid solution was added to the cis-Itraconazole solution and the solution remained clear. 0.90 ml of iso-propylacetate was added and the solution was seeded with <1 mg of the salt from vial 1 of Example 1 above. The sample was allowed to crystallize over about 5 minutes in the 70° C. oil bath before it was removed and allowed to cool to room temperature. The cooled sample was suction filtered. It was rinsed with 0.2-0.3 ml of THF. The filter cake was broken-up and allowed to air-dry for 4 hours prior to analysis.

Analysis and Results

The resulting product from this Example 6 was then analyzed by TGA, DSC, and PXRD using the same equipment, software, procedures, and parameters described in Example 1 unless otherwise specified.

TGA of a sample of the solid from this Example 6 (cis-itraconazole DL-tartaric acid co-crystal) was performed by placing 3.482 mg of sample in the sample pan. The starting temperature was 25° C., the heating rate was 10° C./minute, and the ending temperature was 300° C. DSC analysis of a sample of the solid from this Example 6 was performed by placing 1.036 mg of sample in an aluminum pan with a press fitted pan closure, and $T_{min}$ was 30° C. and $T_{max}$ was 300° C.

The molecular formula of cis-itraconazole tartaric acid co-crystal is $C_{39}H_{44}Cl_2N_8O_{10}$. The compound synthesized in this Example 6 appeared as white, birefingent needles by polarized light microscopy. The sample contained less than 0.1% volatile components by weight by TGA. The sample has a strong endothermic transition at 174.9° C.±1.0° C. and two weaker endothermic transitions at 141.8° C.±1.0° C. and 179.3° C.±1.0° C. The presence of multiple endothermic transitions indicates that the sample contains small quantities of other polymorphs or solvates of cis-itraconazole-DL-tartaric acid co-crystal.

A sample of the product from this Example 6 was examined by PXRD using a collection time of 10 minutes. The PXRD pattern for the cis-itraconazole-DL-tartaric acid co-crystal sample prepared in this Example 6 has a powder X-ray diffraction pattern with identifying features that include those listed below in Table 11:

TABLE 11

Cis-Itraconazole DL-Tartaric acid co-crystal

| 2-theta | Relative Intensity |
| --- | --- |
| 6.1 | S |
| 8.8 | S |
| 15.9 | M |
| 16.9 | S |
| 17.3 | S |
| 21.0 | S |
| 22.6 | M |
| 26.2 | M |

Example 7

Synthesis and Analysis of Cis-Itraconazole Succinic Acid Co-Crystal

Synthesis of Cis-itraconazole Succinic Acid Co-Crystal

Approximately 51.1 mg of cis-itraconazole free base (Lot # KEO 0026, Química Sinética S.A), 0.75 ml of THF, and a magnetic stir bar were charged into a screw cap vial, heated to reflux to dissolve, and then the vial was closed with the screw cap and placed on top of a hot plate maintained at a temperature between 60 and 75° C. A solution of 77.7 mg of succinic acid in 1.58 ml of THF was prepared. 0.20 ml of the succinic acid solution was added to the cis-itraconazole solution and the solution remained clear. 0.75 ml of iso-propylacetate was added and the solution was seeded with <1 mg of the L-tartaric acid co-crystal salt from Example 4 above. The heat was turned off and the sample crystallized as it cooled to room temperature. The cooled sample was suction filtered. It was rinsed with 0.2-0.3 ml of THF. The filter cake was broken-up and allowed to air-dry for 1 hour prior to analysis.

Analysis and Results

The resulting product from this Example 7 was then analyzed by TGA, DSC, and PXRD using the same equipment, software, procedures, and parameters described in Example 1 unless otherwise specified.

TGA of a sample of the solid from this Example 7 (cis-itraconazole succinic acid co-crystal) was performed by placing 5.254 mg of sample in the sample pan. The starting temperature was 25° C., the heating rate was 10° C./minute, and the ending temperature was 300° C. DSC analysis of a sample of the solid from this Example 7 was performed by placing 1.074 mg of sample in an aluminum pan with a press fitted pan closure, and $T_{min}$ was 30° C. and $T_{max}$ was 300° C.

The molecular formula of cis-itraconazole succinic acid co-crystal is $C_{39}H_{44}Cl_2N_8O_8$. The compound synthesized in this Example 7 appeared as white powder by eye, and as birefingent polygonal plates by polarized light microscopy. The sample contained less than 0.1% volatile components by weight by TGA. The sample has a single endothermic transition at 161.0° C.±1.0° C.

A sample of the product from this Example 7 was examined by PXRD using a collection time of 10 minutes. The PXRD pattern for the cis-itraconazole succinic acid co-crystal sample prepared in this Example 7 has a powder X-ray diffraction pattern with identifying features that include those listed below in Table 12:

TABLE 12

Cis-Itraconazole Succinic acid co-crystal

| 2-theta | Relative Intensity |
|---|---|
| 3.0 | M |
| 6.0 | W |
| 8.1 | W |
| 9.0 | W |
| 17.1 | S |
| 24.5 | M |

Example 8

Synthesis and Analysis of Cis-Itraconazole L-Malic Acid Co-Crystal Form A

Synthesis of Cis-Itraconazole L-Malic Acid Co-Crystal Form A

To prepare the L-malic acid co-crystal salt of cis-itraconazole, 100.4 mg of cis-itraconazole free base (Lot # KEO 0026, Química Sinética S.A), 0.50 ml of THF, and a magnetic stir bar were charged into a screw cap vial. A solution of 191.3 mg of 1(−)malic acid in 5.0 ml of THF was prepared. 0.50 ml of the 1-malic acid solution was added to the vial containing cis-itraconazole and the solution was heated with a heat gun to dissolve. The solution was allowed to cool and was then seeded with <1 mg of the salt from cis-itraconazole-1-tartaric acid co-crystal. The cooled crystals were filtered in a centrifuge filter tube. The filter cake was broken-up and allowed to air-dry prior to analysis.

Analysis and Results

The resulting product from this Example 8 was then analyzed by TGA, DSC, and PXRD using the same equipment, software, procedures, and parameters described in Example 1 unless otherwise specified.

TGA of a sample of the solid from this Example 8 (cis-itraconazole malic acid co-crystal form A) was performed by placing 5.672 mg of sample in the sample pan. The starting temperature was 25° C. with a heating rate of 10° C./minute, and the ending temperature was 300° C. DSC analysis of a sample from vial 1 was performed by placing 1.642 mg of sample in an aluminum pan with a press fitted pan closure, and $T_{min}$ was 30° C. and $T_{max}$ was 300° C.

The molecular formula of cis-itraconazole L-malic acid co-crystal form A is $C_{39}H_{44}Cl_2N_8O_9$. The compound appeared as white, birefingent needles by polarized light microscopy. The sample contained less than 0.1% volatile components by weight by TGA. The sample has a strong endothermic transition at 156.6° C.±1.0° C.

A sample of the product from this Example 8 was examined by PXRD D using a collection time of 10 minutes. The PXRD pattern for the cis-itraconazole 1-malic acid co-crystal form A sample has a powder X-ray diffraction pattern with identifying features that include those listed below in Table 13:

TABLE 13

Cis-Itraconazole-L-Malic Acid Co-Crystal Form A

| 2-theta | Relative Intensity |
|---|---|
| 4.4 | M |
| 5.9 | S |
| 8.8 | M |
| 17.7 | S |
| 20.0 | M |
| 21.1 | M |
| 22.6 | M |

Example 9

Synthesis and Analysis of Cis-Itraconazole Hydrochloride

Synthesis of Cis-Itraconazole Di-HCl

The di-HCl salt was isolated from attempts to make ternary systems containing both HCl and a dicarboxylic acid. The morphology of the crystals in all samples indicated the same salt/co-crystal form despite the presence of different dicarboxylic acids, which is consistent only with di-HCl salt formation.

Analysis and Results

There appeared to be two different forms of the di-HCl salt which vary in weight loss, DSC trace and PXRD pattern. Both appeared to be solvates, but with a possible change in the amount of HCl incorporated (0.5-2.0 equivalents). The weight loss by TGA occurs in two steps between room temperature and 150° C. and varies from about 11-16%. The material has 2-3 endothermic transitions by DSC. The first is at 55-70° C., the second is at 113-120° C. and the third (when present) is at 155-157° C.

Example 10

Solubility of Cis-Itraconazole Free Base and Cis-Itraconazole Fumaric Acid Co-Crystal, Tartaric Acid Co-Crystal, and Phosphate Salt Excess solid (in the range of 0.5 to 1.5 mg) of each of cis-itraconazole free base (Lot # KEO 0026, Química Sinética S.A), cis-itraconazole tartaric acid co-crystal prepared in Example 1, cis-itraconazole phosphate prepared in Example 1, and cis-itraconazole fumaric acid co-crystal prepared in Example 3 was added to individual wells in a 96-well polypropylene plate. In general, eight wells were used per compound in order to have two replicate measurements at four different time points, but for the free base and fumaric acid co-crystal salt, 10 wells were used and measurements taken at five time points.

Solubility measurements were taken at 15, 30, 60, 120, and 240 minutes. Beginning with the longest time point, pH 1 buffer (1 N HCl adjusted to pH 1 using 1 N NaOH) was added to each of the wells containing samples until completion of the shortest time points. The samples were vigorously stirred throughout the experiment. At the end of the assay, the solution and solid states of all the samples were separated by centrifugation in a polyvinylidene fluoride 96-well filter plate for 2 minutes at 500 xg.

Approximately 30 µl of solution was collected from the solution state of each sample and diluted in 120 µl of methanol in glass vials. Aluminum caps were crimped on the vial tops to prevent evaporation of methanol. The vials were stored at 25° C. until solubility analysis was performed.

The solubility of each sample was measured using liquid chromatography with a UV detector, and in particular a Waters 2690 HPLC system with PDA detector run on Millenium 32 software. A 5 ml flowrate was used with 20 µl sample injection volumes into a 4.6×100 mm Chromolith Performance RP-18 column at 35° C. The mobile phase was composed of 55% acetonitrile and the balance was 50 mM sodium acetate at pH 5.0 with 0.2% triethylamine.

Figure 1B:
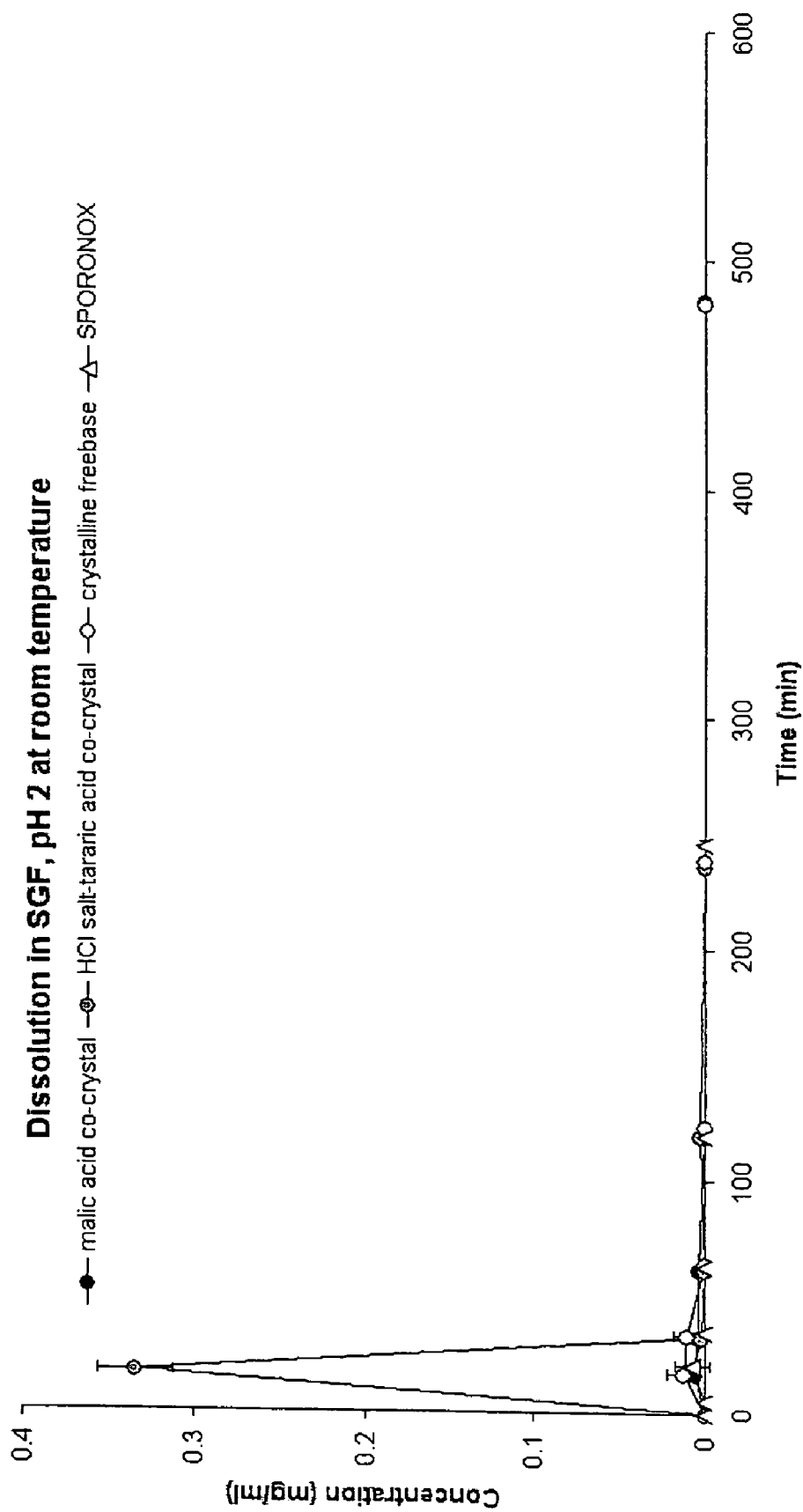

A comparison of the solubilities of cis-itraconazole free base, cis-itraconazole fumaric acid co-crystal, cis-itraconazole tartaric acid co-crystal, and cis-itraconazole phosphate from 0 to 120 minutes is shown in FIG. 1.

The results shown in FIG. 1 demonstrate the solubility of cis-itraconazole free base did not change over the measured period of time. In contrast, the solubility of cis-itraconazole salts were at least 4-fold larger (e.g., cis-itraconazole fumaric acid co-crystal) and at most 20-fold larger (e.g., cis-itraconazole tartaric acid co-crystal) than the free base at 15 minutes. The solubility of the salts generally decreased with time as evidenced at the 120 minute time point. At 4 hours, the solubility of the fumaric acid co-crystal salt was approximately 1.5-fold the solubility of the free base. The increased solubility of cis-itraconazole salts is likely to result in improved oral absorption relative to that of cis-itraconazole free base.

Example 11

Solubility in Artificial Gastric Juice

The solubility of cis-itraconazole benzenesulfonate (besylate), cis-itraconazole sulfate, cis-itraconazole phosphate, cis-itraconazole tartaric acid co-crystal, cis-itraconazole fumaric acid co-crystal, and cis-itraconazole succinic acid co-crystal in artificial gastric juice is compared to that of (±)cis-itraconazole free base. About 10 mg of compound to be tested is added to 100 ml of artificial gastric juice (such as 0.2 g NaCl+0.7 ml concentrated HCl diluted to 100 ml) at ambient temperature. This mixture is stirred and a sample is taken from each solution at regular intervals. The amount of dissolved active ingredient or compound of interest is measured by UV spectrometry (255 nm), if necessary after diluting the sample to a concentration suitable for UV spectrometry. The dissolved amount of each active ingredient is measured in mg/100 ml.

Example 12

Additonal Analysis of Cis-Itraconazole L-Malic Acid Co-Crystal Form B

Another sample of cis-itraconazole 1-malic acid co-crystal form B was prepared as in Example 8. This sample (designated MM_109_15) was analyzed by TGA, DSC, and PXRD using the same equipment, software, procedures, and parameters described in Example 1 unless otherwise specified. It was also analyzed by Raman spectroscopy.

Figure 2A:
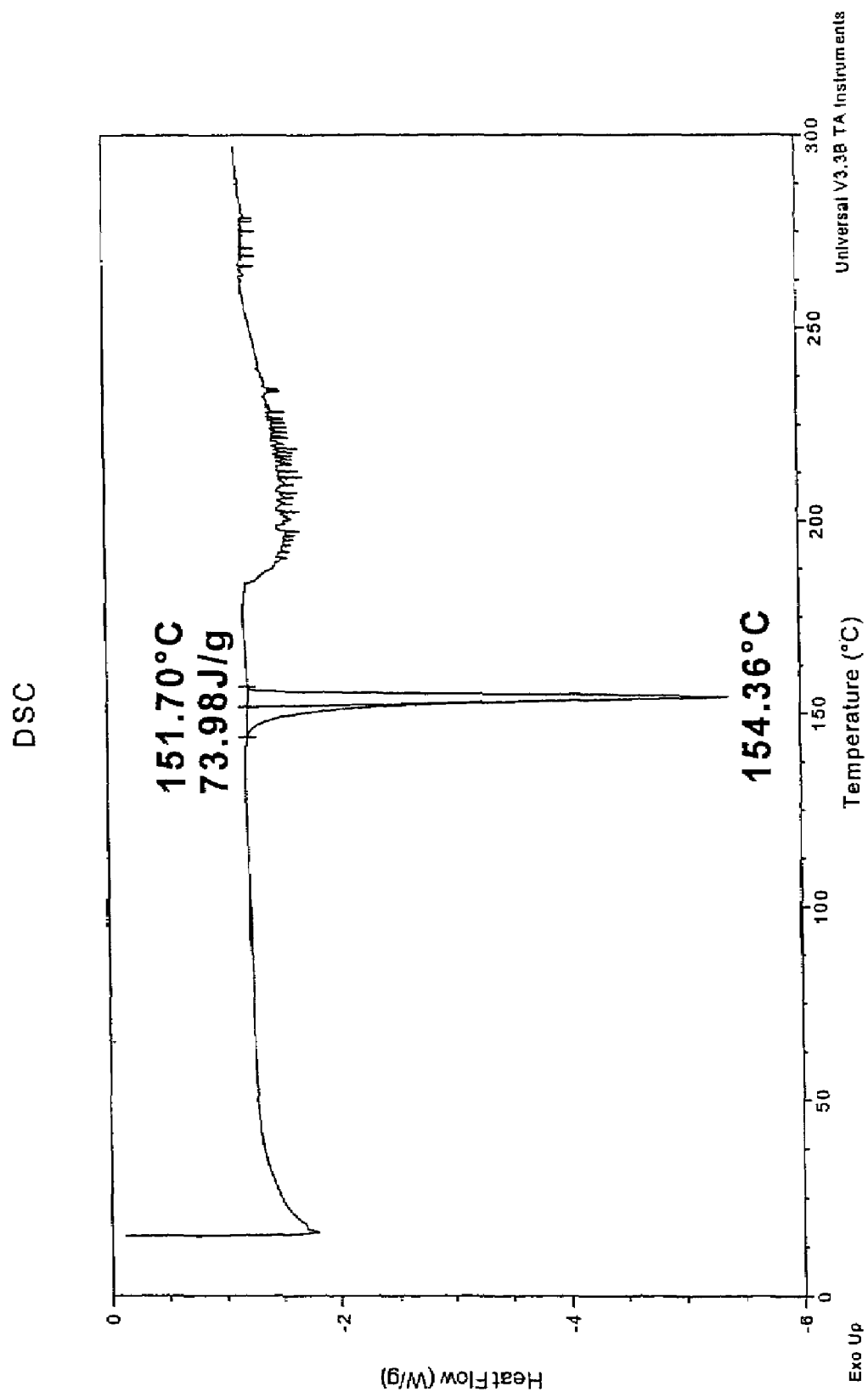
FIG. 2(a)-(d) illustrate the following:
(a) differential scanning calorimetry ("DSC") measurements of a cis-itraconazole maleic acid co-crystal taken from room temperature to 300° C. at 10° C./minute;
(b) thermogravimetic analysis ("TGA") of a cis-itraconazole maleic acid co-crystal taken from room temperature to 300° C. at 10° C./minute;
(c) powder X-ray diffraction ("PXRD") measurements of a cis-itraconazole maleic acid co-crystal; and
(d) Raman spectroscopic measurements of a cis-itraconazole maleic acid co-crystal.
Figure 2B:
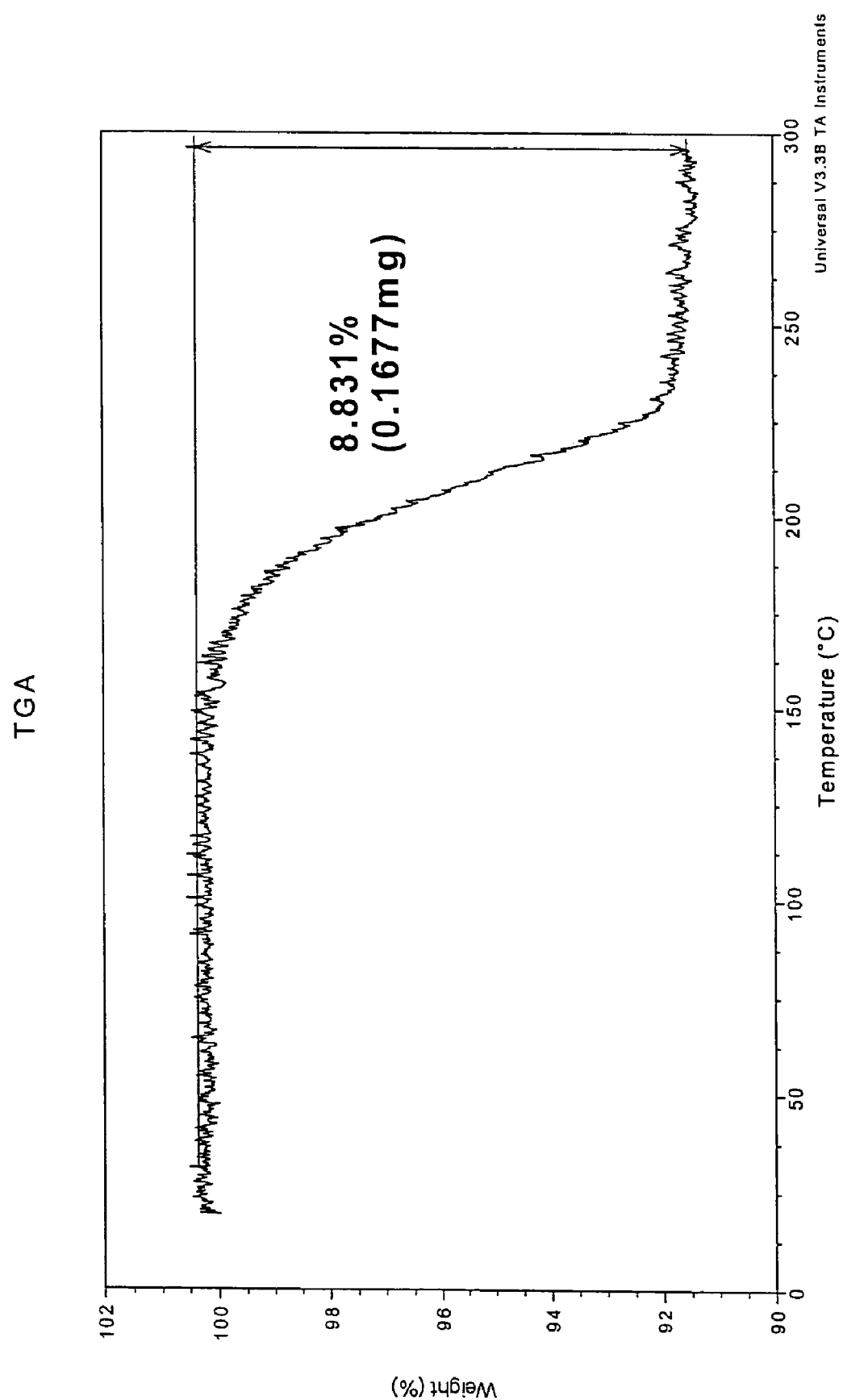

TGA of the sample was performed by placing 1.90 mg of sample in the sample pan. The starting temperature was 25° C. with a heating rate of 10° C./minute, and the ending temperature was 300° C. DSC analysis of the sample was performed by placing 1.214 mg of sample in an aluminum pan with a press fitted pan closure, and $T_{min}$ was 30° C. and $T_{max}$ was 300° C. TGA results for the sample are illustrated in FIG. 2(b). DSC results for this Example 12 are illustrated in FIG. 2(a).

The sample analyzed as described in this Example appeared as white, birefingent needles by polarized light microscopy. The sample contained less than 0.1% volatile components by weight by TGA. The sample has an endothermic transition at 154.4° C.±1.0° C.

Figure 2C:
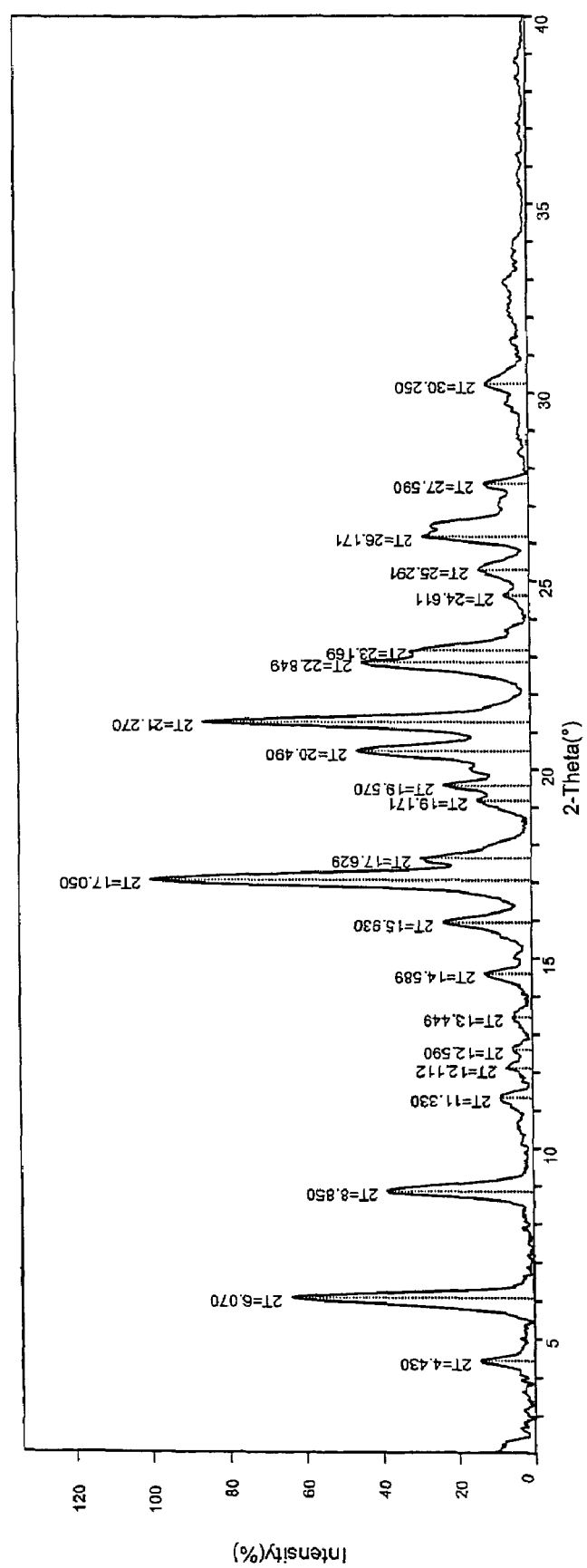

The sample was also examined by PXRD using a collection time of 10 minutes. Results of this measurement are illustrated in FIG. 2(c). The PXRD pattern for the cis-itraconazole 1-malic acid co-crystal form B sample had a powder X-ray diffraction pattern with identifying features that include those listed below in Table 14:

TABLE 14

Cis-Itraconazole l-Malic acid co-crystal form B

| 2-theta | Relative Intensity |
|---|---|
| 6.0 | M |
| 8.8 | M |
| 17.0 | S |
| 20.5 | M |
| 21.3 | S |
| 22.8 | M |

Figure 2D:
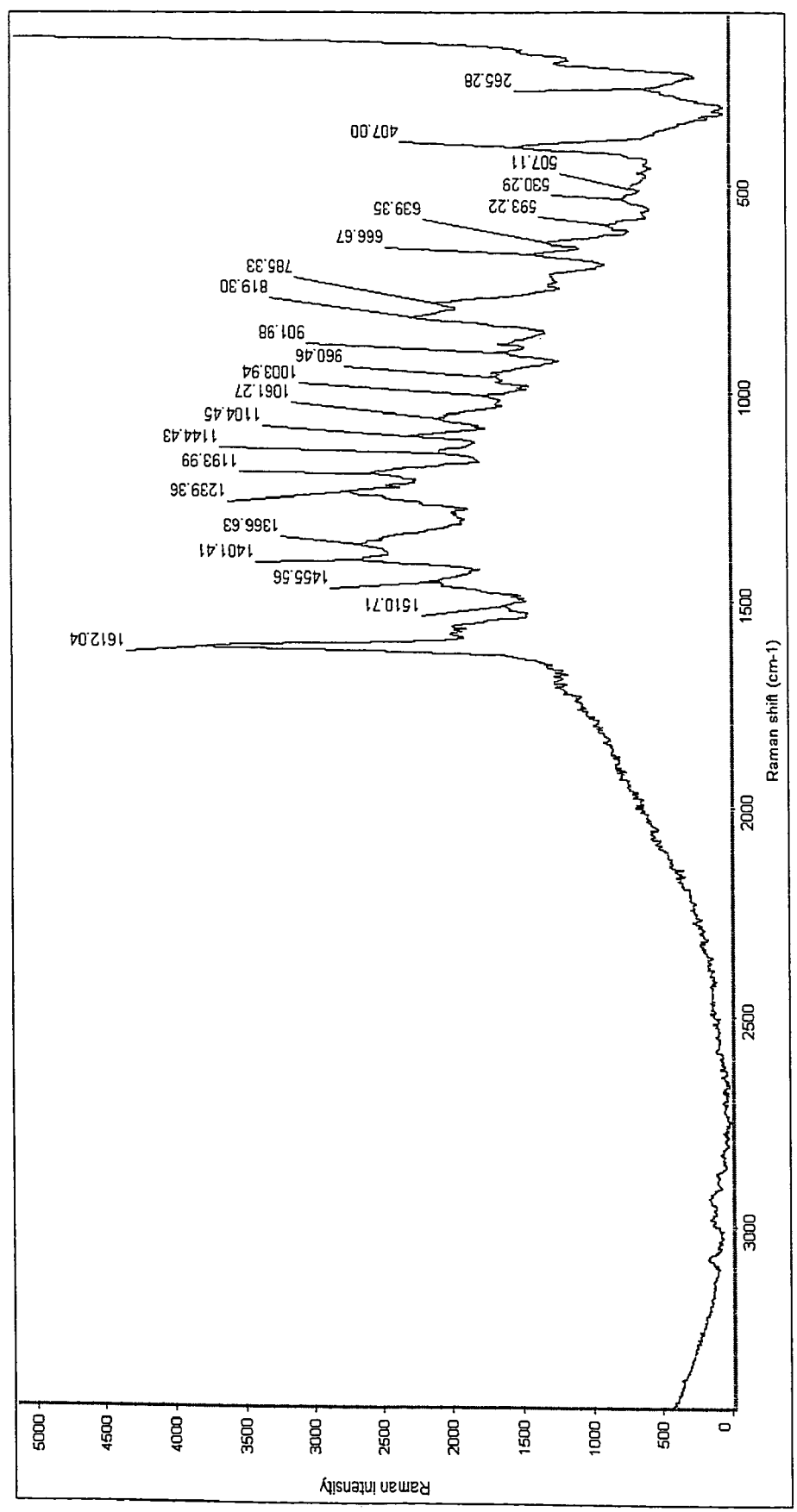

The results of Raman spectroscopic analysis of the cis-itraconazole 1-maleic acid co-crystal sample are illustrated in FIG. 2(d). Raman spectroscopic analysis measures optical emissions from vibrating and rotational states of a molecule and can determine natural frequency shift emissions useful in characterizing the biochemical properties of a molecule. When used for in vivo measurements, contrast agents known as Raman enhancing dyes or agents may be employed.

Example 13

Synthesis and Analysis of Cis-Itraconazole HCl Salt Tartaric Acid Co-Crystal

Approximately 212.7 mg of L-tartaric acid and 118 µL of 37% HCl were dissolved in 25 mL of hot dioxane. This solution was added to 1.0 g of cis-itraconazole dissolved in 50 mL of hot dioxane with stirring. The resulting clear solution was filtered on a 0.2 µm syringe filter into a 250 mL Erlenmeyer flask. Seed crystals from a previous preparation of the HCl-tartaric acid co-crystal salt were added, the solution was sonicated and left to stir overnight. The next day 50 mL tert-butyl methyl ether were added and the crystals were harvested by vacuum filtration on a Buchner funnel with #4 Whatman filter paper. The crystals were washed 3× with 5 mL aliquots of cold tert-butyl methyl ether and left to air dry. Approximately 573 mg of a crystalline form of cis-itraconazole HCl-tartaric acid co-crystal were obtained.

Figure 3A:
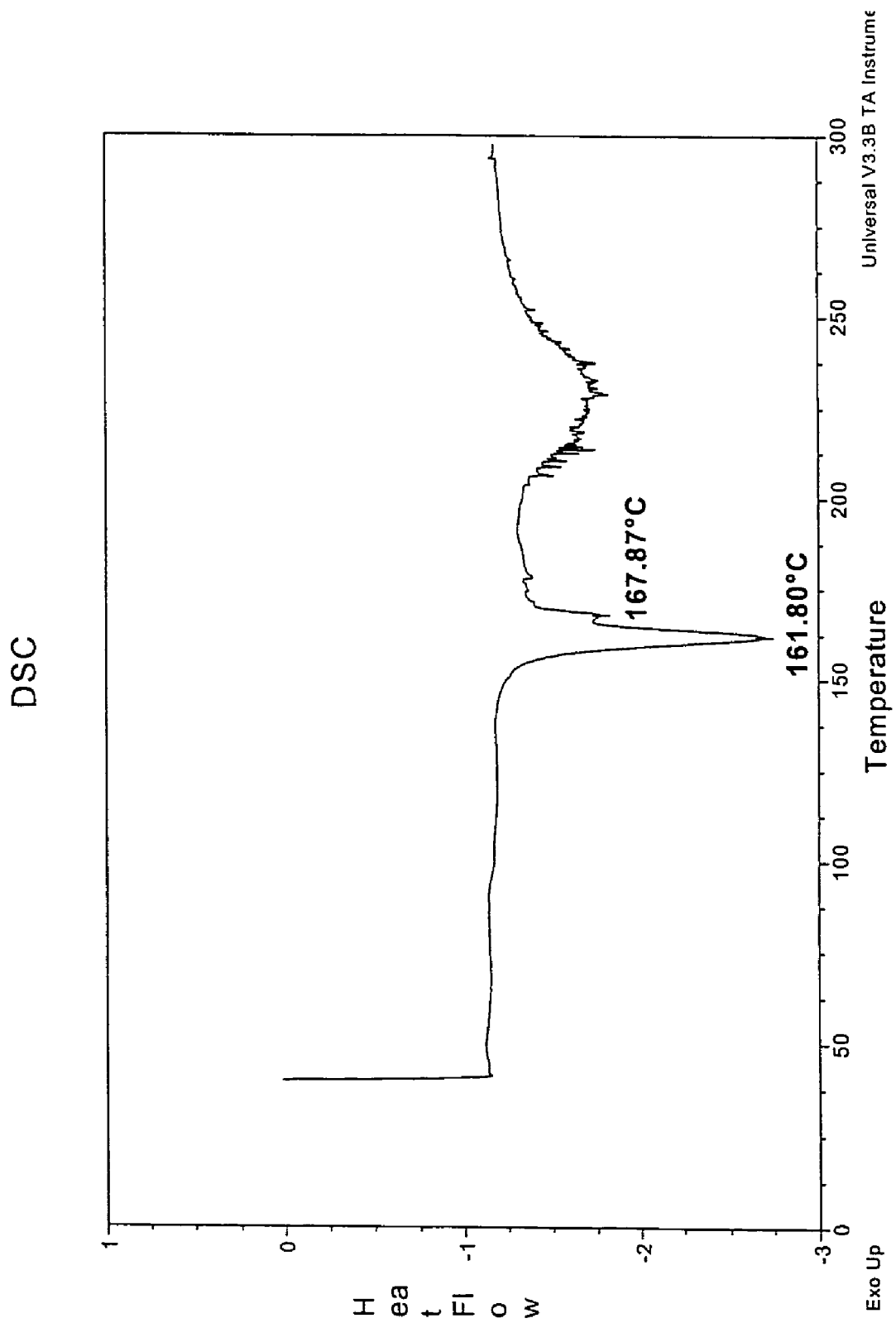
FIG. 3(a)-(d) illustrate the following:
(a) DSC measurements of the acid salt cis-itraconazole HCl salt tartaric acid co-crystal taken from room temperature to 300° C. at 10° C./minute;
(b) TGA of the acid salt cis-itraconazole HCl salt tartaric acid co-crystal taken from room temperature to 300° C. at 10° C./minute;
(c) PXRD measurements of the acid salt cis-itraconazole HCl salt tartaric acid co-crystal; and
(d) Raman spectroscopic measurements of the acid salt cis-itraconazole HCl salt tartaric acid co-crystal.
Figure 3B:
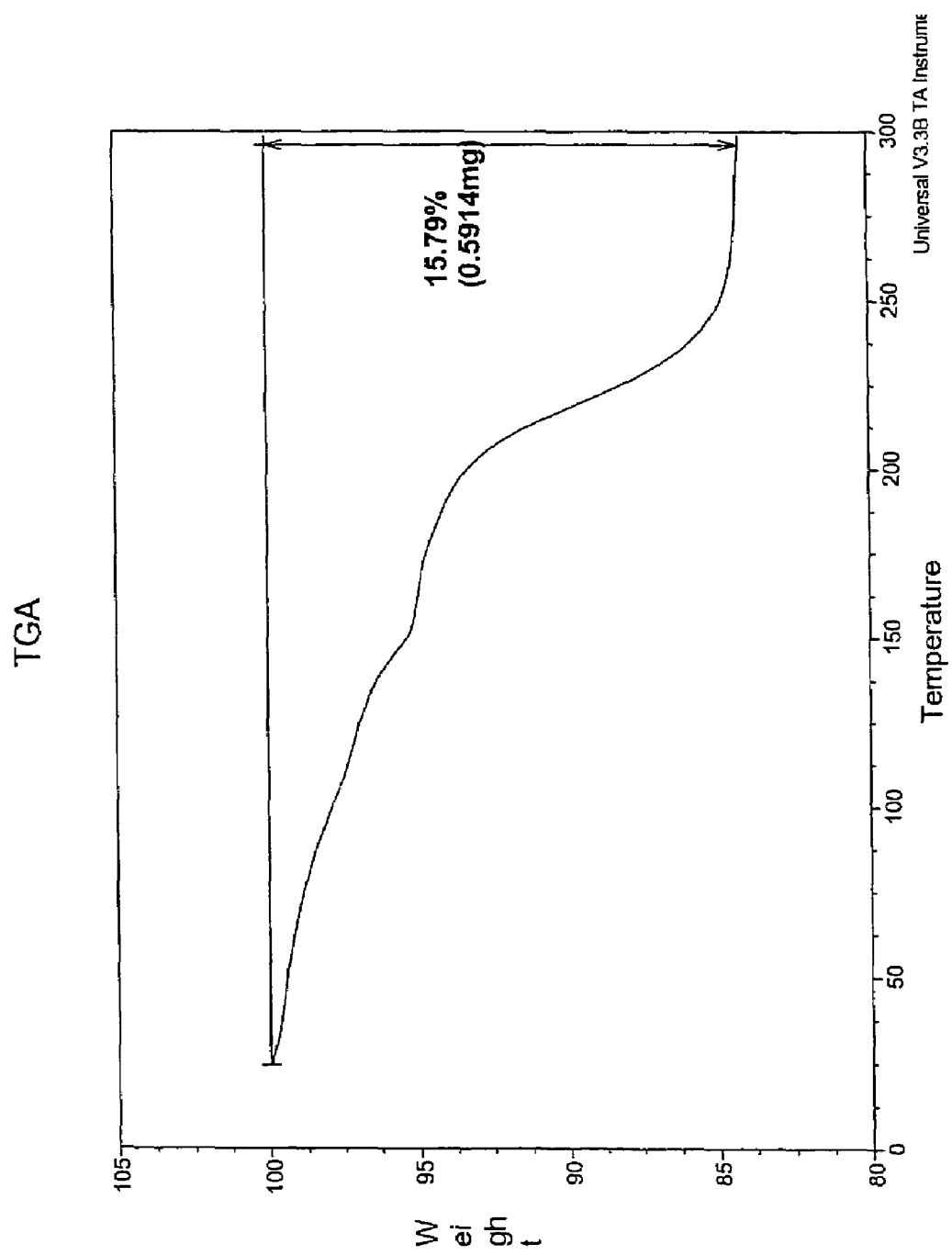

TGA of a sample of this cis-itraconazole HCl salt tartaric acid co-crystal (designated MM 109_38) was performed by placing 3.75 mg of sample in the sample pan. The starting temperature was 25° C. with a heating rate of 10° C./minute, and the ending temperature was 300° C. DSC analysis of the sample was performed by placing 1.508 mg of sample in an aluminum pan with a press fitted pan closure, and Tmin was 30° C. and $T_{max}$ was 300° C. TGA results for this sample are illustrated in FIG. 3(b). DSC results for the sample are illustrated in FIG. 3(a).

A sample of the compound appeared as hexagonal plates before filtration. After filtration and drying the sample appeared to be birifringent chunks by polarized light microscopy. The sample contained less than 0.1% volatile components by weight by TGA. The sample has an endothermic melting point transition at 162° C.±1.0° C.

Figure 3C:
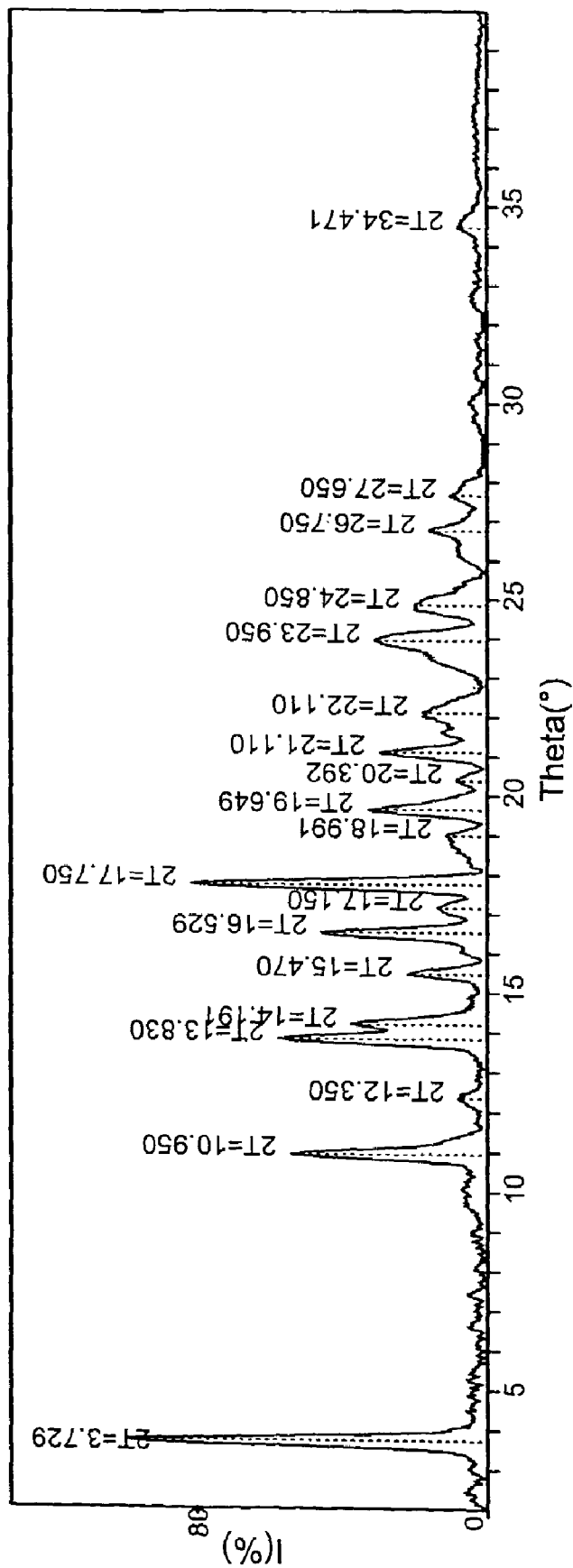

The sample was also examined by PXRD using a collection time of 10 minutes. Results of this measurement are illustrated in FIG. 3(c). The PXRD pattern for the cis-itraconazole HCl salt tartaric acid co-crystal has a powder X-ray diffraction pattern with identifying features that include those listed below in Table 15:

TABLE 15

| Cis-Itraconazole HCl salt Tartaric acid co-crystal | |
|---|---|
| 2-theta | Relative Intensity |
| 3.7 | S |
| 11.0 | M |
| 13.8 | M |
| 16.5 | M |
| 17.8 | S |

Figure 3D:
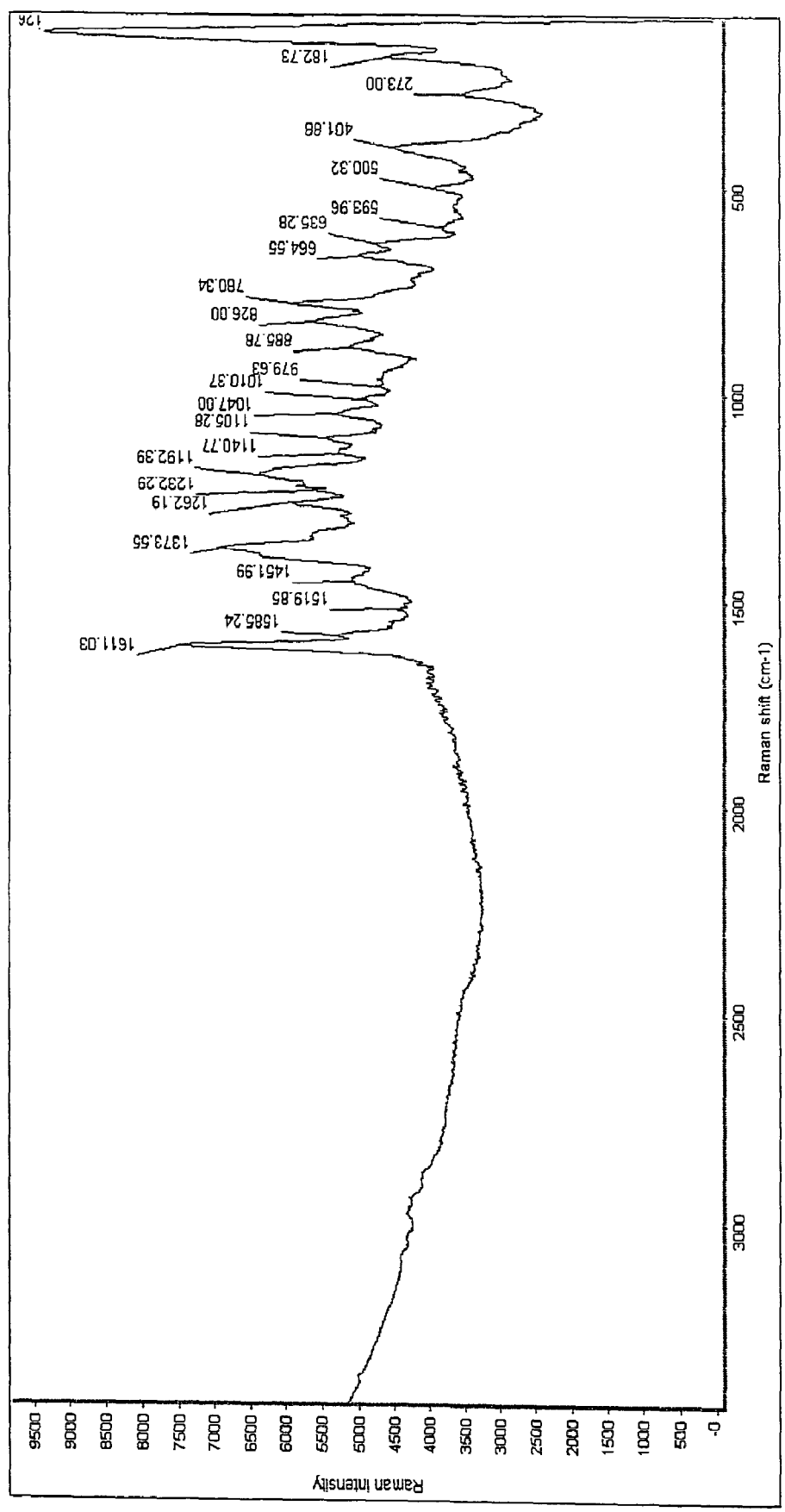

The results of Raman spectroscopic analysis of the sample are illustrated in FIG. 3(d).

Example 14

Synthesis and Analysis of Cis-Itraconazole Di-Mesylate, Dioxane Multicomponent Crystal System Approximately 2.04 g of 99% methanesulfonic acid dissolved in 100 mL of hot dioxane were added to a stirred mixture of 10.0 g of cis-itraconazole dissolved in 100 mL of hot dioxane. After the addition of the methanesulfonic acid was complete, the reaction mixture was seeded with a previous preparation of the mesylate salt and left to stir for 15 min until a thick slurry had formed. Three 100 mL aliquots of isopropyl acetate were added and the solution continued to stir for 1 hour. The crystals were harvested by vacuum filtration on a Buchner funnel with #4 Whatman filter paper, washed 3× with 5 mL aliquots of isopropyl acetate, and left in the hood to air dry overnight. Approximately 9.9 g of a cis-itraconazole di-mesylate dioxane multicomponent crystal system were obtained.

Figure 4A:
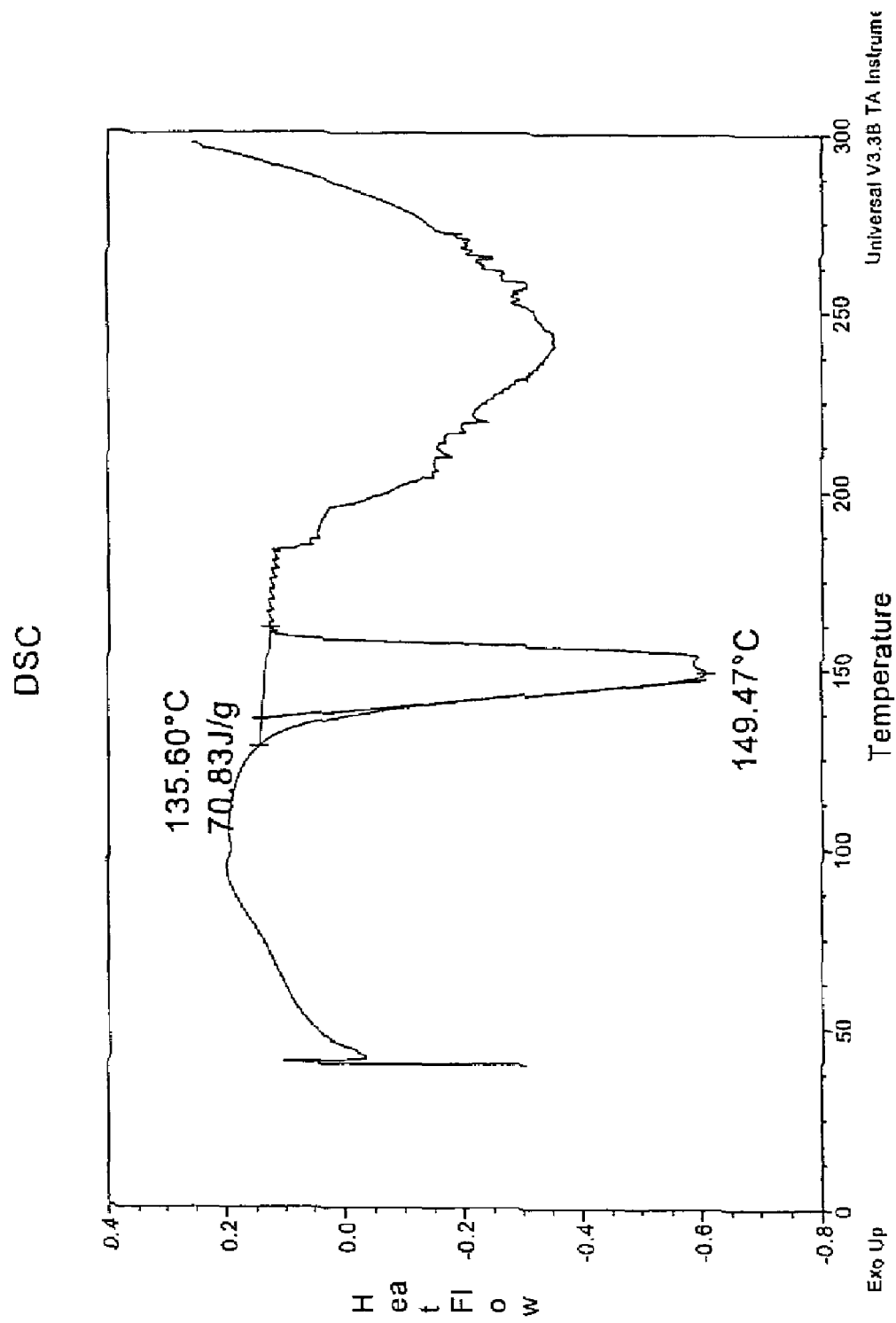
FIG. 4(a)-(d) illustrate the following:
(a) DSC measurements of a crystalline form of a soluble, multicomponent crystalline system comprising cis-itraconazole di-mesylate and dioxane taken from room temperature to 300° C. at 10° C./minute.
(b) TGA of a crystalline form of a soluble, multicomponent crystalline system comprising cis-itraconazole di-mesylate and dioxane taken from room temperature to 300° C. at 10° C./minute.
(c) PXRD measurements of a soluble, multicomponent crystalline system comprising cis-itraconazole di-mesylate and dioxane; and
(d) Raman spectroscopic measurements of a soluble, multicomponent crystalline system comprising cis-itraconazole di-mesylate and dioxane.
Figure 4B:
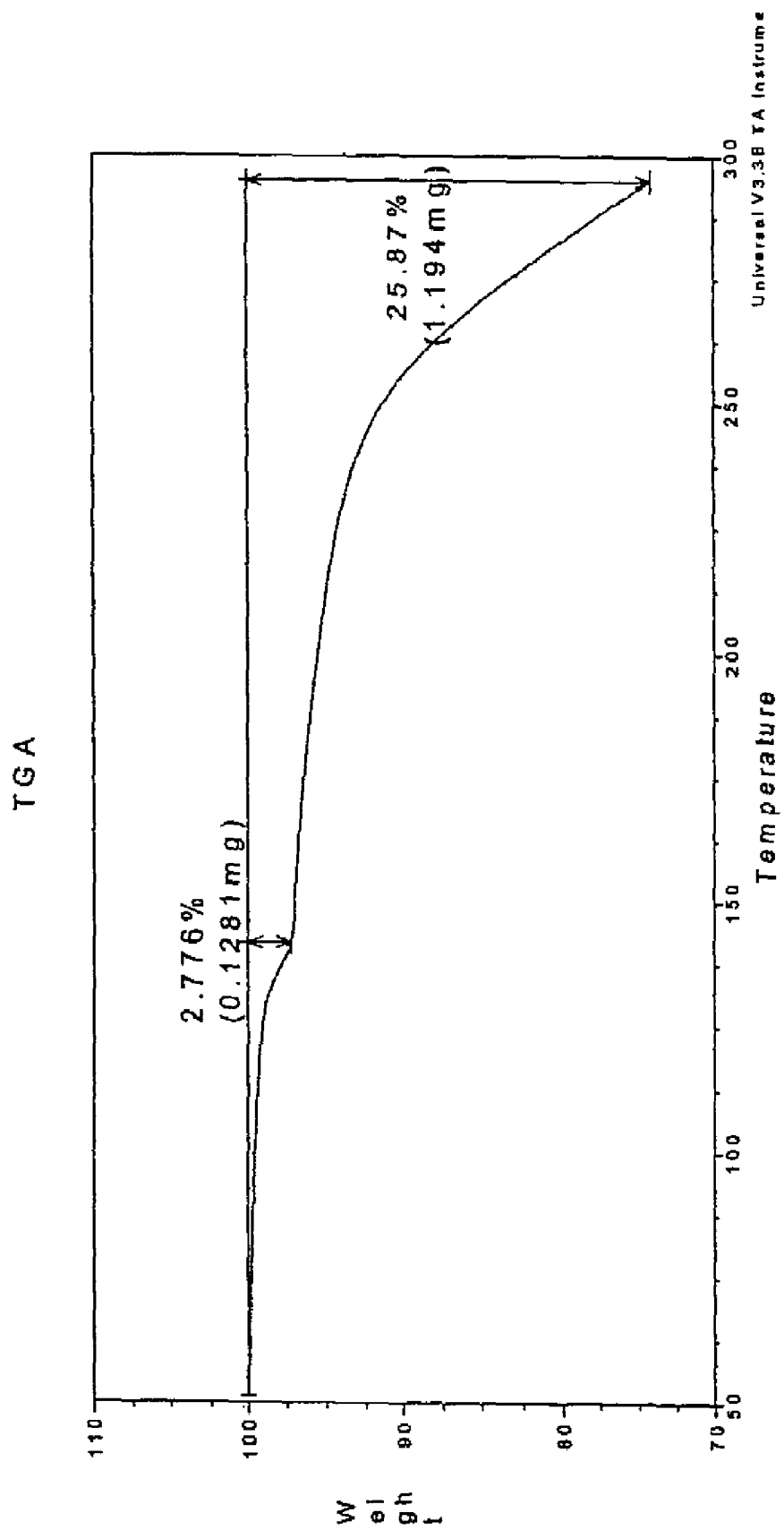

TGA of a sample (cis-itraconazole di-mesylate dioxane multicomponent crystal system, sample MM_109_46) was performed by placing 4.62 mg of sample in the sample pan. The starting temperature was 25° C. with a heating rate of 10° C./minute, and the ending temperature was 300° C. DSC analysis of a sample from this Example 14 was performed by placing 2.098 mg of sample in an aluminum pan with a press fitted pan closure, and $T_{min}$ was 30° C. and $T_{max}$ was 300° C. TGA results for this Example 14 are illustrated in FIG. 4(b). DSC results for the sample are illustrated in FIG. 4(a).

The sample appeared as wispy needles by polarized light microscopy. The sample contained less than 0.1% volatile components by weight by TGA. The sample has an endothermic melting point transition at 149° C.±1.0° C.

Figure 4C:
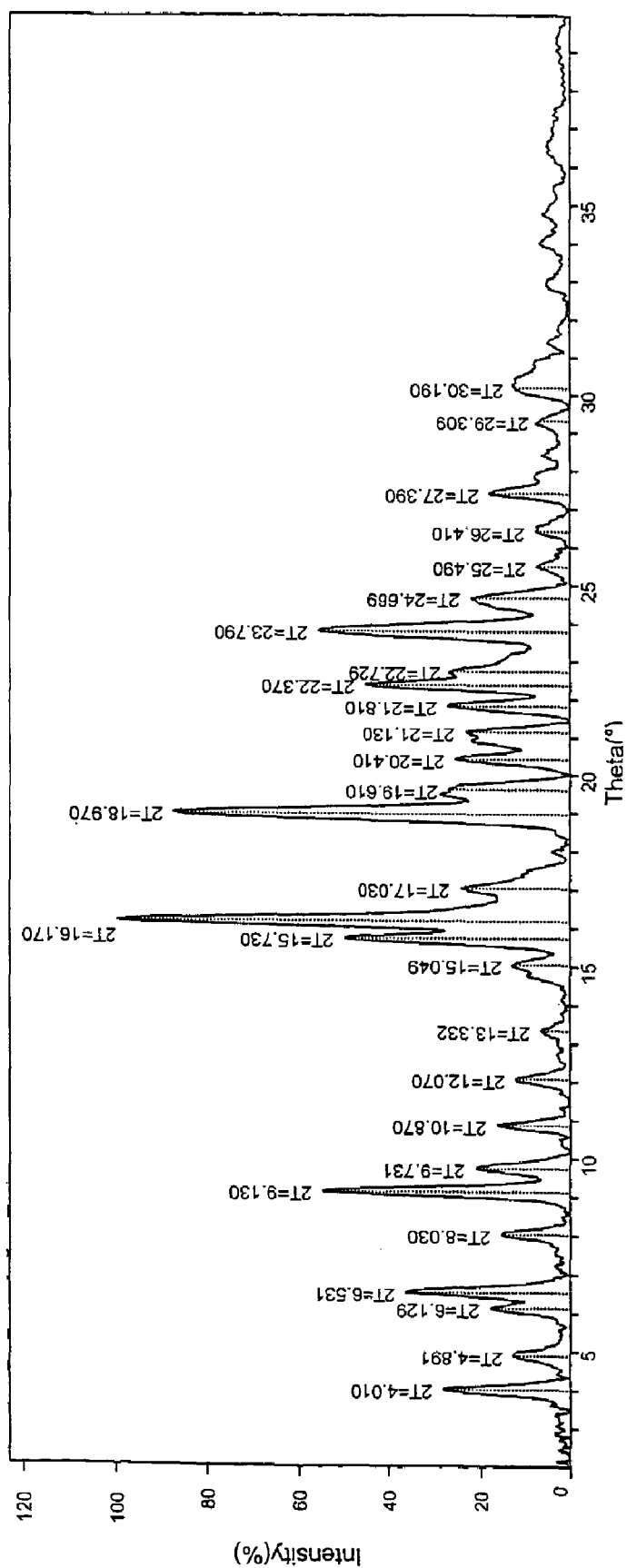

The sample was examined by PXRD using a collection time of 10 minutes. Results of this measurement are illustrated in FIG. 4(c). The PXRD pattern for the cis-itraconazole di-mesylate dioxane crystal system has a powder X-ray diffraction pattern with identifying features that include those listed below in Table 16:

TABLE 16

| Cis-Itraconazole Di-Mesylate Dioxane Crystal System | |
|---|---|
| 2-theta | Relative Intensity |
| 6.5 | M |
| 9.1 | M |
| 16.2 | S |
| 19.0 | S |
| 22.4 | M |
| 23.8 | M |

Figure 4D:
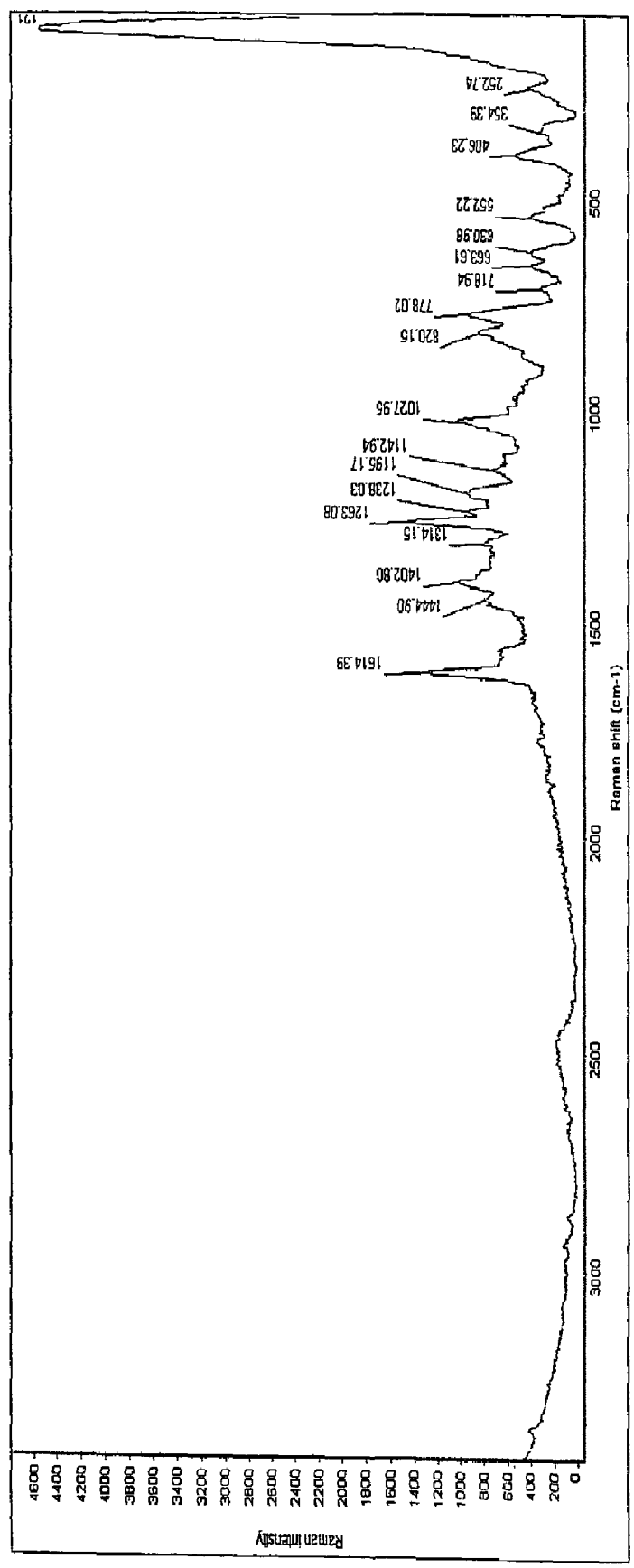

The results of Raman spectroscopic analysis of the cis-itraconazole di-mesylate dioxane multicomponent crystalline system sample are illustrated in FIG. 4(d).

Example 15

Synthesis and Analysis of Itraconazole Di-Mesylate Ethanol Multicomponent Crystal System Methods and Materials:

Cis-itraconazole di-mesylate ethanol multicomponent crystal systems are prepared by adding 1.5 molar equivalents of methanesulfonic acid dissolved in absolute ethanol to cis-itraconazole freebase suspended in absolute ethanol dropwise with stirring. Upon the formation of crystals, isopropyl acetate is added as an antisolvent to increase yield. Crystals are isolated by vacuum filtration and can be dried at 40° C. under a vacuum or left open at room temperature.

Syntheses:

(1): Cis-itraconazole freebase was suspended in absolute ethanol at 63 mg/mL with stirring. 1.5 molar equivalents of methanesulfonic acid were dissolved in 1 mL of absolute ethanol and added to the freebase suspension dropwise with stirring at room temperature. The solution cleared upon addition of the methanesulfonic acid and was filtered. The solution was then seeded with crystals from a previous batch of the mesylate ethanolate with stirring. After 15 min, a thick slurry of crystals had formed. 15 mL if isopropyl acetate was added and the solution was left to stir for another 30 min. The cis-itraconazole di-mesylate ethanol multicomponent crystals were isolated by vacuum filtration on a Hirsch funnel. The yield was 80.7%.

(2): Approximately 1.36 g of 99% methanesulfonic acid dissolved in 50 mL of room temperature absolute ethanol were added to a stirred mixture of 5.0 g of cis-itraconazole suspended in room temperature absolute ethanol in a 500 mL Erlenmeyer flask. After the addition of the methanesulfonic acid was complete, the reaction mixture was seeded with a previous preparation of the mesylate salt and left to stir for 15 min until a thick slurry had formed. Three 100 mL aliquots of isopropyl acetate were added and the solution continued to stir for 2 hours. The crystals were harvested by vacuum filtration on a Buchner funnel with #4 Whatman filter paper, washed 3× with 5 mL aliquots of isopropyl acetate, and left in the hood to air dry overnight. Approximately 5.4 g of a crystalline form of an ethanol solvate of cis-itraconazole di-mesylate ethanol multicomponent crystals were obtained.

Characterization of Crystal System Prepared in Synthesis (1):

Microscope Images:

The cis-itraconazole di-mesylate ethanol multicomponent crystals were suspended in isopropyl acetate before filtration. Crystals appear to be thin wispy needles.

Figure 5A:
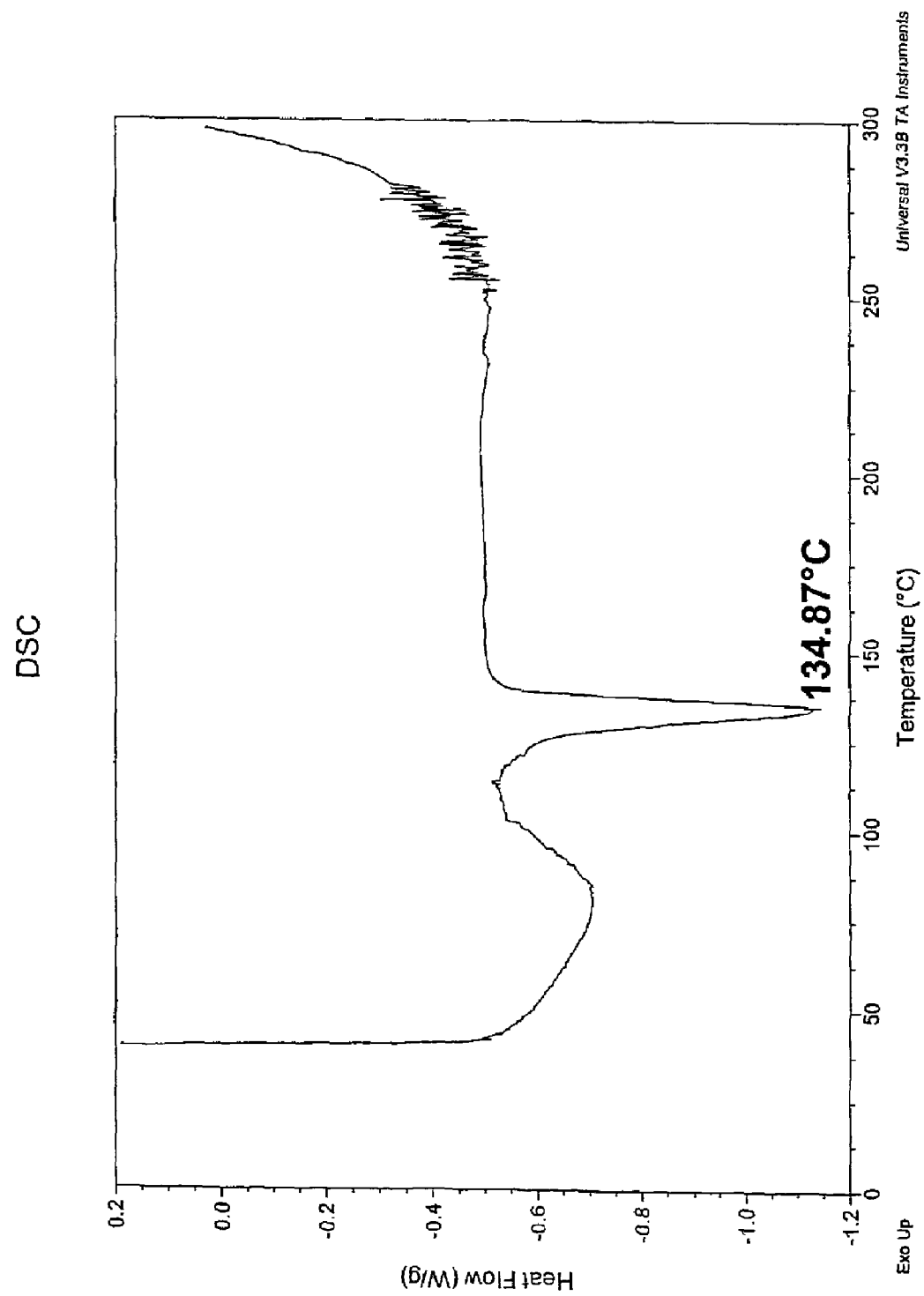
FIG. 5(a)-(f) illustrate the following:
(a) DSC measurements of a crystalline form of a soluble, multicomponent crystalline system comprising cis-itraconazole di-mesylate and ethanol taken from room temperature to 300° C. at 10° C./minute.
(b) TGA of a crystalline form of a soluble, multicomponent crystalline system comprising cis-itraconazole di-mesylate and ethanol taken from room temperature to 300° C. at 10° C./minute;
(c) TGA of a crystalline form of a soluble, multicomponent crystalline system comprising cis-itraconazole di-mesylate and ethanol taken from room temperature to 300° C. at 10° C./minute;
(d) PXRD measurements of a soluble, multicomponent crystalline system comprising cis-itraconazole di-mesylate and ethanol;
(e) PXRD measurements of a soluble, multicomponent crystalline system comprising cis-itraconazole di-mesylate and ethanol;
(f) Raman spectroscopic measurements of a soluble, multicomponent crystalline system comprising cis-itraconazole di-mesylate and ethanol.

FIG. 5(a) illustrates cis-itraconazole di-mesylate ethanol multicomponent crystals after filtration and drying. Image taken using plane polarized light through a first order red plate at 20× Crystals appear as clumped thin needles.

Figure 5B:
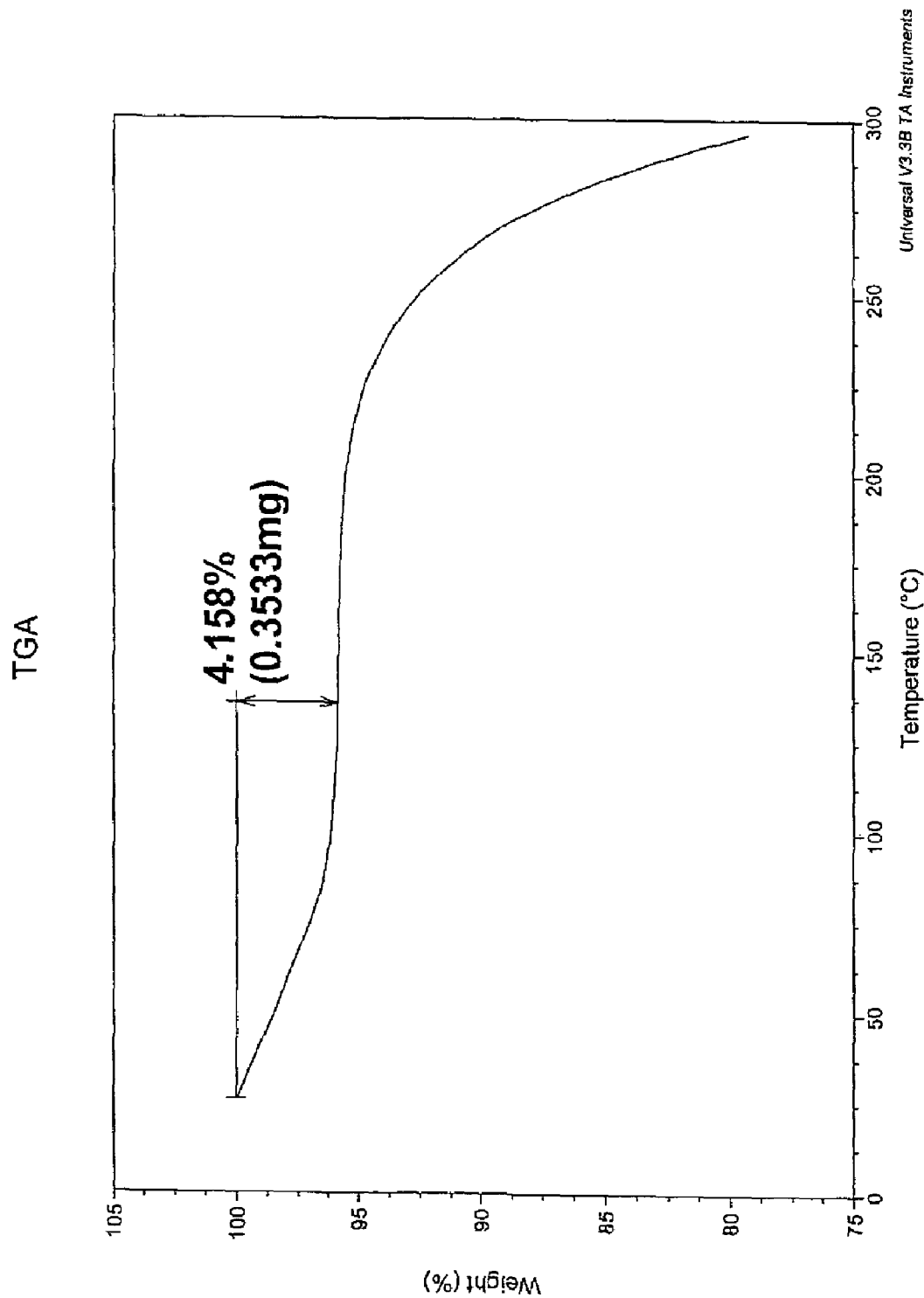

DSC:

FIG. 5(b) illustrates a large melting point endotherm at 135° C. for a 0.993 mg sample taken from room temperature to 300° C. at 10° C./min in a closed, aluminum DSC pan.

Figure 5C:
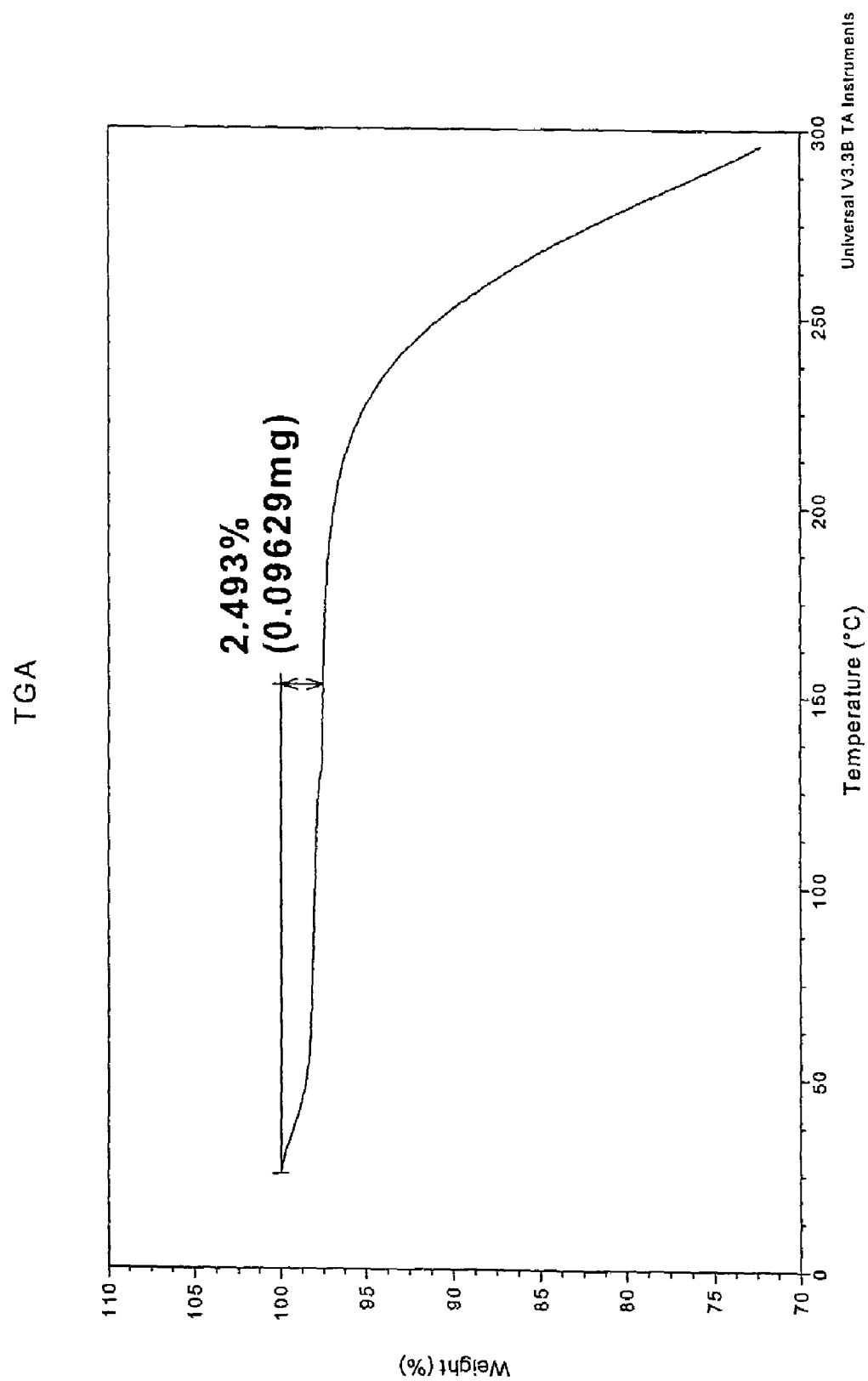

TGA:

FIG. 5(c) illustrates TGA of freshly isolated sample, air-dried for 1 hour before running. FIG. 5(c) shows a weight loss of 4.158% between room temperature and 150° C. corresponding to nearly 1 equivalent of ethanol. See FIG. 5(e) for the PXRD pattern for this sample. In the TGA illustrated in FIG. 5(c), an 8.496 mg sample was taken from room temperature to 300° C. at 10° C./min in a platinum pan.

Figure 5D:
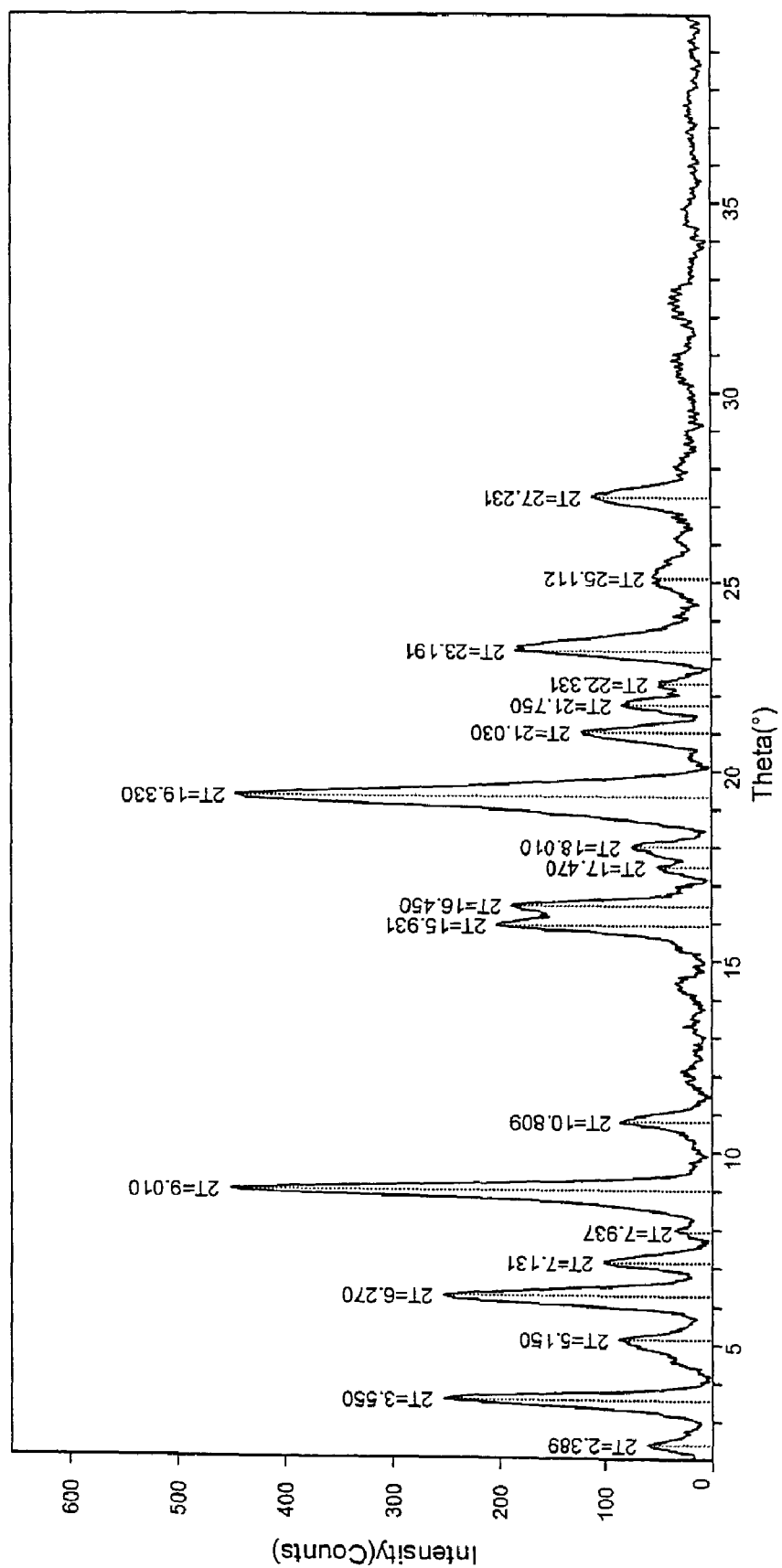
Figure 5E:
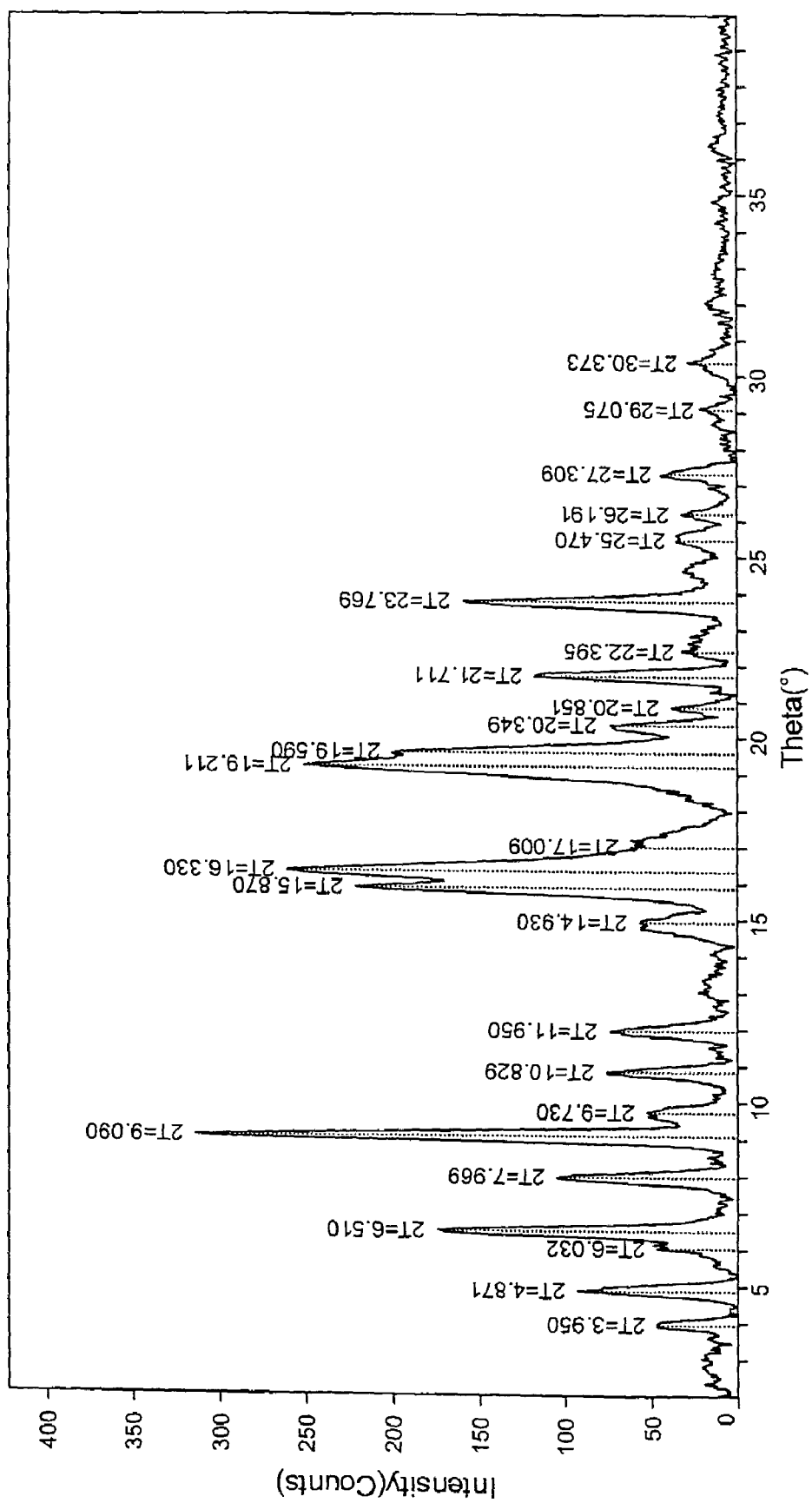

FIG. 5(d) illustrates TGA of a sample dried overnight in a vacuum oven at 40° C. FIG. 5(e) shows a weight loss of 2.493% between room temperature and 150° C. corresponding to ½ equivalent of ethanol. See FIG. 5(f) for the PXRD pattern for this sample. In the TGA illustrated in FIG. 5(d), a 3.863 mg sample taken from room temperature to 300° C. at 10° C./min in a platinum pan.

PXRD:

FIG. 5(e) illustrates PXRD of cis-itraconazole di-mesylate ethanol crystal systems corresponding to TGA in FIG. 5(e). Characteristic reflections in 2-theta were determined at: 3.6, 6.3, 7.3, 9.0, 10.9, 15.9, 16.5, 19.3, 21.0, 23.2.

Figure 5F:
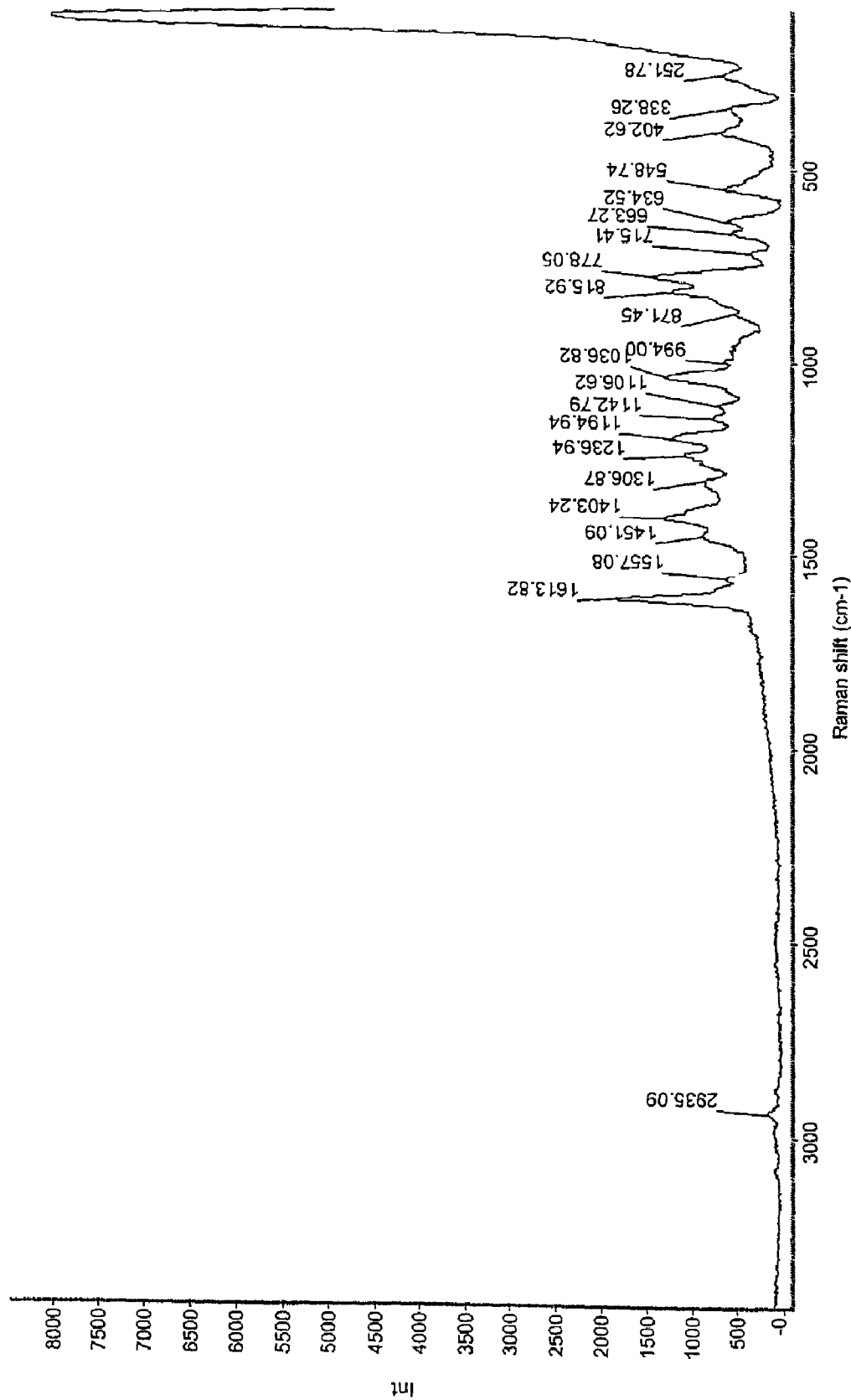

FIG. 5(f) illustrates PXRD of cis-itraconazole di-mesylate ethanol multicomponent crystals corresponding to TGA in FIG. 5(d). Characteristic reflections in 2-theta were determined at: 4.0, 4.9, 6.5, 8.0, 9.0, 9.7, 10.8, 12.0, 14.9, 15.9, 16.3, 19.2, 19.6, 21.7, 23.8. Representative intensity values for some of these values are listed below in Table 17.

Raman:

FIG. 5(g) illustrates Raman spectrum of cis-itraconazole di-mesylate ethanol multicomponent crystals with characteristic absorptions in cm$^{-1}$ at 1614, 1403, 1237, 1195, 1037, 816, 778, 663, 635, 549, 403, 338 and no absorptions at 1262 or 593.

TABLE 17

| Cis-Itraconazole Mesylate Ethanolate | |
|---|---|
| 2-theta | Relative Intensity |
| 6.5 | M |
| 9.0 | S |
| 16.3 | S |
| 19.2 | S |

TABLE 17-continued

| Cis-Itraconazole Mesylate Ethanolate | |
|---|---|
| 2-theta | Relative Intensity |
| 21.7 | M |
| 23.8 | M |

Example 16

Cis-Itraconazole DI-Mesylate Ethanol Multicomponent Crystal System Dilution Testing A sample of cis-itraconazole di-mesylate ethanol multicomponent crystals of Example 15 (designated as TPI 315; sample MM_109_121_A) was determined by the PXRD and Raman analysis described in Example 15 to have a composition and average molecular weight as set forth in the following Table 18.

TABLE 18

|  | # | mass | total |
|---|---|---|---|
| TPI-315 | | | |
| C | 35 | 12.01 | 420.37 |
| H | 38 | 1.01 | 38.30 |
| Cl | 2 | 35.45 | 70.91 |
| N | 8 | 14.01 | 112.05 |
| O | 4 | 16.00 | 64.00 |
| | | MW | 705.63 |
| methanesulfonic acid | | | |
| C | 1 | 12.01 | 12.01 |
| H | 4 | 1.01 | 4.03 |
| O | 3 | 16.00 | 48.00 |
| S | 1 | 32.07 | 32.07 |
| | | MW | 96.11 |
| Ethanol | | | |
| C | 2 | 12.01 | 24.02 |
| H | 6 | 1.01 | 6.05 |
| O | 1 | 16.00 | 16.00 |
| | | MW | 46.07 |

Approximately 12.62 g of sample was dissolved in 50 mL of 50:50 water:acetonitrile (25 mL acetonitrile added first), to make a 252.4 ug/mL solution of the sample. This was serially diluted 10× each to make two other dilutions. These three dilutions were run alongside standards of TPI-315 prepared in the same fashion in 2.514, 25.14, and 251.4 ug/mL concentrations. Concentration values for these three dilutions were determined to be as set firth in the following Table 19.

TABLE 19

| TPI-315 recovered | |
|---|---|
| Dilution 1 | 2.524 ug/mL |
| Concentration | 2.221 ug/mL |
| TPI-315 in sample | 11.105 mg |
| % TPI-315 (mass) | 88.0% |
| % unknown (mass) | 12.0% |
| mass unknown | 1.515 mg |
| Dilution 2 | 25.24 ug/mL |
| concentration | 20.12 ug/mL |
| TPI-315 in sample | 10.058 mg |
| % TPI-315 (mass) | 79.7% |

TABLE 19-continued

| | |
|---|---|
| % unknown (mass) | 20.3% |
| mass unknown | 2.563 mg |
| Dilution 3 | 252.4 ug/mL |
| concentration | 197.8 ug/mL |
| TPI-315 in sample | 9.891 mg |
| % TPI-315 (mass) | 78.4% |
| % unknown (mass) | 21.6% |
| mass unknown | 2.729 mg |
| Average of Three Dilutions | |
| TPI-315 in sample | 10.351 mg |
| % TPI-315 (mass) | 82.0% |
| % unknown (mass) | 18.0% |
| mass unknown | 2.269 mg |

TGA data of the sample of the sample shows that 2.492% of the sample is residual solvent (ethanol). This allows the values for the unknown to be split into residual solvent and unknown. The total mass of the sample was then determined to be as shown in Table 20.

TABLE 20

Average of Three Dilutions

| | |
|---|---|
| TPI-315 in sample | 10.351 mg |
| % TPI-315 (mass) | 82.0% |
| % unknown (mass) | 15.5% |
| % ethanol (mass) | 2.5% |
| mass unknown | 1.954 mg |
| mass of sample | 12.306 mg |

Using the mass data of Table 20, the moles of TPI-315 were used to determine the molecular weight of the sample, which is set forth in Table 21.

TABLE 21

| | |
|---|---|
| mass TPI-315 | 10.351 mg |
| MW TPI-315 | 705.63 g/mol |
| moles TPI-315 | 0.015 mmol |
| mass sample | 12.306 mg |
| moles sample | 0.015 mmol |
| MW sample | 838.85 g/mol |

Example 17

Synthesis and Analysis of Cis-Itraconazole Tosylate

Approximately 82.24 mg of cis-itraconazole and 22.39 mg of p-toluenesulfonic acid were dissolved in 4 mL of 1,2-dichloroethane. The sample was mixed and heated to 95 degrees C. and then incubated at RT. Resulting crystals were analyzed using TGA, DSC, and PXRD.

Figure 10A:
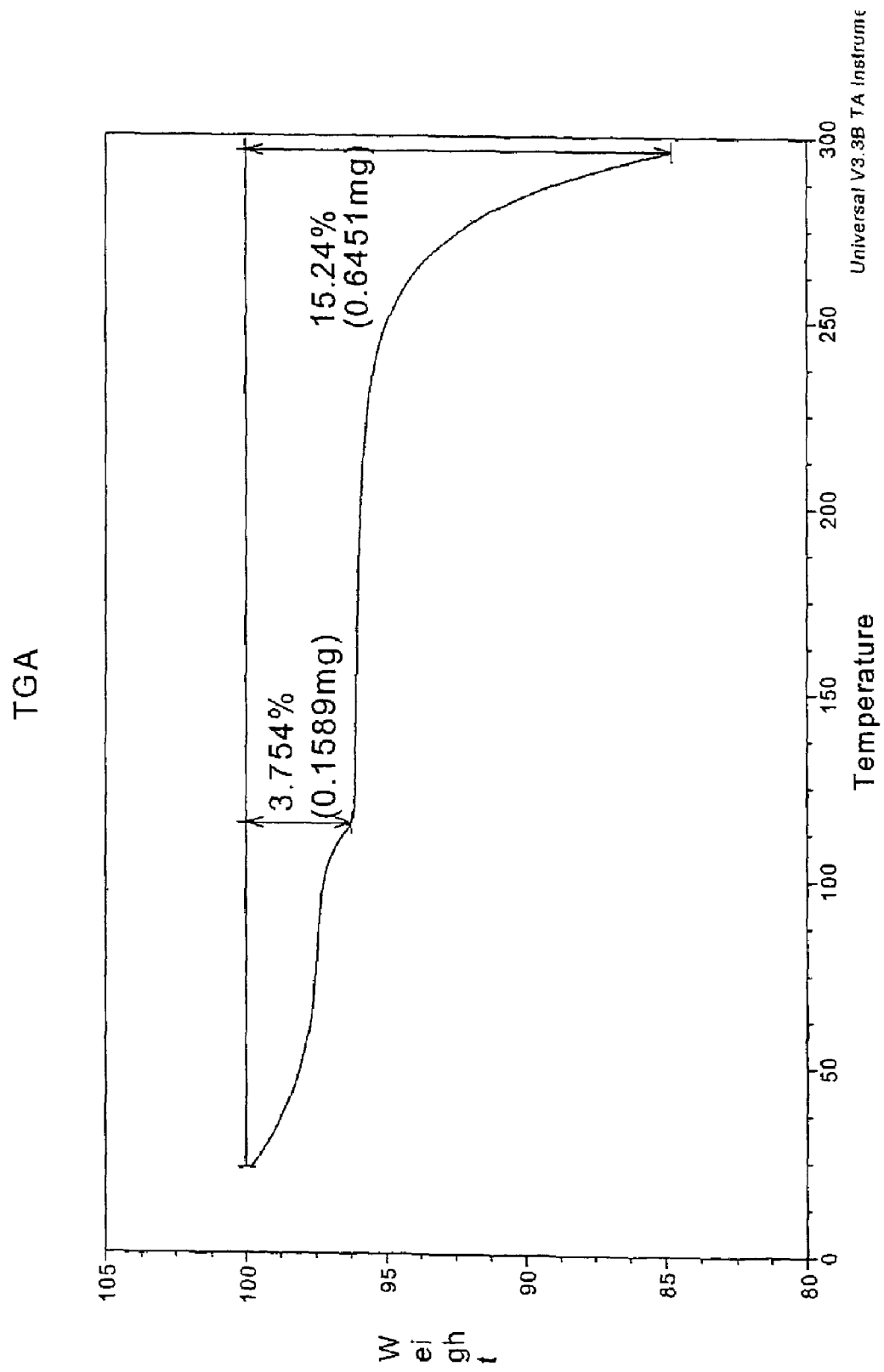
FIG. 10(a)-(c) illustrate the following:
(a) TGA of a crystalline form of a cis-itraconazole tosylate salt taken from room temperature to 300° C. at 10° C./minute.
(b) DSC measurements of a crystalline form of a cis-itraconazole tosylate taken from from room temperature to 300° C. at 10° C./minute.
(c) PXRD measurements of a crystalline form of a cis-itraconazole tosylate.

TGA of a sample of this cis-itraconazole tosylate (designated MM 109_43-I) was performed by placing 4.233 mg of sample in the sample pan. The starting temperature was 25° C. with a heating rate of 10° C./minute, and the ending temperature was 300° C. FIG. 10(a) shows a weight loss of 3.75% at 25 degrees C. to about 110 degrees C. and a 15.24% weight loss between 25 degrees C. and 300 degrees C.

Figure 10B:
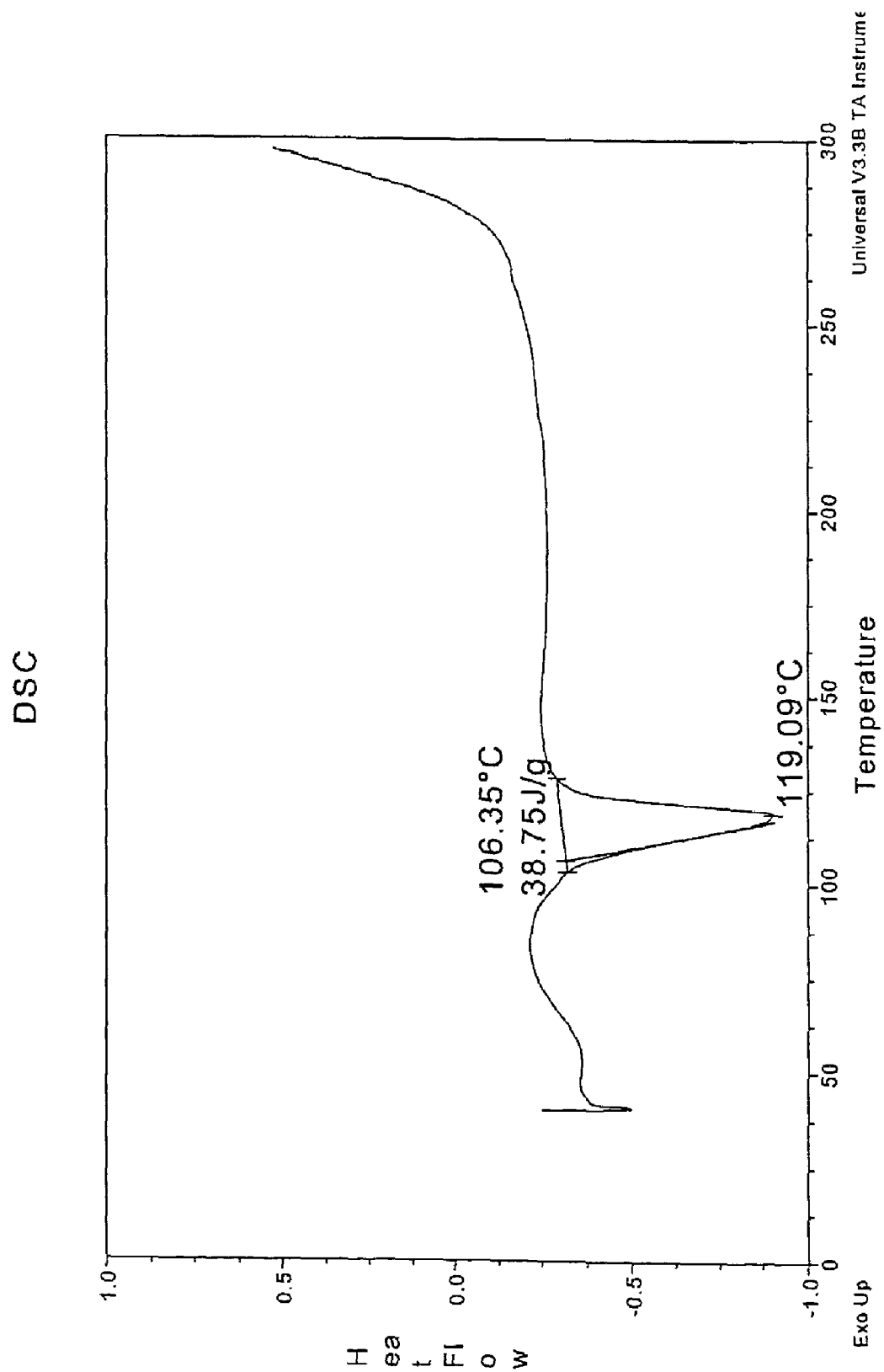

DSC analysis of the sample was performed by placing 1.127 mg of sample in an aluminum pan with a press fitted pan closure, and Tmin was RT and $T_{max}$ was 300° C. and the temperature was increased 10 degrees C./min. DSC results for the sample are illustrated in FIG. 10(b) and show a melting point of about 119.09 degrees C.

Figure 10C:
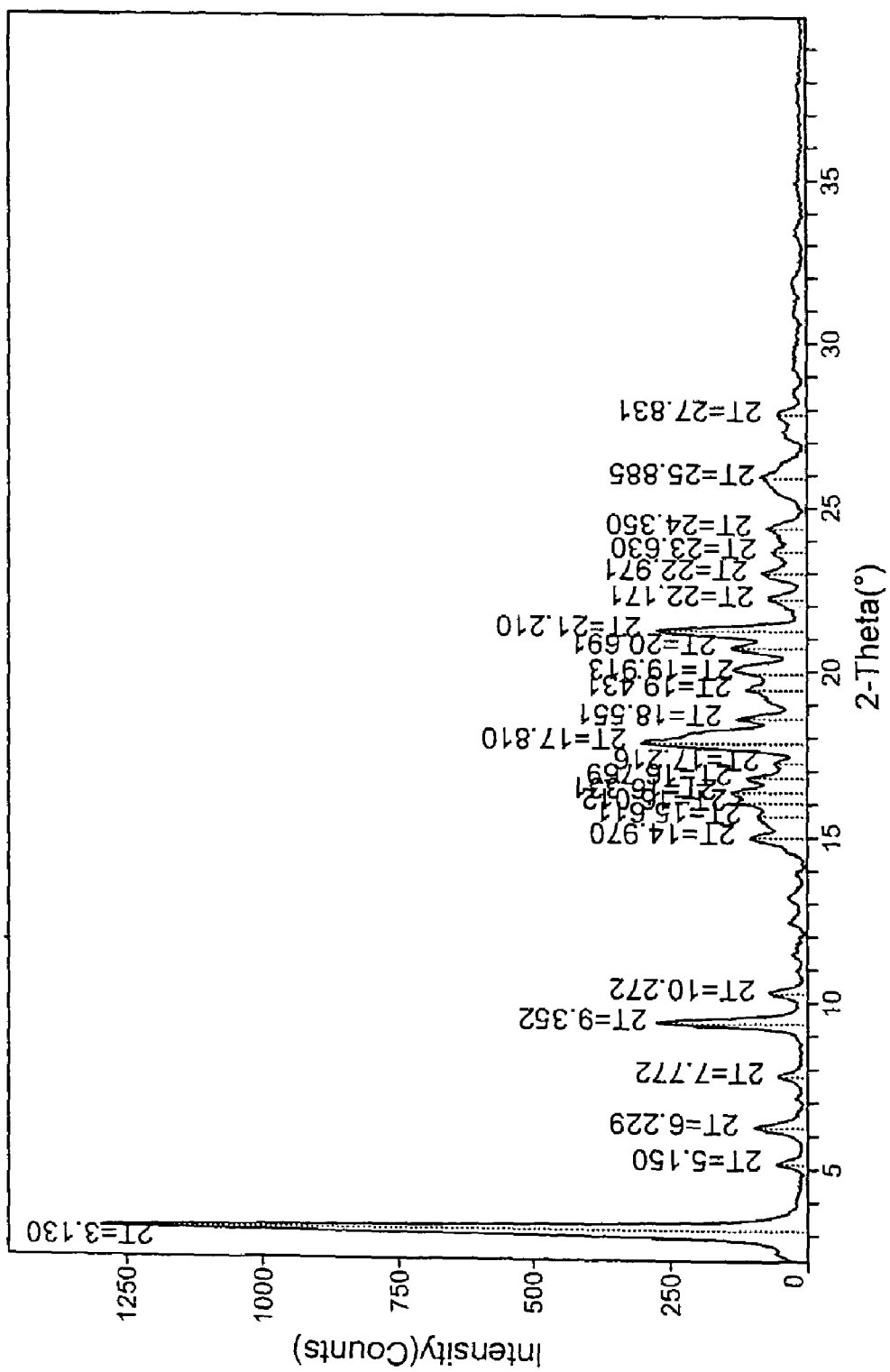

The sample was also examined by PXRD with the results shown in FIG. 10(c). The PXRD pattern for the cis-itraconazole tosylate has a powder X-ray diffraction pattern peaks at 2-theata angles including 3.1, 9.35, 17.8, and 21.2.

Example 18

Synthesis and Analysis of Cis-Itraconazole Tosylate Tartaric Acid Co-Crystal

Approximately 106.43 mg of cis-itraconazole, 22.63 mg of tartaric acid and 30.61 mg of p-toluenesulfonic acid were dissolved in 4 mL of 1,2-dichloroethane. The sample was mixed and heated to 95 degrees C. and then incubated at RT. Resulting crystals were filtered using t-BuOMe as an antisolvant and analyzed using TGA, DSC, and PXRD.

Figure 11A:
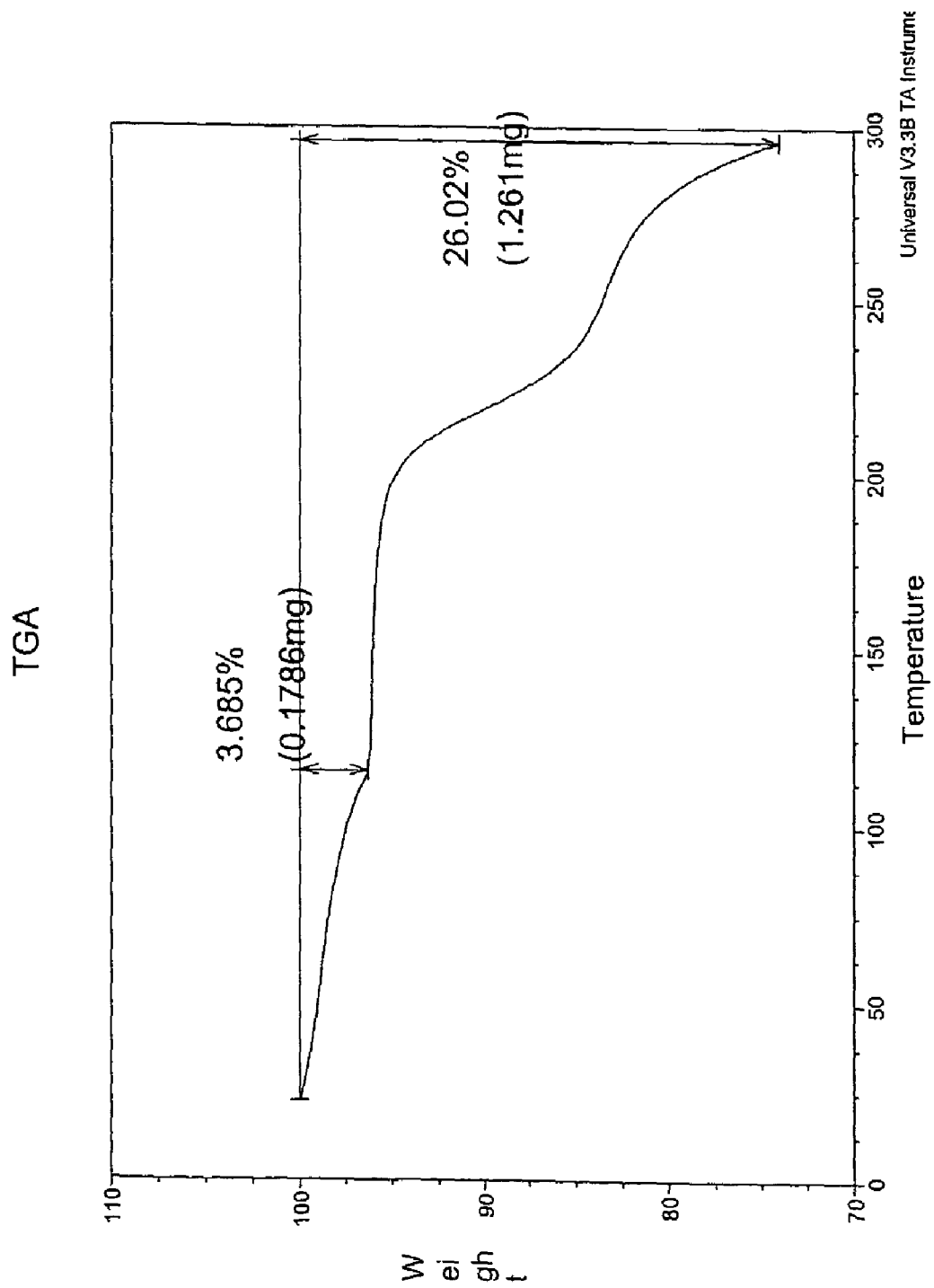
FIG. 11(a)-(c) illustrate the following:
(a) TGA of a crystalline form of a cis-itraconazole tosylate tartrate salt taken from room temperature to 300° C. at 10° C./minute.
(b) DSC measurements of a crystalline form of a cis-itraconazole tosylate tartrate taken from from room temperature to 300° C. at 10° C./minute.
(c) PXRD measurements of a crystalline form of a cis-itraconazole tosylate tartrate.

TGA of a sample of this cis-itraconazole tosylate tartaric acid (designated MM 109_48-B) was performed by placing 4.848 mg of sample in the sample pan. The starting temperature was 25° C. with a heating rate of 10° C./minute, and the ending temperature was 300° C. FIG. 11(a) shows a weight loss of 3.685% at 25 degrees C. to about 110 degrees C. and a 26.02% weight loss between 25 degrees C. and 300 degrees C.

Figure 11B:
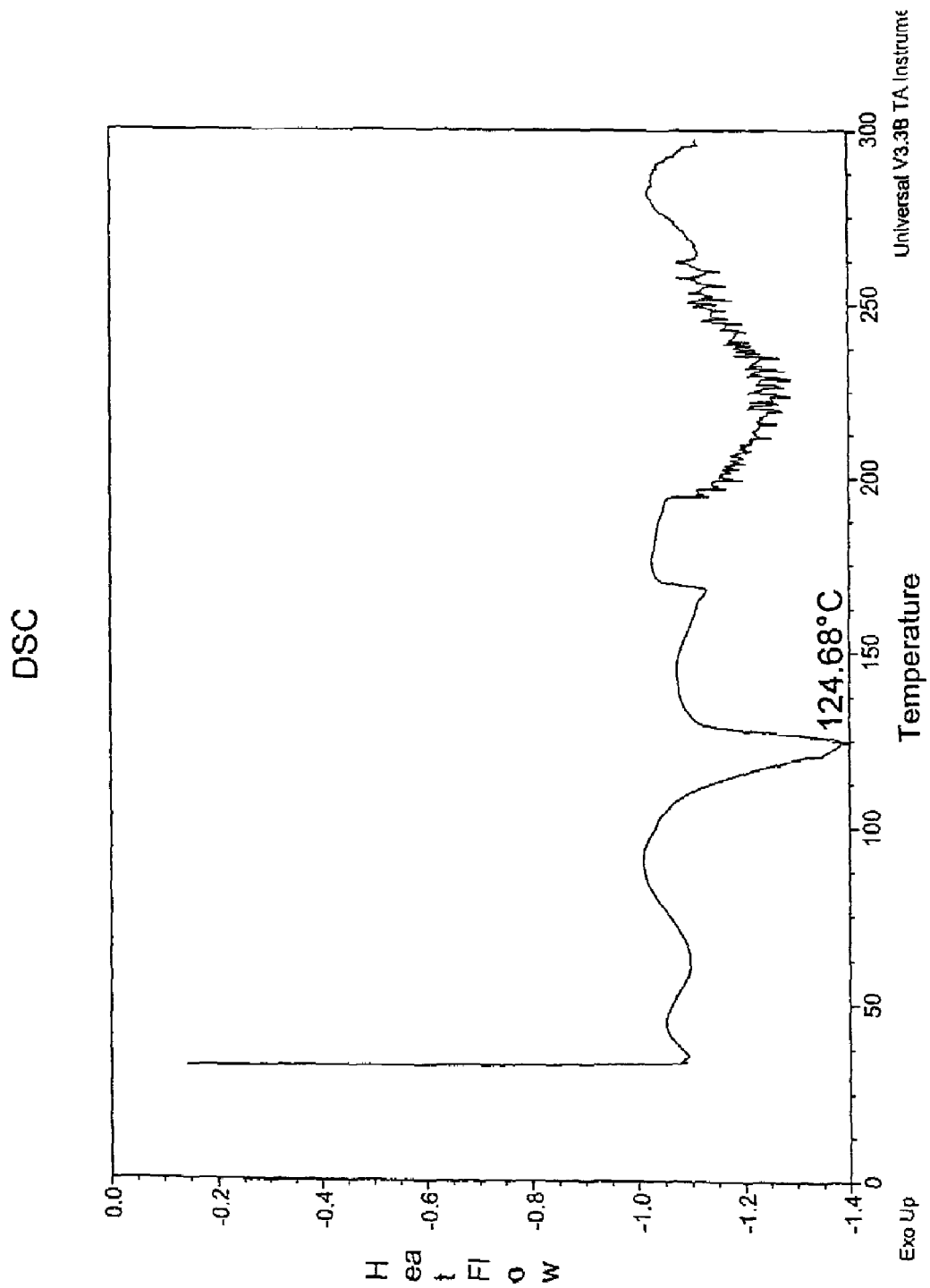

DSC analysis of the sample was performed by placing 1.97 mg of sample in an aluminum pan with a press fitted pan closure, and Tmin was RT and $T_{max}$ was 300° C. and the temperature was increased 10 degrees C./min. DSC results for the sample are illustrated in FIG. 11(b) and show a melting point of about 124.68 degrees C.

Figure 11C:
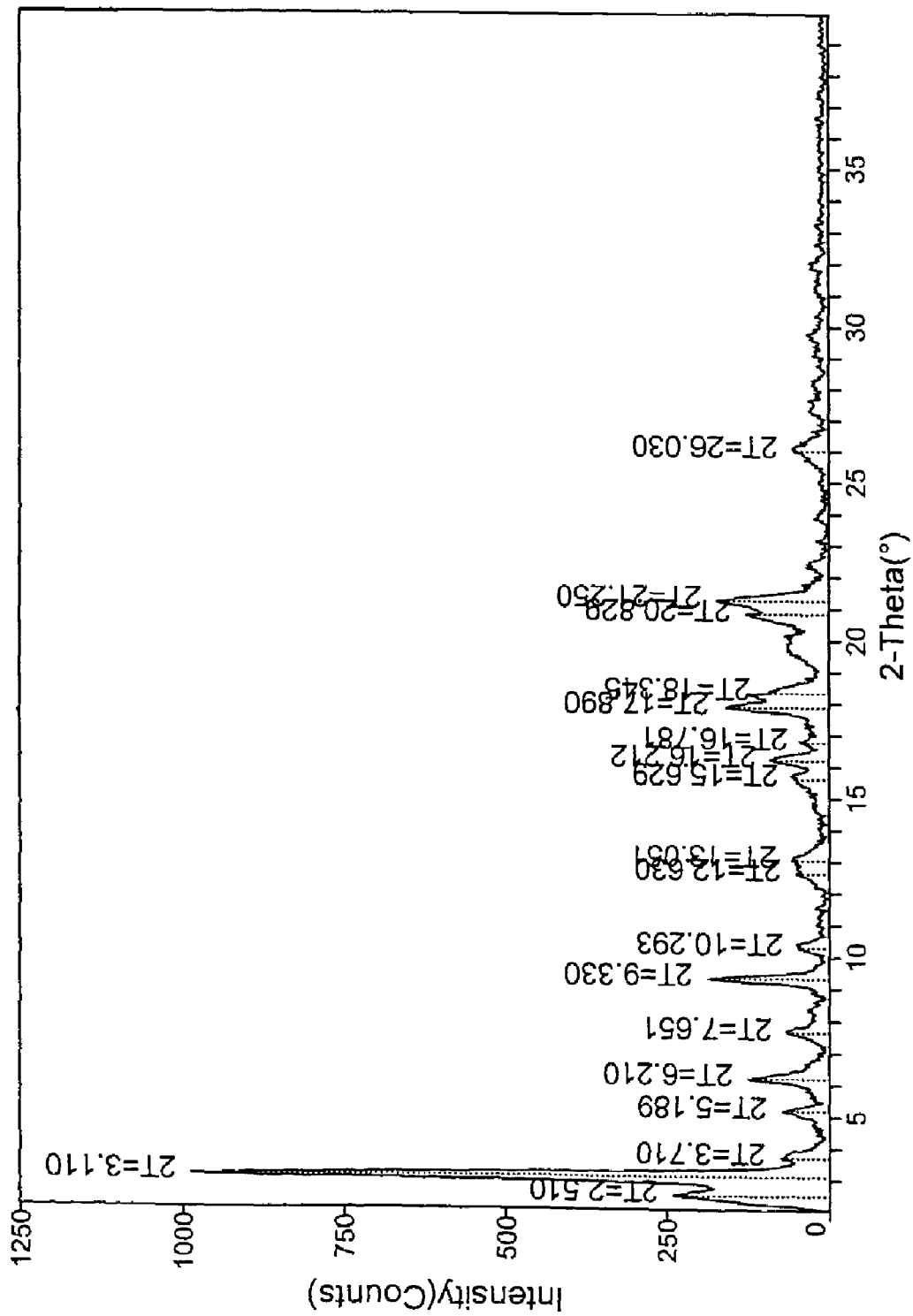

The sample was also examined by PXRD with the results shown in FIG. 11(c). The PXRD pattern for the cis-itraconazole tosylate tartrate has a powder X-ray diffraction pattern peaks at 2-theata angles including 3.11, 6.2, 9.3, 17.9, and 21.25.

Example 19

Synthesis of Posaconazole Co-Crystals

Preperation of posaconazole is known in the art: A. K. Saksena et al., WO 95 17407 and U.S. Pat. No. 5,661,151 (1995, 1997 both to Schering); *Tetrahedron Letters* 37, 5657 (1996); Tetrahedron Letters 43(18): 3359-3363 29 Apr., 2002 (each incorporated herein in their entireties). Comparative antifungal spectrum is disclosed in: A. Cacciapuoti et al., *Antimicrob. Ag. Chemother.* 44, 2017 (2000) (each incorporated herein in their entireties). Posaconazole pharmacokinetics in animals is disclosed in: A. A. Nomeir et al., *ibid.* 727. HPLC determn in serum: H. Kim et al., *J. Chromatog. B* 738, 93 (2000) (each incorporated herein in their entireties). Reviews of posaconazole development are disclosed in: A. K. Saksena et al. in *Anti-Infectives: Recent Advances in Chemistry and Structure Activity Relationships* (Royal Soc. Chem., Cambridge, 1997) pp 180-199 (each incorporated herein in their entireties).

Posaconazole is co-crystallized with di-carboxylic acids by adding the drug and 0.5-1.1 equiv of the di-carboxylic acid in a solvent such as THF or dioxane with or without heat. 0.5-10 volumes of an antisolvent such as isopropylacetate, ethylacetate, butylacetate, methylacetate, t-butyl methylether, pentane, hexane, heptane, or any other hydrocarbon or hindered ether or hindered acetate that is miscible with the THF or dioxane would be added to reduce the solubility. The solution is filtered if desirable. If co-crystals do not form after incubation, the solution is cooled. An alternative method is to template the co-crystals of posaconazole using a co-crystal of cis-itraconazole. Other polar aprotic solvents, such as DMF or NMP could potentially be used as the solvents. In another alternative method, instead of using an antisolvent, the solvent is cooled or evaporated to saturate the system.

Example 20

Synthesis of Saperconazole Crystals

Preperation of posaconazole is known in the art: J. Heeres et al., EP 283992; eidem, U.S. Pat. No. 4,916,134 (1988, 1990 both to Janssen) (each incorporated herein in their entireties). In vitro antifungal activity is described in: F. C. Odds, *J. Antimicrob. Chemother.* 24, 533 (1989); D. W. Denning et al., *Eur. J. Clin. Microbiol. Infect. Dis.* 9, 693 (1990) (each incorporated herein in their entireties). In vivo efficacy vs *Aspergillus* species is described in: J. Van Cutsem et al., *Antimicrob. Ag. Chemother.* 33, 2063 (1989) (incorporated herein in their entireties).

Saperconazole is co-crystallized with di-carboxylic acids by adding the drug and 0.5-1.1 equiv of the di-carboxylic acid in a solvent such as THF or dioxane with or without heat. 0.5-10 volumes of an antisolvent such as isopropylacetate, ethylacetate, butylacetate, methylacetate, t-butyl methylether, pentane, hexane, heptane, or any other hydrocarbon or hindered ether or hindered acetate that is miscible with the THF or dioxane would be added to reduce the solubility. The solution is filtered if desirable. If co-crystals do not form after incubation, the solution is cooled. An alternative method is to template the co-crystals of saperconazole using a co-crystal of cis-itraconazole. Other polar aprotic solvents, such as DMF or NMP could potentially be used as the solvents. In another alternative method, instead of using an antisolvent, the solvent is cooled or evaporated to saturate the system.

Example 21

Characterization of Co-Crystals

As exemplified herein, multi-component crystals of itraconazole formed from polar aprotic solvents or solvent mixtures of hydrocarbons with polar aprotic solvents, and required the presence of dicarboxylic acids. The ratio of itraconazole to diacid in the binary phases of itraconazole with fumaric acid and D,L-tartaric acid was shown to be 2:1 by solution $^1$H NMR of dissolved crystal samples. Thus, one equivalent of a dicarboxylic acid was tethering two drug molecules. Additional diacid-itraconazole combinations, selected based on similarity to fumaric and tartaric acid, containing one-half of an equivalent of diacid relative to itraconazole yielded crystalline compounds succinic acid, 1-malic acid, 1-tartaric acid and d-tartaric acid from THF. Compound succinic acid is perhaps the most surprising of these, since succinic acid has $pK_a$ values of 4.2 and 5.6, both of which exceed the $pK_a$ of the conjugate acid of Itraconazole. The initial crystallization of succinic acid was accomplished by seeding a solution with crystalline D,L-tartaric acid. Geometric fit appears to be more important than acid-base chemistry in directing crystallization of the compounds of Itraconazole with 1,4-dicarboxylic acids.

Figure 7:
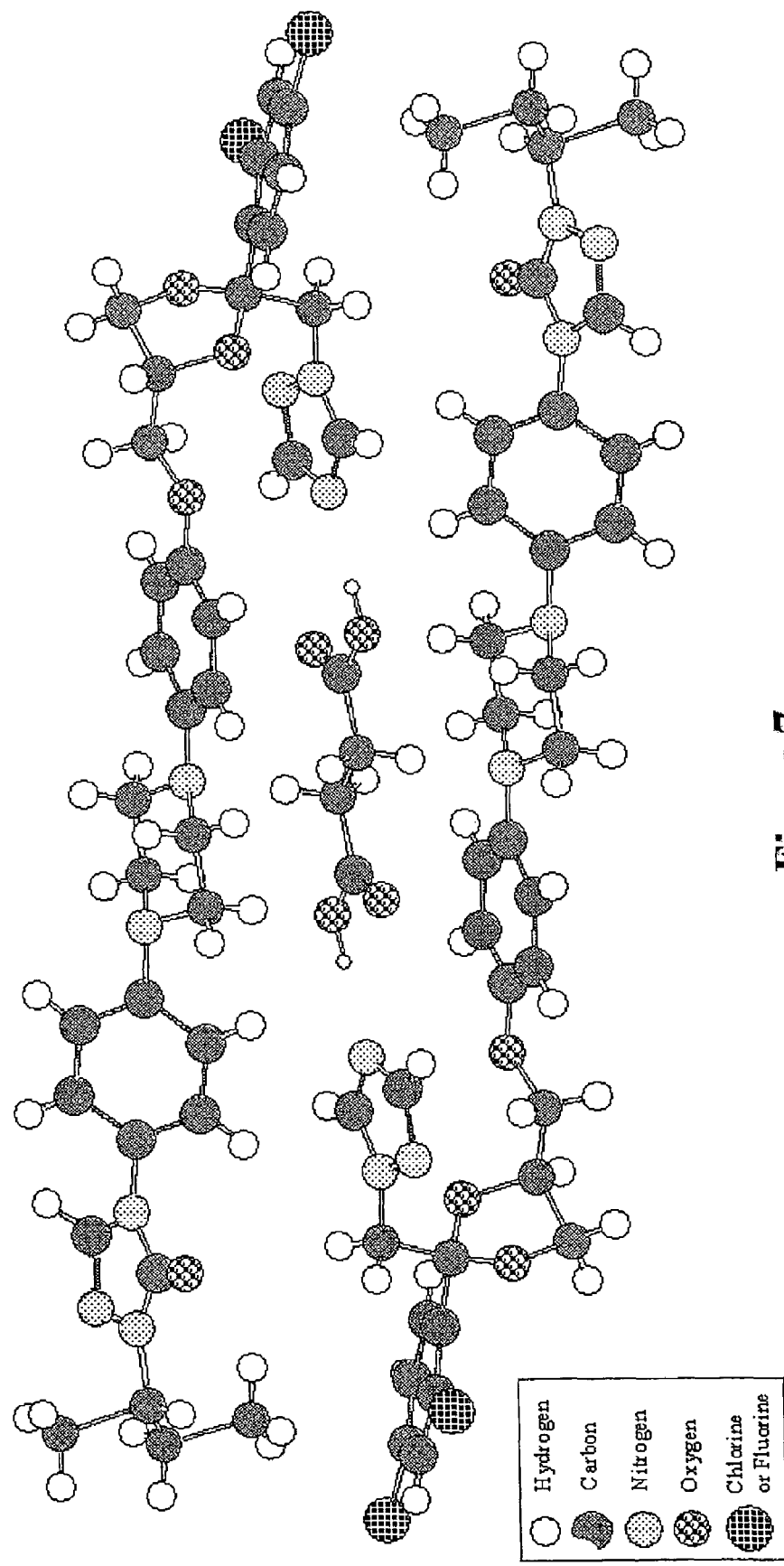
FIG. 7 A ball and stick model of a single trimeric congener consisting of two cis-itraconazole molecules and a succinic acid molecule.
Figure 8:
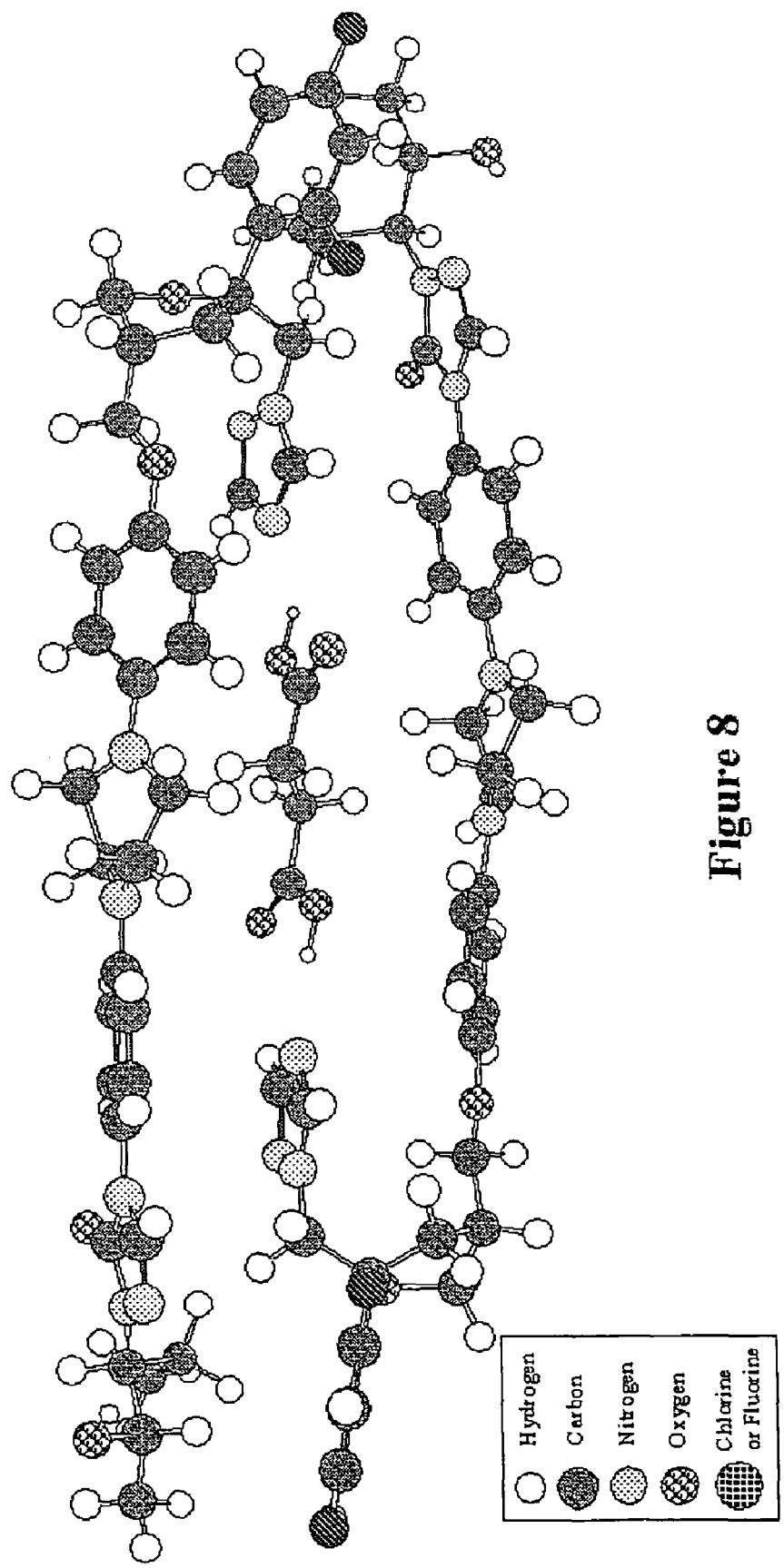
FIG. 8 A ball and stick model of a single trimeric congener consisting of two posaconazole molecules and a succinic acid molecule.
Figure 9:
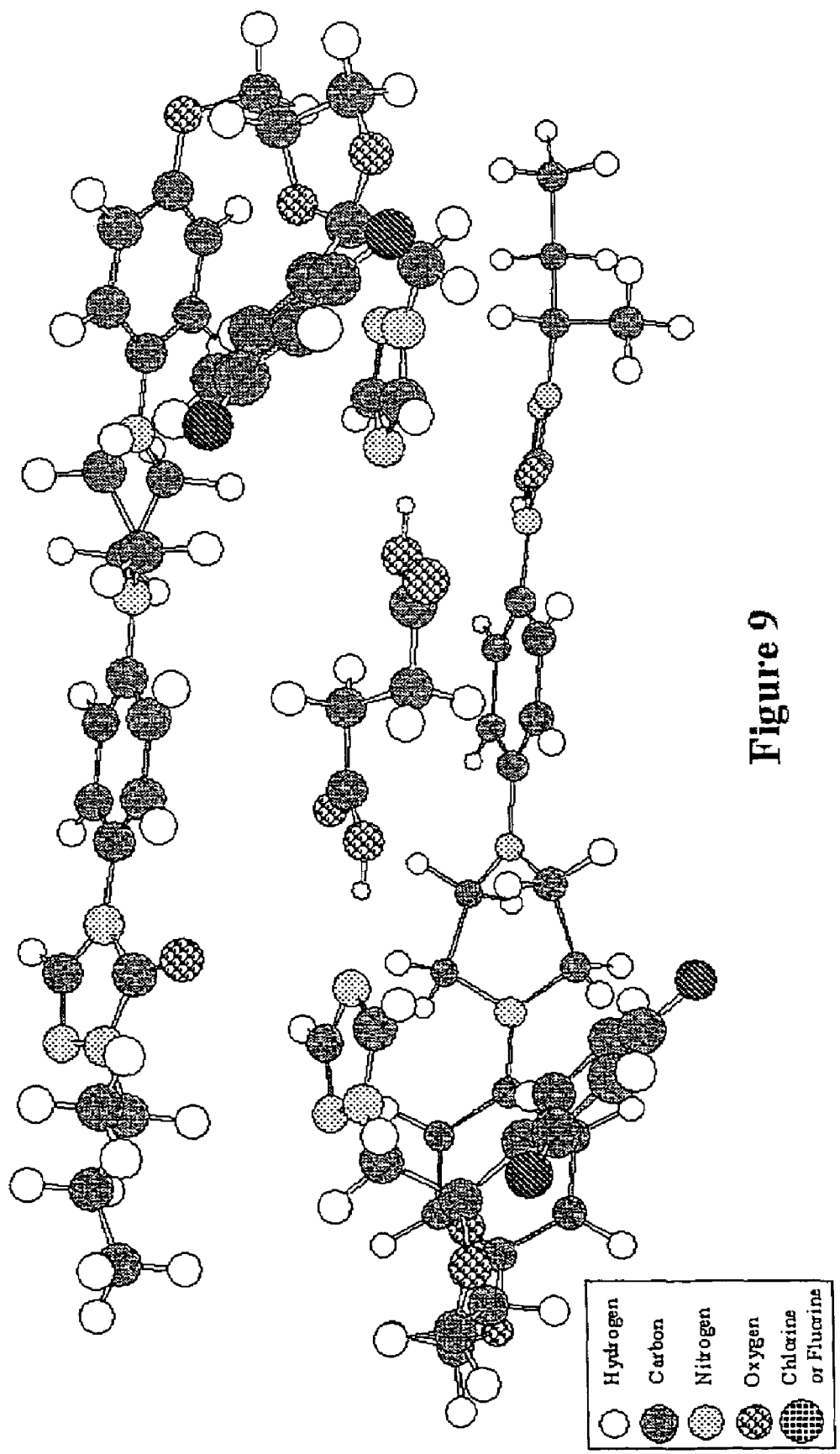
FIG. 9 A ball and stick model of a single trimeric congener consisting of two saperconazole molecules and a succinic acid molecule.

Hexagonal plate-like crystals of succinic acid were grown for single crystal X-ray structure determination from a solution in 10/2/1 1,2-dichloroethane/ethyl acetate/1,4-dioxane. FIGS. 7-9 shows the trimeric building block from the single-crystal structure of intraconazole and proposed crystal structures for posiconazole and saperconazole respectively. The two molecules of itraconazole are oriented in anti-parallel fashion to form a pocket with a triazole at either end. The extended succinic acid molecule fills the pocket, bridging the triazole groups. Interestingly, interaction between the 1,4-diacid and the strongest base on itraconazole (piperazine) is absent in the structure of succinic acid, but we cannot rule out an interaction of the alpha hydroxyl groups on tartaric or malic acid with the piperazine nitrogens.

Identification of multiple crystal forms of the same drug with acceptable solubility, dissolution and stability allows for selection of the optimal form for dosage form development. To demonstrate this feature, the dissolution of the co-crystals in aqueous medium was studied to assess their potential impact on bioavailability of the drug from a solid dosage form. The dissolution profiles of succinic acid, L-malic acid and L-tartaric acid (measured as free base equivalents of itraconazole) were compared to those of crystalline itraconazole and commercial Sporanox® beads (amorphous Itraconazole) in 0.1 N HCl. The results showed that crystal form 1-malic acid rivals the dissolution of the commercial product containing amorphous Itraconazole. In general, the co-crystals behave more similarly to Sporanox® than crystalline Itraconazole. The ability of the co-crystal forms to achieve and sustain supersaturation of Itraconazole in the dissolution test for over 8 hours is noteworthy; the co-crystal forms maintain 4- to 20-fold higher concentrations than that achieved from crystalline Itraconazole. The practical implication is significant, since the ability to form a supersaturated solution, even transiently, can have dramatic impact on absorption and bioavailability.

Example 22

Cis-Itraconazole HCl:DL-Tartaric Acid Co-Crystal

A DL-tartaric acid co-crystal of itraconazole hydrochloride was prepared. To a suspension of itraconazole freebase (20.1 g, 0.0285 mol) in absolute ethanol (100 mL) was added a solution of hydrochloric acid (HCl) (1.56 g, 0.0428 mol) and DL-tartaric acid (2.99 g, 0.0171 mol) in absolute ethanol (100 mL). A clear solution formed with stirring and heating to reflux. The hot solution was gravity filtered and allowed to cool to room temperature (25° C.). Upon cooling, white crystals formed. The solid was collected by filtration and washed with cold absolute ethanol (15 mL). The white solid was dried in a vacuum oven overnight at 80° C. The crystalline substance was found to be a DL-tartaric acid co-crystal of itraconazole hydrochloride. The solid was characterized by PXRD and DSC, as shown in FIGS. 12(*a*) and 12(*b*), respectively.

Figure 12A:
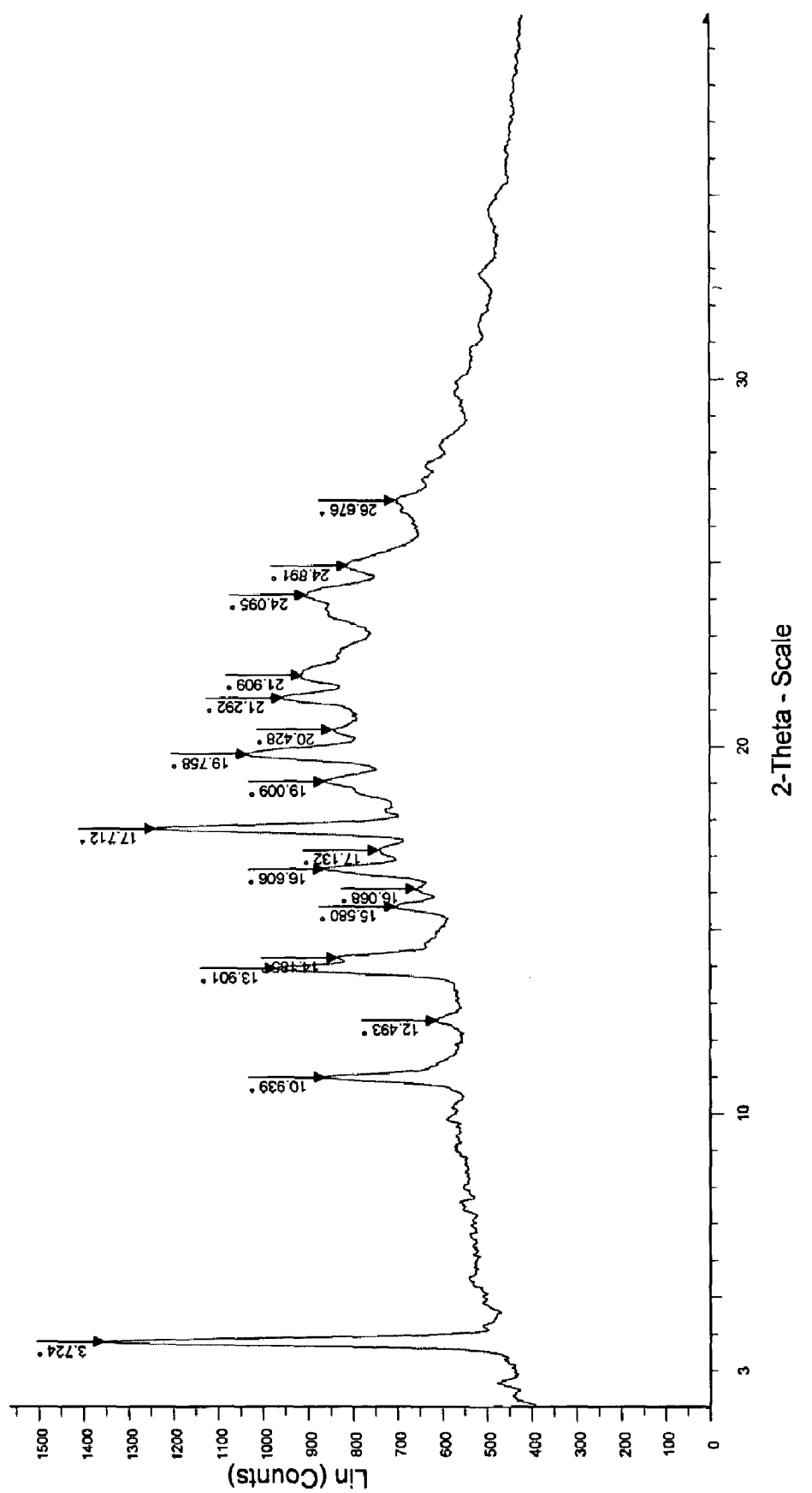
FIG. 12(a)-(b) illustrate the following:
(a) PXRD diffractogram of a cis-itraconazole HCl:DL-tartaric acid co-crystal.
(b) DSC thermogram of a cis-itraconazole HCl:DL-tartaric acid co-crystal.
Figure 12B:
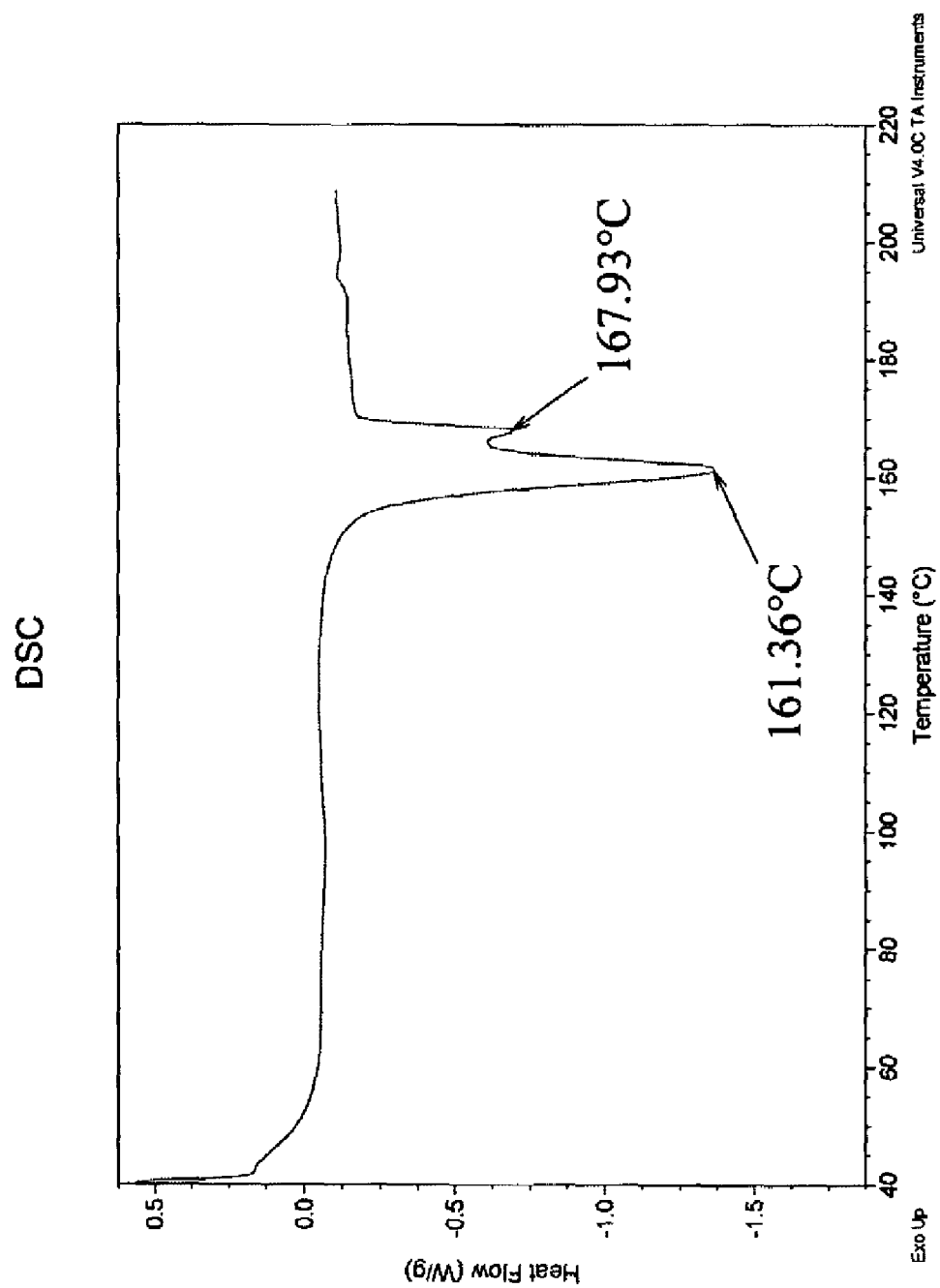

The cis-itraconazole HCl:DL-tartaric acid co-crystal can be characterized by any one, any two, any three, any four, any five, or any six or more of the peaks in FIG. 12(*a*) including, but not limited to, 3.72, 10.94, 13.90, 14.19, 16.61, 17.71, 19.01, 19.76, 21.29, 21.91, 24.10, and 24.89 degrees 2-theta (Rigaku, data as collected).

The DSC thermogram of the cis-itraconazole HCl:DL-tartaric acid co-crystal showed an endothermic transition at about 161 degrees C., as shown in FIG. 12(*b*).

Example 23

Cis-Itraconazole HCl:D-Tartaric Acid Co-Crystal

A D-tartaric acid co-crystal of itraconazole hydrochloride was prepared. To a suspension of itraconazole freebase (20.1 g, 0.0285 mol) in absolute ethanol (100 mL) was added a solution of hydrochloric acid (HCl) (1.56 g, 0.0428 mol) and D-tartaric acid (2.99 g, 0.0171 mol) in absolute ethanol (100 mL). A clear solution formed with stirring and heating to reflux. The hot solution was gravity filtered and allowed to cool to room temperature (25° C.). Upon cooling, white crystals formed. The solid was collected by filtration and washed with cold absolute ethanol (15 mL). The white solid was dried in a vacuum oven overnight at 80° C. The crystalline substance was found to be a D-tartaric acid co-crystal of itraconazole hydrochloride. The solid was characterized by PXRD and DSC, as shown in FIGS. 13(a) and 13(b), respectively.

Figure 13A:
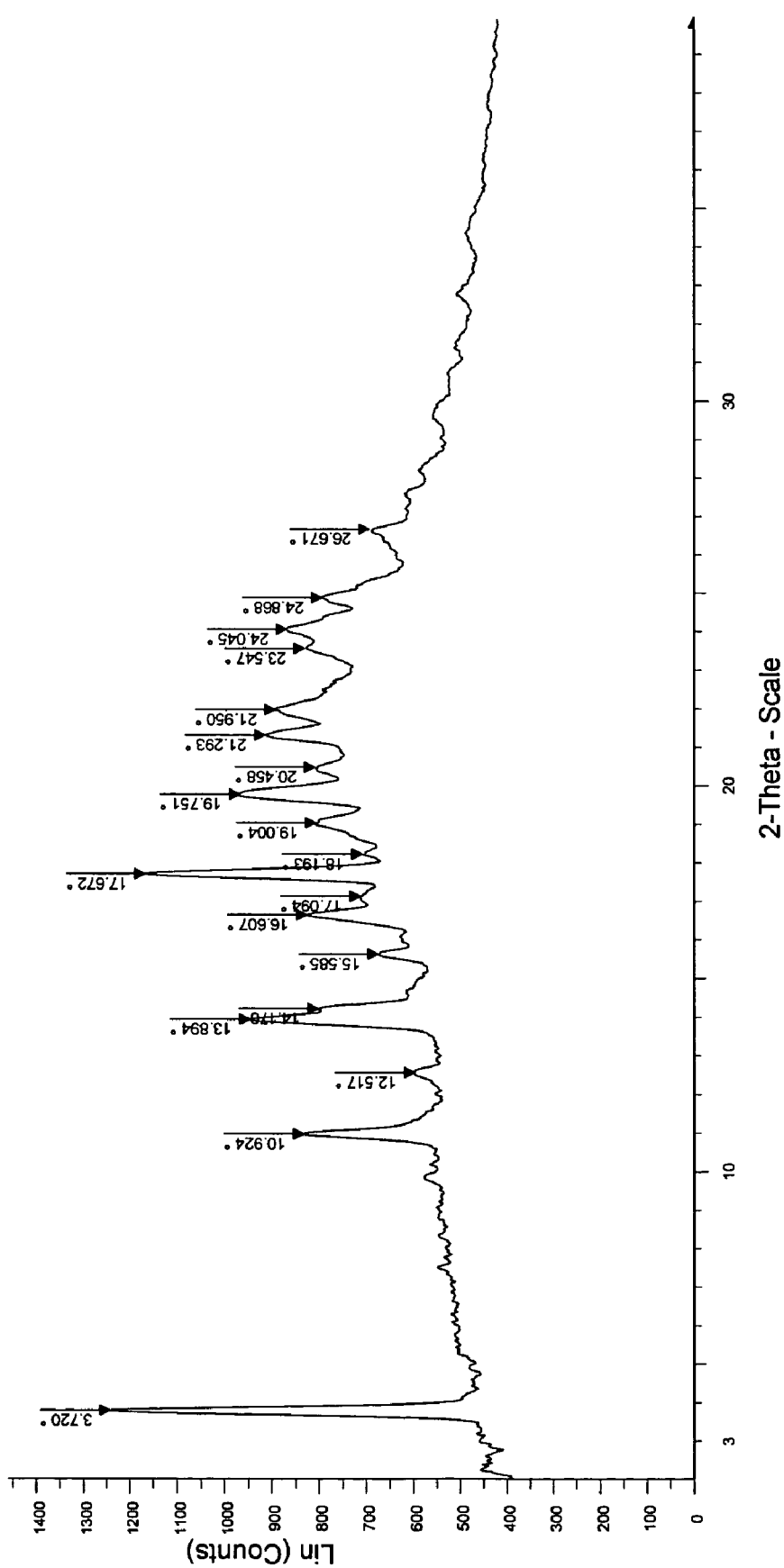
FIG. 13(a)-(b) illustrate the following:
(a) PXRD diffractogram of a cis-itraconazole HCl:D-tartaric acid co-crystal.
(b) DSC thermogram of a cis-itraconazole HCl:D-tartaric acid co-crystal.

The cis-itraconazole HCl:D-tartaric acid co-crystal can be characterized by any one, any two, any three, any four, any five, or any six or more of the peaks in FIG. 13(a) including, but not limited to, 3.72, 10.92, 13.89, 14.17, 16.61, 17.67, 19.00, 19.75, 21.29, 21.95, 24.05, and 24.87 degrees 2-theta (Rigaku, data as collected).

Figure 13B:
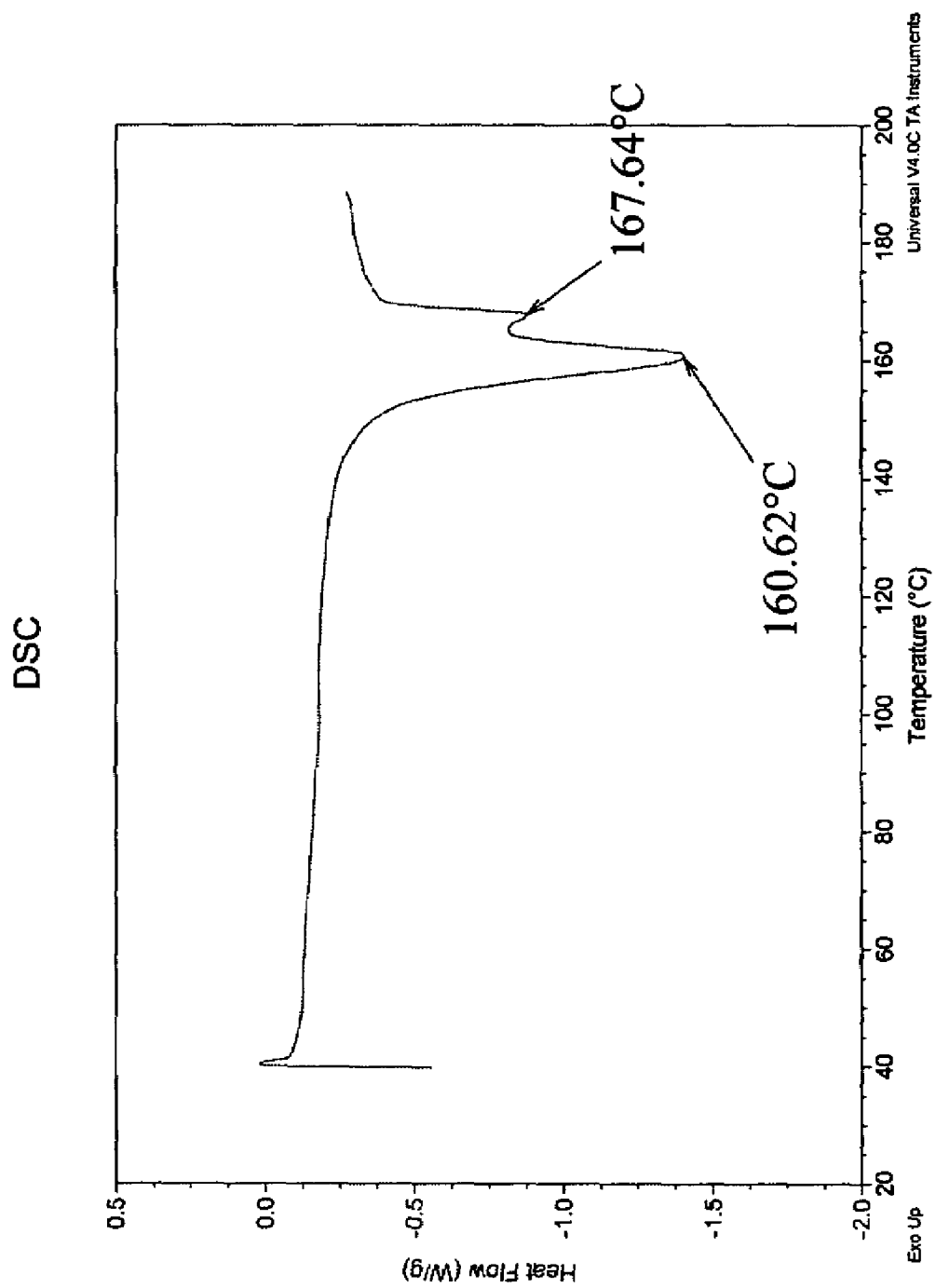

The DSC thermogram of the cis-itraconazole HCl:DL-tartaric acid co-crystal showed an endothermic transition at about 161 degrees C., as shown in FIG. 13(b).

Example 24

Cis-Itraconazole HCl:L-Tartaric Acid Co-Crystal

An L-tartaric acid co-crystal of itraconazole hydrochloride was prepared. To a suspension of itraconazole freebase (20.1 g, 0.0285 mol) in absolute ethanol (100 mL) was added a solution of hydrochloric acid (HCl) (1.56 g, 0.0428 mol) and L-tartaric acid (2.99 g, 0.0171 mol) in absolute ethanol (100 mL). A clear solution formed with stirring and heating to reflux. The hot solution was gravity filtered and allowed to cool to room temperature (25° C.). Upon cooling, white crystals formed. The solid was collected by filtration and washed with cold absolute ethanol (15 mL). The white solid was dried in a vacuum oven overnight at 80° C. The crystalline substance was found to be an L-tartaric acid co-crystal of itraconazole hydrochloride. The solid was characterized by PXRD and DSC, as shown in FIGS. 14(a) and 14(b), respectively.

Figure 14A:
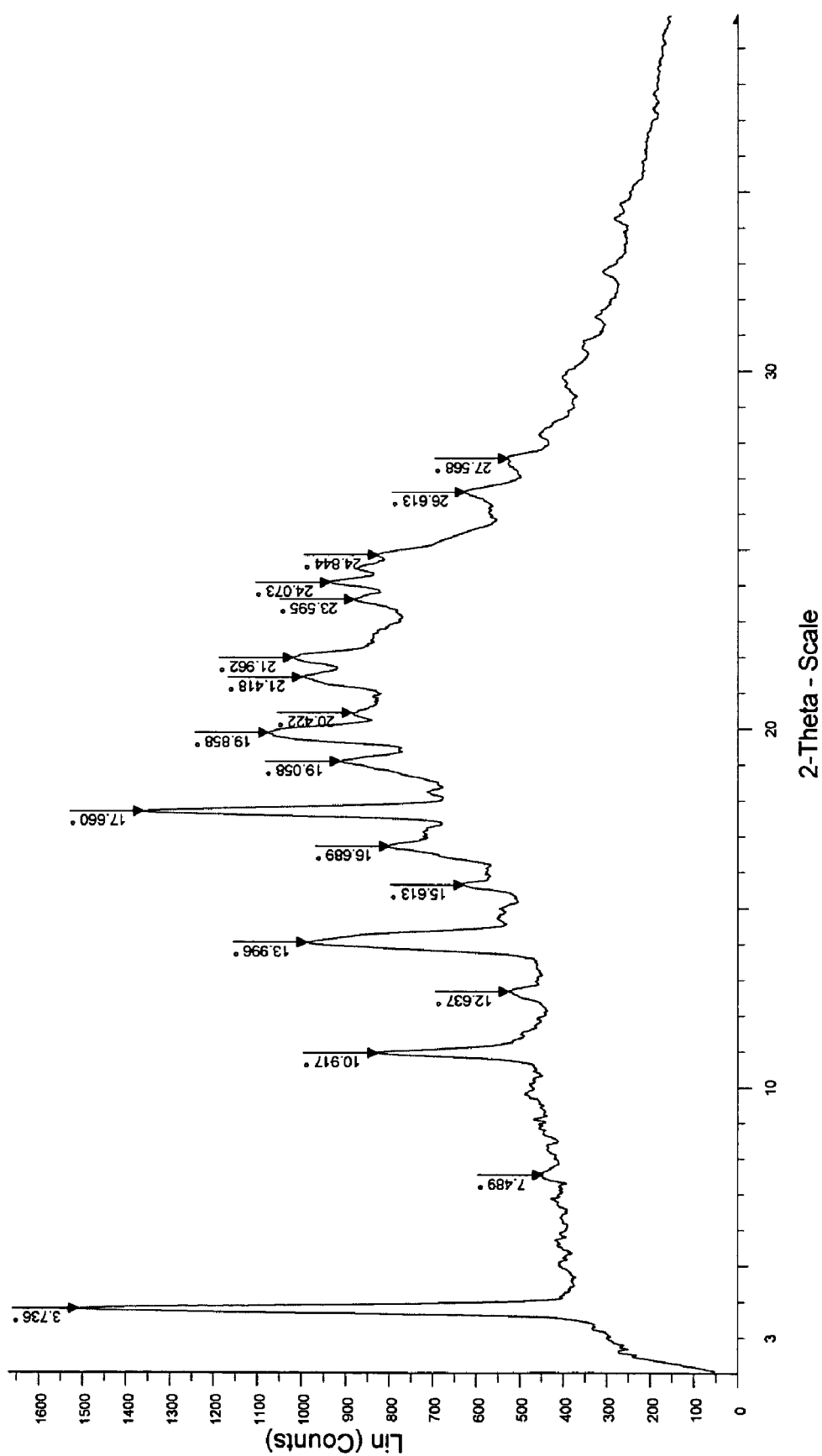
FIG. 14(a)-(b) illustrate the following:
(a) PXRD diffractogram of a cis-itraconazole HCl:L-tartaric acid co-crystal.
(b) DSC thermogram of a cis-itraconazole HCl:L-tartaric acid co-crystal.

The cis-itraconazole HCl:L-tartaric acid co-crystal can be characterized by any one, any two, any three, any four, any five, or any six or more of the peaks in FIG. 14(a) including, but not limited to, 3.74, 10.92, 14.00, 16.69, 17.66, 19.06, 19.86, 21.42, 21.96, 24.07, and 24.84 degrees 2-theta (Rigaku, data as collected).

Figure 14B:
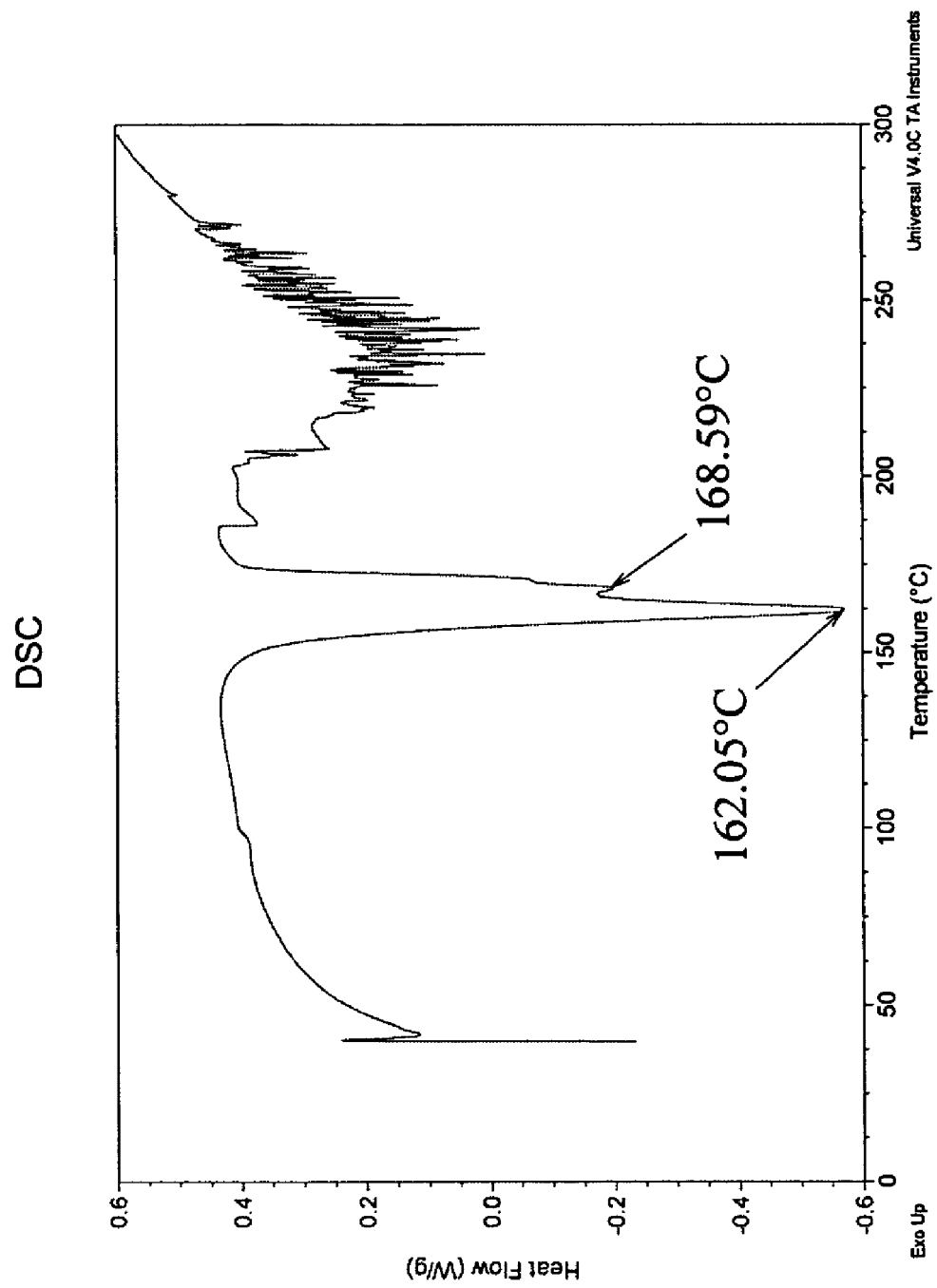

The DSC thermogram of the cis-itraconazole HCl:DL-tartaric acid co-crystal showed an endothermic transition at about 162 degrees C., as shown in FIG. 14(b).

Co-crystals of a salt of cis-itraconazole exhibited decreased hygroscopicity over that of the cis-itraconazole salt. In the case of cis-itraconazole HCl:DL-tartaric acid, cis-itraconazole HCl:D-tartaric acid, and cis-itraconazole HCl:L-tartaric acid co-crystals, the DL-tartaric acid co-crystal has the lowest hygroscopicity of the three co-crystals. This may be due to the presence of a di-HCl cis-itraconazole salt in the D- and L-tartaric acid co-crystal samples.

In addition, the stability of the cis-itraconazole HCl:DL-tartaric acid co-crystal is higher under certain solvent conditions than that in a co-crystal with the free base, such as cis-itraconazole:succinic acid. The cis-itraconazole HCl:DL-tartaric acid co-crystal is stable over time in solvent while the cis-itraconazole:succinic acid co-crystal can dissociate into free base and succinic acid. This shows that the cis-itraconazole HCl:DL-tartaric acid co-crystal is a better candidate for development into a pharmaceutical composition or medicament than the cis-itraconazole:succinic acid co-crystal.

Finally, the tartaric acid co-crystals of cis-itraconazole HCl salt wet with water, while co-crystals comprising the free base of cis-itraconazole repel water. As above, this also shows that cis-itraconazole HCl:DL-tartaric acid co-crystal is a better candidate for development into a pharmaceutical composition or medicament than the cis-itraconazole:succinic acid co-crystal.

Example 25

In Vivo Study of Oral Bioavailability in Dogs

Formulation M1 Preparation—Itraconazole HCl:DL-Tartaric Acid Co-Crystal 367.0 mg of hydroxypropyl cellulose 100,000 (HPC) was weighed into a glass mortar. 366.3 mg of itraconazole HCl:DL-tartaric acid co-crystal was added to the mortar. The components were ground using a pestle and mixed with a spatula until the powder appeared well mixed and uniform in appearance.

736.9 mg of d-alpha tocopheryl polyethylene glycol 1000 succinate (TPGS) was added to a vial and heated to 60 degrees C. to melt.

The blended powder of co-crystal and HPC was added to the molten TPGS and mixed by both vortexing and stirring with a spatula until uniform. The formulation was left to cool to room temperature resulting in a waxy, white solid. The resultant formulation was labeled M1.

An investigation of the effect of gastric pH on the pharmacokinetic behavior of itraconazole and its main metabolite, hydroxy-itraconazole, following oral administration of Sporanox® and formulation M1 (See M1 preparation above) in male beagle dogs was completed. A dose of 2.5 mg/kg was employed. This dose compares roughly with that used by humans (100 mg/70 kg person is about 1.4 mg/kg; occasionally doses of 200 mg are used, per package insert for Sporanox® capsule). In a first series of dog experiment, gastric pH was lowered to about pH 2 by subcutaneous injection of pentagastrin. Approximately 40 to 50 minutes prior to dose administration, a solution of pentagastrin was administered subcutaneously to each dog at a dose volume of 0.1 mL/kg in an attempt to stimulate gastric secretion. Pentagastrin was prepared as a solution in dimethylsulfoxide (DMSO) and hydroxypropyl beta-cyclodextrin (HPCD in water) on the day of dose administration at a concentration of 1.5 mg/mL. When the gastric pH reached a value of approximately 2.0 (actual range: 1.9 to 2.4), dogs received their formulations. Animals were administered Sporanox® beads (2.5 mg itraconazole/kg) and one week later (i.e., washout period) the M1 formulation was administered (2.5 mg itraconazole/kg) following the same protocol of pentagastrin pre-treatment. In a second set of experiments, gastric pH was increased (i.e., to about pH 7 or 8) by oral administration of a commercial formulation of Pepcid® AC (10 mg total dose/dog). Subsequently, 2 of 4 dogs received Sporanox® orally at a dose of 2.5 mg itraconazole/kg while the remaining 2 animals were dosed with an oral dose of M1. Following each dose administration, blood samples were serially taken and plasma samples were analyzed for parent drug and its hydroxy metabolite. The pharmacokinetic analyses of itraconazole and hydroxy-itraconazole in plasma were performed using the PHAST® software program (Version 2.3-004, Phoenix International Life Sciences Inc.). The highest experimental concentration was considered to be the peak concentration ($C_{max}$). Time to $C_{max}$ was denoted $T_{max}$ (observed value). The observed terminal phase rate constant ($K_{el}$) was calculated from the terminal 2 or more points (non-zero and non-$C_{max}$), whenever possible, of the log-linear regression (number of points included in the calculation was such to optimize the $r^2$ value of the regression analysis). Terminal phase half-life ($t_{1/2}$) was determined by dividing 0.693 by $K_{el}$. The area under the plasma concentration versus time curve from time zero to the last quantifiable concentration (AUC$_{0-t}$) was calculated by the linear trapezoidal method. AUC$_{0-\infty}$, the area under the plasma concentration versus time curve from time zero to infinity, was calculated as the sum of AUC$_{0-t}$ plus the ratio of the last plasma concentration to K$_{el}$. The apparent systemic clearance (CL/F) was determined by dividing the dose by the area under the curve from time zero to infinity. Values below the limit of quantification were assigned a value of zero for pharmacokinetic analysis.

Table 22 shows the results of an in vivo study of the pharmacokinetic parameters of itraconazole in plasma following a single oral administration of Sporanox® or formulation M1 to male beagle dogs.

TABLE 22

| Animal ID | Formulation Administered (pretreatment) | AUC$_{0-t}$ | AUC$_{0-\infty}$ | t$_{1/2}$ | C$_{max}$ | T$_{max}$ | CL/F |
|---|---|---|---|---|---|---|---|
| 1001 | Sporanox® | 7532.58 | 8283.01 | 48.9 | 338.27 | 1.00 | 301.82 |
| 1002 | (Pentagastrin) | 5316.48 | 6138.17 | 63.9 | 279.12 | 1.50 | 407.29 |
| 1003 |  | 9833.03 | 10365.91 | 39.5 | 403.95 | 1.50 | 241.18 |
| 1004 |  | 3532.56 | 4395.89 | 30.7 | 224.53 | 1.50 | 568.71 |
| Mean |  | 6553.66 | 7295.74 | 45.76 | 311.47 | 1.38 | 379.75 |
| SD |  | 2730.70 | 2591.64 | 14.20 | 77.19 | 0.25 | 143.46 |
| 1001 | M1 | 4898.91 | 6381.53 | 37.0 | 266.43 | 2.00 | 3917.55 |
| 1002 | (Pentagastrin) | 3827.08 | 4614.37 | 71.9 | 181.20 | 1.50 | 5417.86 |
| 1003 |  | 4994.43 | 5854.15 | 26.6 | 225.72 | 2.50 | 4270.48 |
| 1004 |  | 4851.26 | 5410.18 | 22.7 | 325.18 | 2.00 | 4620.92 |
| Mean |  | 4642.92 | 5565.06 | 39.55 | 249.63 | 2.00 | 4556.70 |
| SD |  | 547.14 | 747.89 | 23.39 | 61.22 | 0.41 | 641.91 |
| 1001 | Sporanox® | 1546.62 | 2066.38 | 25.88 | 108.42 | 1.00 | 1209.85 |
| 1002 | (Pepcid® AC) | 1257.27 | 2087.57 | 47.25 | 82.45 | 1.00 | 1197.57 |
| Mean |  | 1401.94 | 2076.97 | 36.57 | 95.44 | 1.00 | 1203.71 |
| 1003 | M1 | 1679.97 | 2127.32 | 23.14 | 85.20 | 1.50 | 1175.19 |
| 1004 | (Pepcid® AC) | 2740.34 | 3486.85 | 18.80 | 110.30 | 2.00 | 716.98 |
| Mean |  | 2210.16 | 2807.08 | 20.97 | 97.75 | 1.75 | 946.08 |

AUC$_{0-\infty}$: The area under the plasma concentration versus time curve from time zero to infinity (ng · hr/mL)
AUC$_{0-t}$: The area under the plasma concentration versus time curve from time zero to 24 hr post-dose (ng · hr/mL)
C$_{max}$: The highest observable concentration (ng/mL)
t$_{1/2}$: Terminal phase half-life (hr)
CL/F: Clearance (mL/hr · kg)
T$_{max}$: Time to Cmax (hr)
Untruncated values were used for calculation purposes A comparison of the pentagastrin pretreatment data (acidic stomach) with the Pepcid® AC pretreatment data (basic stomach) shows about a four-fold decrease in AUC of Sporanox® and about a two-fold decrease in AUC of formulation M1. Surprisingly, these data show a significantly decreased food effect in the M1 formulation when compared to Sporanox®. The M1 formulation is shown, in Table 22, to have a decreased sensitivity to the pH increase in the stomach when compared to Sporanox®.

Table 23 shows the concentrations of hydroxy-itraconazole metabolite in plasma (ng/mL) following the above single oral administration of Sporanox® (2.5 mg itraconzole/kg) to male beagle dogs (pentagastrin administration).

TABLE 23

| Timepoint[a] | Animal No. | | | | Mean | SD | CV |
|---|---|---|---|---|---|---|---|
|  | 1001 | 1002 | 1003 | 1004 |  |  |  |
| Pre-dose | BLQ | BLQ | BLQ | BLQ | NC | NC | NC |
| 0.5 | 5.63 | BLQ | BLQ | BLQ | 1.41 | 2.82 | 200 |
| 1 | 42.74 | 16.60 | 28.57 | 20.66 | 27.14 | 11.53 | 43 |
| 1.5 | 60.69 | 48.21 | 79.38 | 47.17 | 58.86 | 14.99 | 26 |
| 2 | 90.32 | 55.73 | 92.81 | 64.68 | 75.89 | 14.50 | 24 |
| 2.5 | 93.05 | 56.37 | 130.32 | 62.74 | 85.62 | 33.82 | 40 |
| 4 | 110.20 | 61.04 | 134.92 | 70.94 | 94.28 | 34.42 | 37 |
| 6 | 103.05 | 47.49 | 120.87 | 77.25 | 87.17 | 31.94 | 37 |
| 8 | 93.40 | 46.05 | 112.33 | 77.81 | 82.40 | 28.04 | 34 |
| 12 | 73.05 | 37.95 | 95.94 | 58.68 | 66.41 | 24.40 | 37 |
| 24 | 73.82 | 31.96 | 77.38 | 68.34 | 62.88 | 20.94 | 33 |
| 48 | 61.38 | 26.68 | 102.92 | 34.16 | 56.29 | 34.48 | 61 |
| 72 | 48.48 | 27.04 | 45.81 | 27.37 | 37.18 | 11.56 | 31 |
| 168 | 131.13 | 8.36 | 23.04 | BLQ | 40.63 | 61.08 | 150 |

[a]Refers to time post-dose (hr)
BLQ: Below limit of quantification
NC: Not calculated Table 24 shows the concentrations of hydroxy-itraconazole metabolite in plasma (ng/mL) following the above single oral administration of formulation M1 (2.5 mg intraconazole/kg) to male beagle dogs (pentagastrin administration).

TABLE 24

| Timepoint[a] | Animal No. | | | | Mean | SD | CV |
|---|---|---|---|---|---|---|---|
| | 1001 | 1002 | 1003 | 1004 | | | |
| Pre-dose | BLQ | BLQ | BLQ | BLQ | NC | NC | NC |
| 0.5 | BLQ | BLQ | BLQ | BLQ | NC | NC | NC |
| 1 | 12.41 | 21.99 | 10.89 | 20.08 | 16.34 | 5.51 | 34 |
| 1.5 | 35.21 | 36.98 | 25.00 | 43.65 | 35.21 | 7.72 | 22 |
| 2 | 72.92 | 42.18 | 47.45 | 63.66 | 46.55 | 14.23 | 25 |
| 2.5 | 72.20 | 32.87 | 54.90 | 69.96 | 57.48 | 18.12 | 32 |
| 4 | 98.04 | 37.57 | 100.86 | 84.12 | 80.15 | 29.31 | 37 |
| 6 | 102.23 | 39.56 | 102.14 | 94.56 | 84.62 | 30.26 | 36 |
| 8 | 82.95 | 48.71 | 87.60 | 93.38 | 78.16 | 20.09 | 26 |
| 12 | 82.05 | 33.66 | 79.98 | 81.38 | 69.27 | 23.75 | 34 |
| 24 | 65.00 | 27.71 | 43.46 | 58.95 | 48.78 | 16.72 | 34 |
| 48 | 87.96 | 18.56 | 30.06 | 45.92 | 45.63 | 30.37 | 67 |
| 72 | 49.27 | 21.93 | 23.35 | 23.69 | 29.56 | 13.16 | 45 |
| 168 | 13.44 | 9.45 | 12.51 | 8.37 | 10.94 | 2.42 | 22 |

[a]Refers to time post-dose (hr)
BLQ: Below limit of quantification
NC: Not calculated Formulation J12A Preparation—Itraconazole HCl:DL-Tartaric Acid Co-crystal 250.3 mg of itraconazole HCl:DL-tartaric acid co-crystal, 600.1 mg of 5 cps hydroxypropyl methylcellulose (HPMC) and 50.3 mg of alpha-lactose monohydrate were dispensed into a glass mortar. The components were ground using a pestle and mixed with a spatula until the powder appeared well mixed and uniform in appearance.

50 microliters of isopropanol was added to the mortar as a granulating fluid. The mixture was ground and mixed until a uniform consistency was observed.

The formulation was pressed into pellets using a Stokes Tablet Press (DT Industries model 511). Pellets were pressed to a diameter of 2.38 mm, and a height of 1.30 mm at an average applied pressure of 14000 psi. The average pellet mass was 5.8 mg. The resultant formulation was labeled J12A.

An investigation of the pharmacokinetic behavior of itraconazole following oral administration of a minitablet formulation in male beagle dogs was completed. Samples were analyzed for both the parent drug (itraconazole) and its hydroxy metabolite. Prior to dose administration and following an overnight fast, 2 male beagle dogs were weighed and their gastric pH adjusted to about pH 2 by administration of a solution of pantagastrin. The dogs' gastric pH was measured by telemetry and recorded for all animals prior to dose administration. Approximately 40 to 50 minutes prior to dose administration, a solution of pentagastrin was administered subcutaneously to each dog at a dose volume of 0.1 mL/kg in an attempt to stimulate gastric secretion. Pentagastrin was prepared as a solution in dimethylsulfoxyde (DMSO) and hydroxypropyl beta-cyclodextrin (HPCD in water) on the day of dose administration at a concentration of 1.5 mg/mL. When the gastric pH reached a value of approximately 2.0 (actual range: 1.9 to 2.4), dogs received one capsule of J12A orally at a target dose of itraconazole of 2.5 mg/kg. Following dose administration, blood samples were collected from each animal by jugular venipuncture at selected time-points.

Table 25 shows the concentrations of itraconazole and hydroxy-itraconazole in plasma (ng/mL) following a single oral administration (2.5 mg/kg) of J12A to male beagle dogs.

TABLE 25

| Time-Point (hr) | Itraconazole Animal No. | | | | Hydroxy Animal No. | | | |
|---|---|---|---|---|---|---|---|---|
| | 3001 | 3002 | Mean | SD | 3001 | 3002 | Mean | SD |
| Pre-dose | BLQ | BLQ | NC | NC | BLQ | BLQ | NC | NC |
| 1 | 15 | 12 | 14 | 2.0 | BLQ | BLQ | NC | NC |
| 2 | 90 | 114 | 102 | 17 | 9.0 | 13 | 11 | 2.6 |
| 4 | 190 | 202 | 196 | 8.7 | 42 | 46 | 44 | 3.2 |
| 8 | 139 | 101 | 120 | 27 | 46 | 48 | 47 | 1.4 |
| 12 | 115 | 70 | 92 | 32 | 47 | 42 | 45 | 3.2 |
| 24 | 58 | 55 | 56 | 1.6 | 42 | 41 | 42 | 1.1 |
| 48 | 32 | 25 | 29 | 5.5 | 20 | 23 | 22 | 2.1 |
| 72 | 24 | 17 | 20 | 5.1 | 11 | 16 | 13 | 3.4 |

Calculations performed using untruncated values
NC: Not Calculated when all individual values were BLQ
BLQ: Below limit of quantification Table 26 shows the mean pharmacokinetic parameters of itraconazole in plasma following a single oral administration of J12A (2.5 mg itraconazole/kg) to male beagle dogs.

TABLE 26

| $AUC_{0-t}$ (ng · hr/mL) | $C_{max}$ (ng/mL) | $T_{max}$ (hr) | $AUC_{0-\infty}$ (ng · hr/mL) | $T_{1/2}$ (hr) | CL (mL/hr/kg) |
|---|---|---|---|---|---|
| 3916 | 196 | 4.0 | 4911 | 33 | 520 |

$AUC_{0-\infty}$: The area under the plasma concentration versus time curve from time zero to infinity (ng · hr/mL)
$AUC_{0-t}$: The area under the plasma concentration versus time curve from time zero to 24 hr post-dose (ng · hr/mL)
$C_{max}$: The highest observable concentration (ng/mL)
$T_{max}$: Time to Cmax (hr)
$T_{1/2}$: Terminal phase half-life (hr)
CL: Clearance (mL/hr · kg)
Untruncated values were used for calculation purposes
Reported values are rounded to 2 significant figures Table 27 shows the mean pharmacokinetic parameters of hydroxy-itraconazole in plasma following a single oral administration of J12A (2.5 mg itraconazole/kg) to male beagle dogs.

TABLE 27

| $AUC_{0-t}$ (ng · hr/mL) | $C_{max}$ (ng/mL) | $T_{max}$ (hr) | $AUC_{0-\infty}$ (ng · hr/mL) | $T_{1/2}$ (hr) |
|---|---|---|---|---|
| 2084 | 47 | 10 | 2796 | 35 |

$AUC_{0-\infty}$: The area under the plasma concentration versus time curve from time zero to infinity (ng · hr/mL)
$AUC_{0-t}$: The area under the plasma concentration versus time curve from time zero to 24 hr post-dose< (ng · hr/mL)
$C_{max}$: The highest observable concentration (ng/mL)
$T_{max}$: Time to Cmax (hr)
$T_{1/2}$: Terminal phase half-life (hr)
Untruncated values were used for calculation purposes While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

What is claimed is:

1. A pharmaceutically acceptable co-crystal of the compound, 4-[4-[4-[4-[[2-(2,4-dichlorophenyl)-2-( 1H-1,2,4-triazol- 1-ylmethyl)-1,3-dioxolan-4-yl]methoxy]phenyl]-1-piperazinyl]phenyl]-2,4-dihydro-2-(1-methylpropyl)-3H-1,2,4-triazol-3-one hydrochloride, wherein the co-crystal further comprises a carboxylic acid co-crystal former.

2. The pharmaceutically acceptable co-crystal of claim 1, wherein the co-crystal former is selected from the group consisting of tartaric acid, fumaric acid, malonic acid, maleic acid, adipic acid, malic acid, and succinic acid.

3. The pharmaceutically acceptable co-crystal of claim 1, wherein the compound is selected from the group consisting of:

(+)-[2R-[2α,4α,4(R)]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one hydrochloride, (+)-[2R-[2α,4α,4(S)]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one hydrochloride, (−)-[2S-[2α,4α,4(R)]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one hydrochloride, and (−)-[2S-[2α,4α,4(S)]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one hydrochloride.

* * * * *